(12) United States Patent
Kasibhatla et al.

(10) Patent No.: US 7,129,244 B2
(45) Date of Patent: Oct. 31, 2006

(54) TRIAZOLOPYRIMIDINES AND RELATED ANALOGS AS HSP90-INHIBITORS

(75) Inventors: Srinivas Rao Kasibhatla, San Diego, CA (US); Kevin D. Hong, San Diego, CA (US); Marcus F. Boehm, San Diego, CA (US)

(73) Assignee: Conforma Therapeutics Corporation, San Diego, CA (US)

( * ) Notice: Subject to any disclaimer, the term of this patent is extended or adjusted under 35 U.S.C. 154(b) by 0 days.

(21) Appl. No.: 10/946,628

(22) Filed: Sep. 20, 2004

(65) Prior Publication Data

US 2005/0113339 A1     May 26, 2005

Related U.S. Application Data

(60) Provisional application No. 60/591,467, filed on Jul. 26, 2004, provisional application No. 60/504,135, filed on Sep. 18, 2003.

(51) Int. Cl.
| | |
|---|---|
| C07D 487/04 | (2006.01) |
| A61P 37/06 | (2006.01) |
| A61P 35/00 | (2006.01) |
| A61P 29/00 | (2006.01) |
| A61K 31/519 | (2006.01) |

(52) U.S. Cl. .................. 514/261.1; 544/254; 544/323
(58) Field of Classification Search ................ 544/254; 514/261.1
See application file for complete search history.

(56) References Cited

U.S. PATENT DOCUMENTS

| | | | |
|---|---|---|---|
| 4,495,190 A | 1/1985 | Hagberg et al. | |
| 4,547,573 A | 10/1985 | Jung et al. | |
| 4,617,304 A | 10/1986 | Ashton et al. | |
| 4,699,877 A | 10/1987 | Cline et al. | |
| 4,748,177 A | 5/1988 | Sircar et al. | |
| 4,772,606 A | 9/1988 | Sircar et al. | |
| 4,774,325 A | 9/1988 | Casadio et al. | |
| 4,806,642 A | 2/1989 | Sircar et al. | |
| 4,918,162 A | 4/1990 | Slamon et al. | |
| 4,921,859 A | 5/1990 | Sircar et al. | |
| 4,923,885 A * | 5/1990 | Hupe et al. .................. 514/359 |
| 4,968,603 A | 11/1990 | Slamon et al. | |
| 5,002,950 A | 3/1991 | Malone et al. | |
| 5,098,906 A | 3/1992 | Sircar et al. | |
| 5,110,818 A | 5/1992 | Allgeier | |
| 5,204,353 A | 4/1993 | Meier et al. | |
| 5,217,866 A | 6/1993 | Summerton et al. | |
| 5,602,156 A | 2/1997 | Kohn et al. | |
| 5,656,629 A | 8/1997 | Bacon et al. | |
| 5,789,394 A | 8/1998 | Nguyen-Ba et al. | |
| 5,846,749 A | 12/1998 | Slamon et al. | |
| 5,861,503 A | 1/1999 | Barrio et al. | |
| 5,917,042 A | 6/1999 | Daluge et al. | |
| 5,955,610 A | 9/1999 | Nguyen-Ba et al. | |
| 6,005,107 A | 12/1999 | Nguyen-Ba et al. | |
| 6,174,875 B1 | 1/2001 | Defranco et al. | |
| 6,210,974 B1 | 4/2001 | Gold et al. | |
| 6,262,254 B1 | 7/2001 | Barrio et al. | |
| 6,369,092 B1 | 4/2002 | Pamukcu et al. | |
| 6,444,656 B1 | 9/2002 | Nguyen-Ba et al. | |
| 2002/0156277 A1 | 10/2002 | Fick et al. | |
| 2002/0161014 A1 | 10/2002 | Sadhu et al. | |
| 2003/0022864 A1 | 1/2003 | Osjaq et al. | |
| 2003/0078413 A1 | 4/2003 | Dempcy | |
| 2004/0097526 A1 * | 5/2004 | Gillespie et al. .......... 514/261.1 |
| 2004/0102458 A1 | 5/2004 | Chiosis et al. | |
| 2005/0043239 A1 | 2/2005 | Douangpanya et al. | |
| 2005/0049263 A1 | 3/2005 | Kasibhatla et al. | |
| 2005/0107343 A1 | 5/2005 | Kasibhatla et al. | |
| 2005/0113340 A1 | 5/2005 | Kasibhatla et al. | |
| 2005/0119282 A1 | 6/2005 | Kasibhatla et al. | |
| 2006/0035909 A1 * | 2/2006 | Fuksova et al. .......... 514/261.1 |

FOREIGN PATENT DOCUMENTS

| | | | |
|---|---|---|---|
| EP | 55239 B1 | | 6/1982 |
| EP | 151528 A2 * | | 8/1985 |
| EP | 156559 B1 | | 10/1985 |

(Continued)

OTHER PUBLICATIONS

U.S. Appl. No. 60/128,593, Rosen et al.

(Continued)

*Primary Examiner*—Mark L. Berch
(74) *Attorney, Agent, or Firm*—Wilson, Sonsini, Goodrich & Rosati

(57) ABSTRACT

A compound represented by Formula I, or a polymorph, ester, tautomer, enantiomer, diastereomer, pharmaceutically acceptable salt or prodrug thereof,

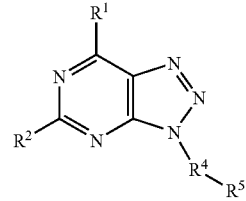

Formula I Wherein $R^1$ is halogen, —$OR^{11}$, —$SR^{11}$ or lower alkyl; $R^2$ is —$NHR^8$; $R^4$ is —$CHR^{12}$—, —C(O)—, —C(S)—, —S(O)— or —$S_2$—; and $R^5$ is aryl, heteroaryl, alicyclic, or heterocyclic, wherein the aryl group is substituted with 4 to 5 substituents, the heteroaryl group is substituted with 3 to 5 substituents, the alicyclic group is substituted with 3 to 5 substituents, and the heterocyclic group is substituted with 3 to 5 substituents.

21 Claims, No Drawings

FOREIGN PATENT DOCUMENTS

| | | |
|---|---|---|
| EP | 159264 B1 | 10/1985 |
| EP | 0178178 A2 | 4/1986 |
| EP | 178178 A2 | 4/1986 |
| EP | 0184322 A1 | 6/1986 |
| EP | 206415 B1 | 12/1986 |
| EP | 363320 A2 | 4/1990 |
| EP | 0151528 B1 | 7/1990 |
| EP | 465297 B1 | 1/1992 |
| EP | 502690 B1 | 9/1992 |
| EP | 565377 B1 | 10/1993 |
| EP | 675123 A1 | 10/1995 |
| JP | 10025294 | 1/1988 |
| JP | 06080670 A2 | 3/1994 |
| JP | 08041035 A2 | 2/1996 |
| JP | 08208687 A2 | 8/1996 |
| JP | 09020776 A2 | 1/1997 |
| JP | 09169758 2 | 6/1997 |
| JP | 2000-072773 A2 | 3/2000 |
| JP | 2003-113181 A2 | 4/2003 |
| WO | WO-1986-05518 A1 | 9/1986 |
| WO | WO-1995-07695 A1 | 3/1995 |
| WO | WO-1995-08327 A1 | 3/1995 |
| WO | WO-1998-01448 A1 | 1/1998 |
| WO | WO 98/51702 | 11/1998 |
| WO | WO-1999-01454 A1 | 1/1999 |
| WO | WO-1999-02162 A1 | 1/1999 |
| WO | WO-1999-12927 A1 | 3/1999 |
| WO | WO-1999-24432 A1 | 5/1999 |
| WO | WO-1999-32122 A1 | 7/1999 |
| WO | WO 99/51223 | 10/1999 |
| WO | WO 00/06523 | 2/2000 |
| WO | WO-2000-043394 A1 | 7/2000 |
| WO | WO-2000-044750 A1 | 8/2000 |
| WO | WO-2000-068230 A1 | 11/2000 |
| WO | WO-2001-38584 A2 | 5/2001 |
| WO | WO-2001-049688 A1 | 7/2001 |
| WO | WO 01/72779 | 10/2001 |
| WO | WO-2002-085905 A1 | 10/2001 |
| WO | WO-2001-081346 A2 | 11/2001 |
| WO | WO 02/02123 | 1/2002 |
| WO | WO 02/09696 | 2/2002 |
| WO | WO 02/36075 | 5/2002 |
| WO | WO 02/36171 | 5/2002 |
| WO | WO 02/055082 | 7/2002 |
| WO | WO 02/055083 | 7/2002 |
| WO | WO 02/055521 | 7/2002 |
| WO | WO-2002-055521 A1 | 7/2002 |
| WO | WO-2002-057288 A1 | 7/2002 |
| WO | WO 02/069900 | 9/2002 |
| WO | WO 02/094196 | 11/2002 |
| WO | WO-2002-088079 A2 | 11/2002 |
| WO | WO-2002-088080 A2 | 11/2002 |
| WO | WO-2002-102314 A2 | 12/2002 |
| WO | WO-2003-000200 A2 | 1/2003 |
| WO | WO-2003-002565 A1 | 1/2003 |
| WO | WO 03/026591 | 4/2003 |
| WO | WO 03/037860 | 5/2003 |
| WO | WO 03/041643 | 5/2003 |
| WO | WO-2003-035938 A2 | 5/2003 |
| WO | WO 03/050295 | 6/2003 |
| WO | WO 03/066005 | 8/2003 |
| WO | WO-2003-106458 A1 | 12/2003 |
| WO | WO-2004-014913 A2 | 2/2004 |
| WO | WO-2004-024082 A2 | 3/2004 |
| WO | WO-2004-029064 A1 | 4/2004 |
| WO | WO-2005-012324 A2 | 2/2005 |
| WO | WO-2005-016348 A1 | 2/2005 |
| WO | WO-2005-016349 A1 | 2/2005 |
| WO | WO-2005-028434 A2 | 3/2005 |

OTHER PUBLICATIONS

U.S. Appl. No. 60/293,246, Rosen et al.
U.S. Appl. No. 60/331,893, Zhang et al.
U.S. Appl. No. 60/335,391, Kasibhatla et al.
U.S. Appl. No. 60/337,919, Kasibhatla et al.
U.S. Appl. No. 60/340,762, Kamal et al.
U.S. Appl. No. 60/359,484, Nicchitta et al.
U.S. Appl. No. 60/371,668, Ulm et al.
Abblard, J. et al. "Preparation et determination de structure de nouvelles pyridines halogenees Mecanisme de l'halagenation" Bull. Soc. Chim. Fr. 1972, 2466.
Alhede, J. "A Simple and Efficient Synthesis of 9-Substituted Guanines. Cyclodesulfurization of 1-Substituted 5-[(Thiocarbamoyl)amino]imidazole-4-carboxamides under Aqueous Basic Conditions" Org. Chem., 1991, 2139.
Bennett, S. M., "Synthesis and Antiviral Activity of Some Acyclic and C-Acyclic Pyrrolo[2,3-d]pyrimidine Nucleoside Analogus" J. Med. 1990, 33, 2162.
Berge et al. "Pharmaceutical Salts", J. Pharm. Sci. 1977, 66:1-19.
Blanz, E. J., et al. "Carcinostatic Activity of Thiosemicarbazones of Formyl Heteroaromatic Compounds. VII. 2-Formylpyridine Derivatives Bearing Additional Ring Sustituents" J. Med. Chem. 1970, 13, 1124.
Buchner, J., "Hsp90 & Co.-a holding for folding," TIBS, Apr. 1999, 24:136-141.
Buchwald, Henry et al. "Long-term, continuous intravenous heparin administration by an implantable infusion pump in ambulatory patients with recurrent venous thrombosis" Surgery, 1980 88, 507.
Bundgaard, H. "Design and Application of Prodrugs" in A Textbook of Drug Design and Development, Krosgaard-Larsen and H. Bundgaard, Ed., 1991, Chapter 5, p. 113-191.
Bundgaard, H., Advanced Drug Delivery Review, 1992, 8, 1-38.
Caplan A., "Hsp90's secrets unfold: new insights from structural and functional studies," Trends in Cell Biol., 1999, 9:262-268.
Chem, J.W. et al. "Certain 8-Amino-9-(benzyl)guanines as potential purine nucleoside phosphorylase inhibitors" Eur. J. Med. Chem. 1994, 29(1), 3-9.
Chiosis et al., "A Small Molecule Designed to Bind to the Adenine Nucleotide Picket of HSP90 Causes HER2 Degradation and the Growth Arrest and Differentiation of Breast Cancer Cells," Chemistry & Biology, 8, pp. 289-299 (2001).
Chowdhury, Shafinaz F. et al. "Design, Synthesis, and Evaluation of Inhibitors of Trypanosomal and Leishmanial Dihtdrofolate Reductase" J. Med. Chem. 1999, 42, 4300.
Cory, A. et al. "Use of an aqueous soluble tetrazolium/formazan assay for cell growth assays in culture," Cancer Commun. 1991, 3, 207-212.
Dai et al., "Physical interaction of mammalian CDC37 with CDK4," J. Biol. Chem, 1996, 271:22030-22034.
De Cat, A. "Synthetic Applications of Difluorocarbene" et al. Bull. Soc. Chim. Belg. 1965, 74, 270-280.
De La Torre-Bueno, J., et al. Modern Pathology 2000, 13, 221A.
De Napoli, L., "Reaction of 3',5'-Di-O-acetyl-2'-deoxyinosine with the Chlorinating Agent PPh3-CCl4: Synthesis of the 6-chloroderivative and of a new base linked dimmer, useful intermediate to 15N-1-labelled 2'-deoxyinosine" J. chem.. Soc. Perkin Trans 1, 1994.
Erlichman, C., et al., "A Phase I Trial of 17-Allyl-Amino-Geldanamycin In Patients with Advanced Cancer," Proc. AACR (2001), 42, abstract 4474.
Fisher, B. E. et al. "The Structure of Isomaltol" J. Org. Chem. 1964, 29, 776.
Goodson, J. Max "Medical Applications of Controlled Release", 1984, vol. 2, pp. 115-138.
Grenert et al., "The amino-terminal domain of heat shock protein 90 (hsp90) that binds geldanamycin is an ATP/ADP switch domain that regulates hsp90 conformation," J. Biol. Chem., 1997, 272:23843-23850.

Jeromin, G. E. et al. "Seitenkettenchlorierungen von N-Heterocyclen mit Trichlorisocyanursaure (TCC)" Chem. Ber. 1987, 120, 649.

Abramovitch, "Pyridine and its derivatives" (Supplement, Part 2) Wiley & Sons, 1974, pp. 1-261.

Kozai, S. et al. "Synthesis and Biological Activity of 9-(2,6-Difluorobenzyl)-9H-purines Bearing Chlorine" Chem. Pharm. Bull., 1999, 47(4), 574-575.

Kurokawa, H. et al. "Inhibition of HER2/neu (erbB-2) and Mitogen-activated Protein Kinases Enhances Tamoxifen Action against HER2-overexpressing, Tamoxifen-resistant Breast Cancer Cells". Cancer Res. 2000, 60, 5887-5894.

Langer, Robert "New Methods of Drug Delivery" Science 1990, 249,1527-1533.

Lin, X., "Mild and Efficient Functionalization at C6 of Purine 2'-Deoxynucleosides and Ribonucleosides" Org. Letters, 2000, 2, 3497.

Looker, J. H. et al. "Bromomaltol: Structure Synthesis and Antiviral Activity of Some Acyclic and C-Acyclic Pyrrolo[2,3-d]pyrimidine Nucleoside Analogus".

Miller et al., "Depletion of the erbB-2 gene product p185 by benzoquinoid anasmycins", Cancer Res. 1994, 54:2724-2730.

Mimnaugh et al., "Polyubiquitination and proteasomal degradation of the p185c-erbB-2 receptor protein-tyrosine kinase induced by geldanamycin*," J. Biol. Chem., 1996, 271:22796-22801.

Mitchell MS, and Press M.F. "The Role of Immunohistochemistry and Fluorescence in Situ Hybridization for HER-2/neu in Assessing the Prognosis of Breast Cancer" Oncol., Suppl. 1999, 12, 108-116.

Morisawa, Y. et al. "Studies on Anticoccidial Agents. 1. Synthesis and Anticoccidial Activity of 4-Deoxypyridoxol and Its Esters" J. Med. Chem. 1974, 17, 1083, Muise-Heimericks et al., "Cyclin D expression is controlled post-transcriptionally via a phosphatidylinositol 3-kinase/Akt-dependent pathway*," J. Biol. Chem., 1998, 273(45):29864-29872.

Panaretou et al., "ATP binding and hydrolysis are essential to the function of the Hsp90 molecular chaperone in vivo," EMBO J., 1998, 17(16):4829-4836.

Parkanyi, Cyril et al. "Synthesis of Acyclic Nucleoside Analogs of 6-Substituted 2-Aminopurines and 2-Amino-8-azapurines" J. Het. Chem. 1990, 27(5), 1409.

Peterson, Mark L. et al. "Synthesis and Biological Evaluation of Carbocyclic Analgoues of Lyxofuranosides of 2-Amino-6-substituted-purines and 2-Amino-6-substituted-8-azapurines" J. Med. Chem., 1990, 33(4), 1214-19.

Prodromou, C. et al., "Identification and Structural Characterization of the ATP/ADP-Binding Site in the Hsp90 Molecular Chaperone" Cell, 90: 1997, 65-75.

Robins, M. J., "Nucleic Acid Related Compounds. 8. Direct Conversiono f 2'-Deoxyinosine to 6-Chloropurine 2'-Deoxyriboside and Sleceted 6-Substituted Deoxynucleosides and Their Evaluation As Substrates of Adenosine Deaminase" Can. J. Chem. 1973, 12, 3161.

Saudek et al. "A Preliminary Trial of the Programmable Implantable Medication System for Insulin Delivery" N. Engl. J. Med. 1989, 321, (574).

Scheibel et al., "The charged region of Hsp90 modulates the function of the N-terminal domain," Proc. Natl. Acad. Sci. USA, 1999, 96:1297-1302.

Schneider et al., "Pharmacologic shifting of a balance between protein refolding and degradation mediated by Hsp90," Proc. Natl. Acad. Sci. USA, 1996, 93:14536-14541.

Schnur et al., "Inhibition of the oncogene product p185 in vitro in vivo by geldanamycin and dihydrogeldanamycin deriviates", J. Med. Chem., 1995, 38:3806-3812.

Schulte et al., "Disruption of the Raf-1-Hsp90 molecular complex results in destabilization of Raf-1 and loss of Raf-1-Ras association" J. Biol. Chem, 1995, 270:24585-24588.

Schulte et al., "Geldanamycin-induced destabilization of Raf-1 involves the proteasome," Biochem. Biophys. Res. Commun., 1997, 239:655-659.

Seela, F., "7-Desaza-Isostere von 2'-Desoxyxanthosin und 2'-Desoxyspongosin—Synthese via Glycoslierung von 2,3-Dichlor-7H-pyrrolo[2,3-d] pyrmidin" Liebigs. Ann. Chem. 1985, 315.

Sefton Michael V. "Implantable Pumps", 1987, CRC Crit. Ref. Biomed. Eng. 14:201.

Segnitz et al., "The function of steroid hormone receptors is inhibited by the hsp90-specific compound geldanamycin", J. Biol. Chem., 1997, 272:18694-18701.

Sepp-Lorenzino et al., "Herbimycin A induces the 20 S proteasome- and Ubiquitin-dependent degradation of receptor tyrosine kinases" J. Biol. Chem., 1995, 270:16580-16587.

Smith et al., "Progesterone receptor structure and function altered by Geldanamycin, an hsp90-binding agent," Mol. Cell. Biol., 1995, 15:6804-6812.

Smith, E. M. "Pyridine-1-oxide in Pyridine and its Derivatives" in The Chemistry of Heterocyclic Compounds.

Stebbins et al., "Crystal structure of an Hsp90-geldanamycin complex; targeting of a protein chaperone by an antitumor agent," Cell, 1997, 89:239-250.

Stepanova et al., "Mammalian p50cdc37 is a protein kinase-targeting subunit of HSP90 that binds and stabilizes Cdk4," Genes Dev., 1996, 10:1491-1502.

Treat et al., Liposomes in the Therapy of Infectious Disease and Cancer, Lopez-Bernstein and Fidler, Ed., Liss, N.Y., pp. 353-365, 1989.

Ugarkar, B. G., "Adenosine Kinase Inhibitors. 1. Synthesis, Enzyme Inhibition, and Antiseizure Activity of 5-Iodotubercidin Analogues" J. Med. Chem. 2000, 43, 2883-2893.

Ugarkar, B. G., "Adenosine Kinase Inhibitors. 2. Synthesis, Enzyme Inhibition, and Antiseizure Activity of Diaryltubercidin Analogues" J. Med. Chem. 2000, 43, 2894-2905.

Vasilevskaya et al., "Effects of geldanamycin on signaling through activator-protein 1 in hypoxic HT29 human colon adenocarcinoma cells1," Cancer Res., 1999, 59:3935-3940.

Veliz, E. A., "C6 substitution of inosine using hexamethylphosphorous triamide in conjunction with carbon tetrahalide or N-halosuccinimide" Tetrahedron Lett, 2000, 41, 1695.

Weidmann, Klaus et al. "24 (2-Pyridylmethyl)sulfinyl-1H-thieno[3,4-d]imidazoles. A Novel Class of Gastric H+/K+-ATPase Inhibitors" J. Med. Chem. 1992, 35, 438.

Whitesell et al., "Inhibition of heat shock protein HSP90-pp69v-src heteroprotein complex formation by benzoquinone ansamycins: essential role for stress proteins in oncogenic transformation," Proc. Natl. Acad. Sci USA, 1994, 91:8324-8328.

Andricopulo, A.D. and Yunes, R.A., "Structure-activity relationships for a collection of structurally diverse inhibitors of purine nucleoside phosphorylase," Chem. & Pharm. Bull. 49(1), 10-17, (2001).

Ashton, W.T. et al., "Synthesis and Antiherpetic Activity of (±)-9-[[(Z)-2-(Hydroxymethyl)cyclopropryl]methyl]guanine and Related Compounds," J. Med. Chem. 1988, 31, 2304-2315.

Ashwell, M. et al., "An improved route to guanines substituted at N-9," J. of the Chem. Soc., Chem. Comm. (14), 955-6 (1990).

Baker, et al., "Irreversible Enzyme Inhibitors. XCV. 8-(m-Bromoacetamidobenzylthio) hypoxanthine, and Active-Site-Directed Irreversible Inhibitor of Xanthine Oxidase," J. Medicinal Chem. 10(4), 682-685 (1967).

Bakkestuen, A. K., et al., "9-Benzylpurines with inhibitory activity against Mycobacterium tuberculosis," Biorg. & Med. Chem. Ltrs., 10(11), 1207-1210 (2000).

Balo, M.C. et al, "Synthesis of novel carbocyclic nucleosides with a cyclopentenyl ring: homocarbovir and analogs," Tetrahedron 54(12), 2833-2842 (1998).

Balo, M.C. et al., "Synthesis and antiviral activies of some novel carbocyclic nucleosides," Nucleosides & Nucleotides 15(7&8), 1335-1346 (1996).

Bedard, J. et al., "Comparative study of the anti-human cytomegalovirus activities and toxicities of a tetrahydrofuran phosphonate analog of guanosine and cidofovir," Antimocrobial Agents & Chemo. 43(3), 557-567 (1999).

Bennett, L.L., et al., "Mode of action of 2-amino-6-chloro-1-deazapurine," Biochem. Pharmacol. 33(2), 261-71 (1984).

Blanco, J.M. et al., "Synthesis and antiviral and antineoplastic activities of some novel carbocyclic guanosine analogs with a cyclobutane ring," Chem. & Pharm. Bulletin, 47(9), 1314-1317, (1999).

Blanco, J.M. et al., "Synthesis and antiviral and cytostatic activities of carbocyclic nucleosides incorporating a modified cyclopentane ring. 1. Guanosine analogs.," Nucleosides & Nucleotides 16(1&2), 159-171 (1997).

Brathe, A. et al., "Cytotoxic activity of 6-alkynyl-and 6-alkenylpurines," Biorg. & Med. Chem. Ltrs. 13(5), 877-880 (2003).

Bruckner, A.M. et al, "Nucleo-β-amino acids: synthesis and oligomerization to β-homoalanyl-PNA," Helvetica Chimica Acta 85(11), 3855-3866 (2002).

Bubenik, M. et al., "A stereoselective route to bioactive nucleotide phosphonate analogs," Tetrahedron Ltrs. 44(45), 8261-8263 (2003).

Bubenik, M. et al., "Novel nucleotide phosphonate analogues with potent antitumor activity," Biorg. & Med. Chem. Ltrs. 12(21), 3063-3066 (2002).

Burger, A. et al., "Synthesis of 8-(O-Hydroxyalkyl)-, 8-(o-Hydroxyalk-1-enyl)-, and 8-(o-Hydroxyalk-1-ynyl)adenines Using the tert-Butyldimethylsilyloxymethyl Group, a New and Versatile Protecting Group of Adenine," J. Org. Chem. 2000, 65, 7825-7832.

Caamano, O. et al, "Carbocyclic nucleosides with a modified cyclopentane skeleton," Nucleosides & Nucleotides 14(3-5), 295-7 (1995).

Cesnek, M. et al., "New 2-alkynyl derivatives of the acyclic nucleoside 9-(2,3-dihydroxypropyl)adenine and their 6-guanidinopurine counterparts as potential effectors of adenosine receptors," Collection of Czechoslovak Chem. Comm. 68(11), 2201-2218 (2003).

Cheng, C.C. et al., "Rearrangement of 4-Amino-6-chloro-1-methylpyrazolo (3,4-d)pyrimidine in Basic Solution," J. Org. Chem. 1959, vol. 24, pp. 1570-1571.

Choi, B.G. et al, "Synthesis and antiviral activity of novel exomethylene cyclopropyl nucleosides," Nucleosides, Nucleotides & Nucleic Acids 20(4-7), 1059-1062 (2001).

Deng, H.F., "Study on the synthesis of N6 aromatic heterocyclic methyl substituted adenosine and adenine by Dimroth rearrangement reaction,"Chinese Chem. Ltrs. 5(4), 271-4 (1994).

Erion, M.D. et al., Structure-based design of inhibitors of purine nucleoside phophorylase.3. 9-arylmethyl derivatives of 9-deazaguanine substituted on the arylmethyl group. J. of Med. Chem. 37(7), 1034 (1994).

Erion, M.D. et al., "Structure-Based Design of Inhibitors of Purine Nucleoside Phosphorylase. 3. 9-Arylmethyl Derivatives of 9-Deazaguanine Substituted on the Methylene Group," J. Med. Chem. 1993, 36, 3771-3783.

Gangjee et al., "Design, Synthesis and X-ray Crystal Structure of a Potent Dual Inhibitor of Thymidylate Synthase and Dihydrofolate Reductase as an Antitumor Agent," J. Am. Chem. Soc. 2000, vol. 43, No. 21, pp. 3837-3851.

Guan, H. et al., "Synthesis of phosphonate derivatives of methylenecyclopropane nucleoside analogues by alkylatin-elimination method and unusual opening of cyclopropane ring," Tetrahedron 58(30), 6047-6059 (2002).

Guillarme et al., "Rapid Access to acyclic nucleosides via conjugate addition," Tetrahedron, 59:12, Mar. 17, 2003, pp. 2177-2184.

Halazy, S. et al., "Fluorophosphonate derivatives of N9-benzylguanine as potent, slow-binding multisubstrate analog inhibitors of purine nucleoside phosphorylase," Tetrahedron, 52(1), 177-84 (1996).

Halazy, S. et al., "Phosphonate derivatives of N9-benzylguanine: a new class of potent purine nucleoside phosphorylase inhibitors," Biorg. & Med. Chem. Ltrs. 2(5), 407-10 (1992).

Halbfinger, E. et al., "Molecular Recognition of Modified Nucleotides by the P2Y1-Receptor. 1. A Synthetic, Biochemical, and NMR Approach," J. Med. Chem. 1999, 42, 5325-5337.

Han, M.J. et al., "Polynucleotide analogs. VI. Synthesis and characterization of alternating copolymers of maleic anhydride and dihydropyran-containing guanine derivatives," J. of Polymer Science, Part A: Polymer Chemistry 33(11), 1829-39 (1995).

Herdedwijn, P. et al., "Synthesis and Structure-Activity Relationships o Analogs of 2'-Deoxy-2'-(3-mehoxybenzamido)adenosine, a Selective Inhibitor of Trypanosomal Glycosomal lyceraldehyde-3-phosphate Dehydrogenase," J. Med. Chem. 1995, 38, 3838-3849.

Holy, A. et al., "Structure-Antiviral Activity Relationship in the Series of Pyrimidine and Purine N-[2-(2-Phosphonomethoxy))ethyl] Nucleotide Analogues. 1. Derivatives Substituted at the Carbon Atoms of the Base," J. Med. Chem. 1999, 42, 2064-2086.

Holy, A. et al., "Acyclic nucleotide analogs. VI. Synthesis of (3-hydroxy-2-phosphonylmethoxypropyl) derivatives of heterocyclic bases," Collection of Czechoslovak Chemical Communications 54(9), 2470-501 (1989).

Hossain, N. et al., "Synthesis of homo-N-nucleosides, a series of C1' branched-chain nucleosides," Tetrahedron 52(15), 5563-78 (1996).

Hotoda, H. et al., "Biologically active oligodeoxyribonucleotides. X. Anti-HIV-1 activity and stability of modified hexanucleotides containing glycerl-skeleton," Nucleosides & Nucleotides 17(1-3), 243-252 (1998).

Houlton, A. et al, "Synthesis, structure and redox properties of ferrocenylmethylnucleobases," J. of the Chem Society, Dalton Transactions: Inorganic Chem. 1999, 18, 3229-3234.

Jacobson, K. A. et al., "Structure-Activity Relationships of Bisphosphate Nucleotide Derivatives as P2Y, Receptor Antanonists and Partial Agonists," J. Med. Chem. 1999, 42, 1625-1638.

Janeba, Z., Collection of Czechoslovak Chemical Communications 66(9), 1393-1406 (Sep. 2001).

Kanth et al., "Selective Reduction of Carboxylic Acids into Alcohols Using NaBH4 and I2", J. Org. Chem. 1991, 56, 5964-5965.

Kelley, J.L. et al., "6-(Alkylamino)-9-alkylpurines. A New Class of Potential Antipsychotic Agents," J. Med. Chem. 1997, 40, 3207-3216.

Kelley, J.L. et al., "9-[Phosphonoalkyl)benzyl]guanines. Multisubstrate Analogue Inhibitors of Human Erythrocyte Purine Nucleoside Phosphorylase," J. Med. Chem. 1993, 36, 3455-3463.

Kelley, J.L. et al., "Synthesis and Structure-Activity Relationships of 2-Substituted-6-(dimethylamino)-9-(4-methylbenzyl)-9H-purines with Antirhinovirus Activity," J. Med. Chem. 1989, 32, 218-224.

Kim, K. and McComas, W., "Chemoselective high-throughput purification mediated by solid-supported reagents: Its application to the first 6,9-disubstituted purine library synthesis," Cominatorial Chem. & High Throughput Screening, 3(2), 125-129 (2000).

Kim, D.K., et al., "Synthesis and evaluation of 2-amino-6-fluoro-9-(2-hydroxyethoxymethyl)purine esters as potential prodrugs of acyclovir," Bioorg. Med. Chem. 6(12), 2525-30 (1998).

Kjellberg, J. and Johansson, N.G., "Studies on the Alkylation of Derivatives of Guanine," Nucelosides & Nucleotides, 8(2), 225-256 (1989).

Kjellberg, J. and Johansson, N.G., "Characterization of N-7 and N-9 alkylated purines analogs by proton and carbon-13 NMR," Tetrahydron 42(23), 6541-44 (1985).

Kos et al., "Deamination of 6-Amino-and-6-(Alkylamino)-9-alkylpurines and Demethylation of Methylthiopurines by Sodium in Liquid Ammonia," J. Org. Chem. 1981, 46, 5000-5003.

Kotra, L.P. et al., "Structure-Activity Relationships of 2'-Deoxy-2',2'-difluoro-1-erythro-pentofuranosyl Nucleosides," J. Med. Chem. 40, 3635-3644 (1997).

Kusmierek, J.T. et al., "Preparative electrochemical reduction of 2-amino-6-chloropurine and synthesis of 6-deoxyacyclovir, a fluorescent substrate of xanthine oxidase and a prodrug of acyclovir," Acta Chem Scan B 41(10), 701-7 (1987).

Kwak, E.Y. et al, "Synthesis and antiviral activity of novel methylene cyclopropyl nucleosides," Archives of Pharm. Res. 23(6), 559-563 (2000).

Langli, G. et al., "Regiochemistry in Stille couplings in 2,6-dihalopurines," Tetrahedron, 52(15), 5625-38 (1996).

Lee, Y.R. et al., "Design and synthesis of novel fluorocyclopropanoid nucleosides," Nucleosides, Nucleotides & Nucleic Acids 20(4-7), 677-679 (2001).

Legraverend, M. et al., "Synthesis and in vitro evaluation of novel 2,6,9-trisubstituted purines acting as cyclin-dependent kinase inhibitors," Biorg. & Med. Chem. 7(7), 1281-1293 (1999).

Linn, J.A. et al., "1,4-Diazabicyclo[2.2.2.]octane (DABCO)-catalyzed hydrolysis and alcoholysis reactions of 2-amino-9-benzyl-6-chloro-9H-purine," J. of the Chem. Soc., Chem. Comm. (8), 913-914 (1994).

Liu, F. et al., "Addition and cycloaddition to 2-and 8-vinylpurines," Acta CXhemica Scandinavica, 53(4), 269-279 (1999).

Mallory et al., "Pyrimido[4,5-c]pyridazines. 3. Preferential formation of 8-amino-1H-pyrimido[4,5-c]-1,2-diazepin-6(7H)-ones by cyclizations with .alpha., .gamma..- dioxoesters," J. Org. Chem. 1982, vol. 47, pp. 667-674.

Meegalla, S. et al., "Synthesis of 1-quinolyl derivatives of adenine and guanine," Synlett (1), 61-2 (1993).

Montgomery, J.A. et al., "Synthesis of potential anticancer agents. XXX. (1-Aziridinyl)purines," J. of Med. & Pharm. Chem. 5, 15-24 (1962).

Murthy, D. et al., "9-[(Hydroxymethylphenyl_methyl]purine nucleoside analogues: Synthesis, antiviral and cytotoxic properties against cancer cells," Med. Chem. Res. 12(1), 13-25 (2003).

Nguyen-Ba, P. et al., "Design and SAR study of a novel class of nucleoside analogues as potent anti-HCMV agents," Nucleosides & Nucleotides 18(4&5), 821-827 (1999).

Nguyen-Ba, P. et al., "Identification of novel nucleotide phosphonate analogs with potent anti-HCMV activity," Bioorg. & Med. Chem. Ltrs. 8(24), 3561-3566 (1998).

Nguyen-Ba, P. et al., "Design and synthesis of a novel class of nucleotide analogs with anti-HCMV activity," Bioorg. & Med. Chem. Ltrs. 8(24), 3555-3560 (1998).

Noell, C.W. et al., "Potential Purine Antagonists. XX. The Preparation and Reactions of Some Methylthiopurines," J. Am. Chem. Soc. 81, 5997-6007 (1959).

Novak, J. et al., "Synthesis of 7-Hydroxy(phenyl)ethylguanines by Alkylation of 2-amino-6-chloropurine with allyl-protected bromohydrins," Org. Ltrs. 5(5), 637-639 (2003).

Onishi, T. and Tsuji, T., "Synthesis of cyclobutane analogs of the antiviral cyclopropane nucleoside A-5021," Nucleosides, Nucleotides & Nucleic Acids 20(12), 1941-1948 (2001).

Onishi, T. et al., "A practical synthesis of antiviral cyclopropane nucleoside A-5021," Tetrahedron Ltrs. 40(50), 8845-8847 (1999).

Ozeki, N. et al., "A New Sandmeyer Iodination of 2-Aminopurines in Non-Aqueous Conditions: Combination of Alkali Metal Iodide and Iodine as Iodine Sources," Heterocycles, vol. 55, No. 3, pp. 461-464, 2001.

Panouse, J.J.., Pharma. Francaises 2000, 58(5), 291-302.

Press, M. et al., Modern Pathology 2000, 13 225A.

Park, J. et al., "Synthesis of [1'-fluoro-2',2'-bis-(hydroxymethyl)-cyclopropylmethyl]purines as antiviral agents," Nucleosides, Nucleotides & Nucleic Acids 22(5-8), 955-957 (2003).

Pierra, C. et al., "Synthesis and antiviral activities of enantiomeric 1-[2-(hydroxymethyl)cyclopropyl] methyl nucleosides," Nucleosides, Nucleotides & Nucleic Acids 19 (1&2), 253-268 (2000).

Quintela et al., "Pyrazolopyrimidines: synthesis, effect on histamine release from rat peritoneal mast cells and cytotoxic activity," Eur. J. Med. Chem. 2001, vol. 36, pp. 321-332.

Qiu, Y. and Zemlicka, J., "Synthesis of new nucleoside analogues comprising a geminal difluorocyclopropane moiety as potential antiviral/antitumor agents," Nucleosides & Nucleotides 18(10), 2285-2300 (1999).

Raboisson, P. et al., "Design, synthesis and structure-activity relationships of a series of 9-substituted adenine derivatives as selective phosphodiesterase type-4 inhibitors," Eur. J. of Medicinal Chem. 38 (2003) 199-214.

Santana, L. et al., "Synthesis of 1,2-disubstituted carbocyclic analogs of pyrimidine and purine nucleosides," Synthesis 10, 1532-1538 (2001).

Santana, L. et al., "Synthesis and biological activity of some 2-aminopurine carbonucleosides," Nucleosides & Nucleotides 16(7-9), 1337-1339 (1997).

Sedlak, M. et al., "Synthesis and $^{15}$N NMR Characterization of 4-Vinylbenzyl Substituted Bases of Nucleic Acids," J. Heterocyclic Chem. 40, 671-675 (2003).

Sekiyama, T. et al., "Synthesis and Antiviral Activity of Novel Acyclic Nucleosides: Discovery of a Cyclopropyl Nucleoside with Potent Inhibitory Activity against Herpesviruses," J. Med. Chem. 1998, 41, 1284-1298.

Sen, A.K. et al., "Synthesis of compounds related to 4(5)-aminoimidazole-5(4)-carboxamides: part VI—synthesis of 3-(6-methoxyl-8-quinolyl)-7-methylpurin-6(3H)-one," Indian J. of Chem. Sect. B: Org. Chem. Including Medicinal Chem. 23B(9), 870-3 (1984).

Shealy, Y.F. et al., "Synthesis and antiviral evaluation of carbocyclic analogues of 2-amino-6-substituted-purine 3'-deoxyribofuranosides," J. Med. Chem. 30(6), 1090-4 (1987).

Shealy, Y.F. et al., "Synthesis and antiviral evaluation of carbocyclic analogues of ribofuranosides of 2-amino-6-substituted-purines and of 2-amino-t-substituted-8-azapurines," J. Med. Chem., 27(5), 670-4 (1984).

Sircar, J.C., "8-amino-9-substituted guanines: potent purine nucleoside phosphorylase (PNP) inhibitors," Agents and Actions 21 (3-4), 253-6 (1987).

Terry, B.J. et al., "Broad-spectrum antiviral activity of the acyclic guanosine phosphonate (R,S)-HPMPG," Antiviral Res. 10(4-5), 235-51 (1988).

Tohidi, M. and Orgel, L.E., "Some acyclic analogs of nucleotides and their template-directed reactions," J. of Mol. Evolution 28(5), 367-373 (1989).

Toyota, A. et al., "Synthesis of nucleosides and related compounds. 31. The alkylation of 2-amino-6-chloropurines with alcohols by Minsunobu reaction for a synthesis of carbocyclic guanosine analogs," Heterocycles 36(7), 1625-30 (1993).

Van Calenbergh et al., "Synthesis and Structure-Activity Relationships of Analogs of 2'-Deoxy-2'-(3-methoxybenzamido)adenosine, a Selective Inhibitor of Trypanosomal Glycosomal Glyceraldehyde-3-phosphate Dehydrogensase," J. Med. Chem. 1995, 38, 3838-3849, 1995.

Wang, R. et al., "Synthesis of methylenecyclobutane analogues of nucleosides with axial chirality and their phosphoralaninates: A new pronucleotide effective against Epstein-Barr virus," Antiviral Chem. & Chemo. 13(4), 251-262 (2002).

Wang, R. et al., "Methylene-*gem*-Difluorocyclopropane Analogues of Nucleosides: Synthesis, Cyclopropene-Methylenecyclopropane Rearrangment, and Biological Acitivity," J. Med. Chem. 2001, 44, 4019-4022.

Wong, C. et al., "Synthesis and Evaluation of HomoazaSugars as Glycosidase Inhibitors," J. Org. Chem. 1995, 60, 1492-1501.

Yokomatsu, T. et al., "Synthesis of 1,1-difluoro-5-(1H-9-purinyl)-2-pentenylphosphonic acids and the related methano analoges. Remarkable effect of the nucleobases and the cyclopropane rings on inhibitory activity toward purine nucleoside phosphorylase," Biorg. & Med. Chem. 6(12), 2495-2505 (1998).

Yokomatsu, T. et al., "Synthesis of (2'S,3'S)-9-(4-phosphono-4',4'-difluoro-2',3'-methanobutyl)guanine and its enantiomer. Evaluation of the inhibitory activity for purine nucleoside phosphorylase," Tetrahedron 53(33), 11297-11306(1997).

Zemlicka, J., "Synthesis and biological properties of 9-(2,4-dihydroxybutyl)adenine and guanine: new analogs of 9-(2,3-dihydroxypropyl)adenine (DHPA) and 9-(2-hydroxyethoxymethyl)guanine (acyclovir)," Nucleosides & Nucleotides 3(3), 245-64 (1984).

Zheng, Q. et al., "Synthesis and preliminary biological evaluation of radiolabeled O6-benzylguanine derivatives, new potential PET imaging agents for the DNA repair protein )6-alkylguanine-DNA alkyltransferase in breast cancer," Nucl. Med. & Biol., 30(4), 405-415 (2003).

Zheng, Q. et al., "Synthesis of radiolabeled $O^6$-benzylguanine derivatives as new potential PET tumor imaging agents for the DNA repair protein $O^6$-alkylguanine-DNA alkyltransferase," J. Label Compd. Radiopharm. 2002;45:1239-1252.

* cited by examiner

TRIAZOLOPYRIMIDINES AND RELATED ANALOGS AS HSP90-INHIBITORS

This application relates and claims priority to U.S. Provisional Application Ser. No. 60/504,135, filed Sep. 18, 2003 and U.S. Provisional Application Ser. No. 60/591,467, filed Jul. 26, 2004.

This application also relates to three other U.S. Utility applications Ser. No. 10/946,645 filed Sep. 20, 2004 (now Publication No. 20050113340; Ser. No. 10/946,637 filed Sep. 20, 2004 (now Publication No. 2005-119282) and Ser. No. 10/945,851 filed Sep. 20, 2004 (now Publication No. 20050107343. This application further relates to International Application PCT/US02/35069, filed Oct. 30, 2002, (now Publication No. WO03/37860). All the above cited U.S. utility applications, provisional applications and international application are expressly incorporated herein by reference in their entirety.

FIELD OF THE INVENTION

The invention relates in general to triazolopyrimidines and their related analogs and their broad-spectrum utility, e.g., in inhibiting heat shock protein 90 (HSP90) to thereby treat or prevent HSP90-mediated diseases.

BACKGROUND

HSP90s are ubiquitous chaperone proteins that are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner J. *TIBS* 1999, 24, 136–141; Stepanova, L. et al. *Genes Dev.* 1996, 10, 1491–502; Dai, K. et al. *J. Biol. Chem.* 1996, 271, 22030–4). Studies further indicate that certain co-chaperones, e.g., HSP70, p60/Hop/Sti1, Hip, Bag1, HSP40/Hdj2/Hsj 1, immunophilins, p23, and p50, may assist HSP90 in its function (see, e.g., Caplan, A. *Trends in Cell Biol.* 1999, 9, 262–68).

Ansamycin antibiotics, e.g., herbimycin A (HA), geldanamycin (GM), and 17-allylaminogeldanamycin (17-AAG) are thought to exert their anticancerous effects by tight binding of the N-terminus pocket of HSP90, thereby destabilizing substrates that normally interact with HSP90 (Stebbins, C. et al. *Cell* 1997, 89, 239–250). This pocket is highly conserved and has weak homology to the ATP-binding site of DNA gyrase (Stebbins, C. et al., supra; Grenert, J. P. et al. *J. Biol. Chem.* 1997, 272, 23843–50). Further, ATP and ADP have both been shown to bind this pocket with low affinity and to have weak ATPase activity (Proromou, C. et al. *Cell* 1997, 90, 65–75; Panaretou, B. et al. *EMBO J.* 1998, 17, 4829–36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T. H. et al. *Proc. Natl. Acad. Sci. USA* 1999, 96, 1297–302; Schulte, T. W. et al. *J. Biol. Chem.* 1995, 270, 24585–8; Whitesell, L., et al. *Proc. Natl. Acad. Sci. USA* 1994, 91, 8324–8328). Ansamycins have also been demonstrated to inhibit the ATP-dependent release of chaperone-associated protein substrates (Schneider, C. L. et al. *Proc. Natl. Acad. Sci., USA* 1996, 93, 14536–41; Sepp-Lorenzino et al. *J. Biol. Chem.* 1995, 270, 16580–16587). In either event, the substrates are degraded by a ubiquitin-dependent process in the proteasome (Schneider, C. L., supra; Sepp-Lorenzino, L., et al. *J. Biol. Chem.* 1995, 270, 16580–16587; Whitesell, L. et al. *Proc. Natl. Acad. Sci. USA* 1994, 91, 8324–8328).

HSP90 substrate destabilization occurs in tumor and non-transformed cells alike and has been shown to be especially effective on a subset of signaling regulators, e.g., Raf (Schulte, T. W. et al. *Biochem. Biophys. Res. Commun.* 1997, 239, 655–9; Schulte, T. W., et al. *J. Biol. Chem.* 1995, 270, 24585–8), nuclear steroid receptors (Segnitz, B.; U. Gehring *J. Biol. Chem.* 1997, 272, 18694–18701; Smith, D. F. et al. *Mol. Cell. Biol.* 1995, 15, 6804–12), v-Src (Whitesell, L., et al. *Proc. Natl. Acad. Sci. USA* 1994, 91, 8324–8328) and certain transmembrane tyrosine kinases (Sepp-Lorenzino, L. et al. *J. Biol. Chem.* 1995, 270, 16580–16587) such as EGF receptor (EGFR) and HER2/Neu (Hartmann, F., et al. *Int. J. Cancer* 1997, 70, 221–9; Miller, P. et al. *Cancer Res.* 1994, 54, 2724–2730; Mimnaugh, E. G., et al. *J. Biol. Chem.* 1996, 271, 22796–801; Schnur, R. et al. *J Med Chem.* 1995, 38, 3806–3812), CDK4, and mutant p53. Erlichman et al. *Proc. AACR* 2001, 42, abstract 4474. The ansamycin-induced loss of these proteins leads to the selective disruption of certain regulatory pathways and results in growth arrest at specific phases of the cell cycle (Muise-Heimericks, R. C. et al. *J. Biol. Chem.* 1998, 273, 29864–72), and apoptosis, and/or differentiation of cells so treated (Vasilevskaya, A. et al. *Cancer Res.,* 1999, 59, 3935–40). Ansamycins thus hold great promise for the treatment and/or prevention of many types of cancers and proliferative disorders, and also hold promise as traditional antibiotics. However, their relative insolubility makes them difficult to formulate and administer, and they are not easily synthesized and currently must, at least in part, be generated through fermentation. Further, the dose limiting toxicity of ansamycins is hepatic.

In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating stroke, ischemia, multiple sclerosis, cardiac disorders, central nervous system related disorders and agents useful in promoting nerve regeneration (See, e.g., Rosen et al. WO 02/09696 (PCT/US01/23640); Degranco et al. WO 99/51223 (PCT/US99/07242); Gold, U.S. Pat. No. 6,210,974 B1; DeFranco et al., U.S. Pat. No. 6,174,875. Overlapping somewhat with the above, there are reports in the literature that fibrogenetic disorders including but not limited to scleroderma, polymyositis, systemic lupus, rheumatoid arthritis, liver cirrhosis, keloid formation, interstitial nephritis, and pulmonary fibrosis also may be treatable with HSP90 inhibitors. Strehlow, WO 02/02123 (PCT/US01/20578). Still further HSP90 modulation, modulators and uses thereof are reported in Application Nos. PCT/US03/04283, PCT/US02/35938, PCT/US02/16287, PCT/US02/06518, PCT/US98/09805, PCT/US00/09512, PCT/US01/09512, PCT/US01/23640, PCT/US01/46303, PCT/US01/46304, PCT/US02/06518, PCT/US02/29715, PCT/US02/35069, PCT/US02/35938, PCT/US02/39993, 60/293,246, 60/371,668, 60/335,391, 60/128,593, 60/337,919, 60/340,762, 60/359,484 and 60/331,893.

Recently, purine derivatives showing HSP90 inhibitory activity have been reported, e.g., in PCT/US02/35069; PCT/US02/36075. Purine moieties are well accepted bioisosteres for a variety of ATP-dependent molecular targets, see, JP 10025294; U.S. Pat. No. 4,748,177; U.S. Pat. No. 4,772,606;

U.S. Pat. No. 6,369,092; WO 00/06573; WO 02/055521; WO 02/055082; WO 02/055083; European Patent 0178178; Eur. J. Med. Chem. 1994, 29(1), 3–9; and J Het. Chem. 1990, 27(5), 1409. However, compounds having the desired potency, selectivity and pharmaceutical properties required for effective HSP90 inhibition in vivo have not been reported. Therefore, a need remains for additional novel and potent HSP90 inhibitors that meet the demanding biological and pharmaceutical criteria required to proceed towards human clinical trials.

SUMMARY OF THE INVENTION

The present invention is directed towards heterocyclic compounds, in particular towards triazolopyrimidines and related compounds that show broad utility, e.g., in inhibiting HSP90 and treating and/or preventing diseases that are HSP90-dependent.

In one aspect, the invention comprises the heterocyclic compounds as specified below in Formulae A and I and compounds that are produced by a synthetic process of the invention. Also included in the scope of the present invention are stereoisomeric forms, including the individual enantiomers and diastereomers, racemic mixtures, and diastereomeric mixtures, as well as polymorphs, solvates, esters, tautomers, pharmaceutically acceptable salts and prodrugs of these compounds. Stereoisomers of the compounds of the present invention may be isolated by standard resolution techniques such as, for example, fractional crystallization and chiral column chromatography.

In one embodiment, the invention provides compounds of Formula A, or a polymorph, solvate, ester, tautomer, diastereomer, enantiomer, pharmaceutically acceptable salt or prodrug thereof, which show utility by inhibiting HSP90 and treating and/or preventing diseases that are HSP90-dependent.

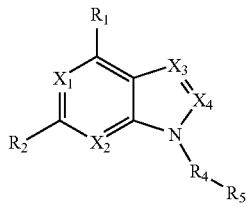

A wherein:
  $X^1$ and $X^2$ are the same or different and each is nitrogen or —$CR^6$;
  $X^3$ is nitrogen or —$CR^3$ wherein $R^3$ is hydrogen, OH, a keto tautomer, —$OR^8$, —CN, halogen, lower alkyl, or —$C(O)R^9$;
  $X^4$ is nitrogen or —$CR^6$ when $X^3$ is nitrogen, and $X^4$ is —$CR^6R^7$ when $X^3$ is —$CR^3$;
  $R^1$ is halogen, —$OR^8$, —$SR^8$, or lower alkyl;
  $R^2$ is —$NR^8R^{10}$;
  $R^4$ is —$(CH_2)_n$— wherein n=0–3, —C(O), —C(S), —$SO_2$—, or —$SO_2N$—; and
  $R^5$ is alkyl, aromatic, heteroaromatic, alicyclic, or heterocyclic, each of which is optionally bi- or tri-cyclic, and optionally substituted with H, halogen, lower alkyl, lower alkenyl, lower alkynyl, lower aryl, lower alicyclic, aralkyl, aryloxyalkyl, alkoxyalkyl, perhaloalkyl, perhaloalkyloxy, perhaloacyl, —$N_3$, —$SR^8$, —$OR^8$, —CN, —$CO_2R^9$, —$NO_2$, or —$NR^8R^{10}$.

In certain embodiments, there are exclusionary provisos with respect to compounds disclosed in JP 10025294; U.S. Pat. No. 4,748,177; U.S. Pat. No. 4,748,177; U.S. Pat. No. 6,369,092; WO 00/06573; WO 02/055521; WO 02/055082; WO 02/055083; Eur. J. Med. Chem. 1994, 29(1), 3–9; and J. Het. Chem. 1990, 27(5), 1409, which disclose compounds with —$R^4R^5$ comprising ribose or a derivative thereof, or a sugar or derivative thereof; and compounds where —$R^4R^5$ is a phosphonate or phosphonic acid, or is substituted with a phosphonate or phosphonic acid; or compounds where $R^4$ is —$CH_2$— or —$(CH_2)_n$— that are connected through an oxygen atom to another group.

In another embodiment, the invention provides compounds of Formula I, or a polymorph, solvate, ester, tautomer, diastereomer, enantiomer, pharmaceutically acceptable salt or prodrug thereof, which show utility for inhibiting HSP90 and treating and/or preventing diseases that are HSP90-dependent,

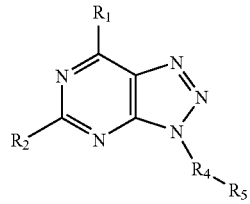

Formula I wherein:
  $R^1$ is halogen, —$OR^{11}$, —$SR^{11}$ or lower alkyl;
  $R^2$ is —$NHR^8$;
  $R^4$ is $CHR^{12}$—, —C(O)—, —C(S)—, —S(O)— or —$SO_2$—;
  $R^5$ is aryl, heteroaryl, alicyclic, or heterocyclic, wherein:
    the aryl group is substituted with 3 to 5 substituents,
    the heteroaryl group is substituted with 2 to 5 substituents,
    the alicyclic group is substituted with 3 to 5 substituents,
    the heterocyclic group is substituted with 3 to 5 substituents, and
    the substituents are selected from the group consisting of halogen, lower alkyl, lower alkenyl, lower alkynyl, —$SR^8$, —$OR^8$, —CN, —C(O)OH, —$C(O)R^9$, —$NO_2$, —$NR^8R^{10}$ lower aryl, heteroaryl, alicyclic, lower heterocyclic, arylalkyl, heteroarylalkyl, amino, alkylamino, dialkylamino, oxo, perhaloalkyl, perhaloalkoxy, perhaloacyl, guanidinyl, pyridinyl, thiophenyl, furanyl, indolyl, and indazolyl, wherein $R^8$ and $R^{10}$ taken together with the N to which they are attached optionally form a ring of 3–7 ring atoms and 1–3 of the ring atoms are heteroatoms selected from the group of O, S and N;
  $R^8$ is hydrogen, lower alkyl, lower alkenyl, lower alkynyl, lower aryl, lower heteroaryl, or —$C(O)R^9$;
  $R^9$ is H, lower alkyl, lower alkenyl, lower alkynyl, lower aryl, lower heteroaryl, —$NR^{10}R^{10}$, or —$OR^{11}$, wherein $R^{10}$ and $R^{10}$ taken together optionally form a ring of 3–7 ring atoms and optionally 1–3 of the ring atoms are heteroatoms selected from the group of O, S and N;
  $R^{10}$ is hydrogen, lower alkyl, lower heteroaryl, lower aryl, lower alkenyl, or lower alkynyl, $R^{11}$ is lower alkyl, lower alkenyl, lower alkynyl, lower heteroaryl or lower aryl; and $R^{12}$ is hydrogen or lower alkyl;

provided that when $R^5$ is alicyclic, the ring system does not contain any tetra-substituted sp$^3$ ring carbons.

In another embodiment, the invention provides compounds, or a polymorph, solvate, ester, tautomer, diastereomer, enantiomer, pharmaceutically acceptable salt or prodrug thereof, which show utility for inhibiting HSP90 and treating and/or preventing diseases that are HSP90-dependent, that are prepared by the process comprising:

reacting a compound of formula Y and a compound of formula Z, wherein:

Y is a represented by any one of the following formulae:

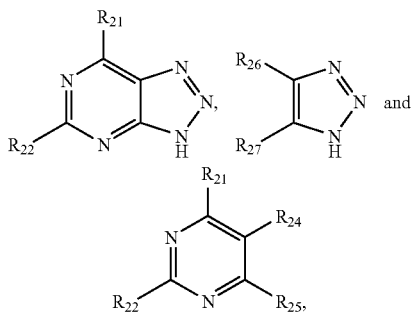

Z is L$^1$—R$^4$—R$^5$; wherein:

L$^1$ is halogen, NR$^8$R$^{10}$ triflate, tosylate, or mesylate;

R$^4$ is —CHR$^{12}$—, —C(O)—, —C(S)—, —S(O)— or —SO$_2$—;

R$^5$ is aryl, heteroaryl, alicyclic, or heterocyclic, wherein:

the aryl group is substituted with 3 to 5 substituents, the heteroaryl group is substituted with 2 to 5 substituents, the alicyclic group is substituted with 3 to 5 substituents, the heterocyclic group is substituted with 3 to 5 substituents, and the substituents are selected from the group consisting of halogen, lower alkyl, lower alkenyl, lower alkynyl, —SR$^8$, —OR$^8$, —CN, —C(O)OH, —C(O)R$^9$, —NO$_2$, —NR$^8$R$^{10}$, lower aryl, heteroaryl, alicyclic, lower heterocyclic, arylalkyl, heteroarylalkyl, amino, alkylamino, dialkylamino, oxo, perhaloalkyl, perhaloalkoxy, perhaloacyl,] guanidinyl, pyridinyl, thiophenyl, furanyl, indolyl, and indazolyl, wherein R$^8$ and R$^{10}$ taken together with the N to which they are attached optionally form a ring of 3–7 ring atoms and 1–3 of the ring atoms are heteroatoms selected from the group of O, S and N;

R$^8$ is hydrogen, lower alkyl, lower alkenyl, lower alkynyl, lower aryl, lower heteroaryl, or —C(O)R$^9$;

R$^9$ is H, lower alkyl, lower alkenyl, lower alkynyl, lower aryl, lower heteroaryl, —NR$^{10}$R$^{10}$, or —OR$^{11}$, wherein R$^{10}$ and R$^{10}$ taken together optionally form a ring of 3–7 ring atoms and optionally 1–3 of the ring atoms are heteroatoms selected from the group of O, S and N;

R$^{10}$ is hydrogen, lower alkyl, lower heteroaryl, lower aryl, lower alkenyl, or lower alkynyl, $R^{11}$ is lower alkyl, lower alkenyl, lower alkynyl, lower heteroaryl or lower aryl;

$R^{12}$ is hydrogen or lower alkyl;

$R^{21}$ is halogen, —OR$^8$, —SR$^8$ or lower alkyl;

$R^{22}$ is —NR$^8$R$^{10}$;

$R^{24}$ is —NH$_2$, —NO$_2$ or —NO;

$R^{25}$ is halogen or —OH;

$R^{26}$ is —C(O)NH$_2$ or C(O)OEt; and $R^{27}$ is —NH$_2$, —OH or halogen;

provided that when $R^5$ is alicyclic, the ring system does not contain any tetra-substituted Sp$^3$ ring carbons.

In another aspect, the present invention is directed to pharmaceutical compositions comprising the compounds of the invention, in particular, the compounds of Formulae A or I, and compounds formed by the process of the invention, and their polymorphs, solvates, esters, tautomers, diastereomer, enantiomers, pharmaceutically acceptable salts and prodrugs thereof, and one or more pharmaceutical excipients, for use in treatment or prevention of diseases that are HSP90-dependent.

In another aspect, the invention features a method of treating an individual having an HSP90-mediated disorder by administering to the individual a pharmaceutical composition that comprises a pharmaceutically effective amount of a compound of Formulae A or I, or a polymorph, solvate, ester, tautomer, diastereomer, enantiomer, pharmaceutically acceptable salt or prodrug thereof.

In one embodiment, the invention provides a method for treating an individual having a disorder selected from the group of inflammatory diseases, infections, autoimmune disorders, stroke, ischemia, cardiac disorder, neurological disorders, fibrogenetic disorders, proliferative disorders, tumors, leukemias, neoplasms, cancers, carcinomas, metabolic diseases, and malignant disease.

In yet another embodiment, the invention provides a method for treating an individual having a fibrogenetic disorder, such as, for example, scleroderma, polymyositis, systemic lupus, rheumatoid arthritis, liver cirrhosis, keloid formation, interstitial nephritis and pulmonary fibrosis.

In another embodiment, the invention provides a combination therapy comprising the administration of a pharmaceutically effective amount of a compound of Formulae A or I, or a polymorph, solvate, ester, tautomer, diastereomer, enantiomer, pharmaceutically acceptable salt and prodrug thereof, according to any of the preceding aspects or embodiments, and at least one therapeutic agent selected from the group of cytotoxic agents, anti-angiogenesis agents and anti-neoplastic agents. The anti-neoplastic agent may be selected from the group of alkylating agents, anti-metabolites, epidophyllotoxins antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

Any of the above described aspects and embodiments of the invention can be combined where practical.

The individual compounds, methods and compositions prescribed do not preclude the utilization of other, unspecified steps and agents, and those of ordinary skill in the art will appreciate that additional steps and compounds may also be combined usefully within the spirit of various aspects and embodiments of the invention.

Advantages of the invention depend on the specific aspect and embodiment and may include one or more of: ease of synthesis and/or formulation, solubility, and IC$_{50}$ relative to previously existing compounds in the same or different classes of HSP90 inhibitors.

DETAILED DESCRIPTION OF THE INVENTION

I. Definitions

A "pharmaceutically acceptable derivative or prodrug" means any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

A "pharmaceutically acceptable salt" may be prepared for any compound of the invention having a functionality capable of forming a salt, for example, an acid or base functionality. Pharmaceutically acceptable salts may be derived from organic or inorganic acids and bases. Compounds of the invention that contain one or more basic functional groups, e.g., amino or alkylamino, are capable of forming pharmaceutically acceptable salts with pharmaceutically acceptable organic and inorganic acids. These salts can be prepared in situ during the final isolation and purification of the compounds of the invention, or by separately reacting a purified compound of the invention in its free base form with a suitable organic or inorganic acid, and isolating the salt thus formed. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-napthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undeconate. Other acids, such as oxalic, while not in themselves pharmaceutically acceptable, may be employed in the preparation of salts useful as intermediates in obtaining the compounds of the invention and their pharmaceutically acceptable acid addition salts. See, e.g., Berge et al. "Pharmaceutical Salts", *J. Pharm. Sci.* 1977, 66:1–19.

Compounds of the present invention that contain one or more acidic functional groups are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of some of the bases that can be used include sodium hydroxide, potassium hydroxide, choline hydroxide, sodium carbonate, $N^+(C_{1-4}\text{ alkyl})_4$, and the like. Representative organic amines useful for the formation of base addition salts include ethylamine, diethylamine, ethylenediamine, ethanolamine, diethanolamine, piperazine and the like. This invention also envisions the quaternization of any basic nitrogen-containing groups of the compounds disclosed herein. Water or oil-soluble or dispersible products may be obtained by such quaternization. See, for example, Berge et al., supra.

Pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters.

Suitable positions for derivatization of the compounds of the invention to create "prodrugs" include but are not limited, 2-amino substitution. Those of ordinary skill in the art have the knowledge and means to accomplish this without undue experimentation. Various forms of prodrugs are well known in the art. For examples of such prodrug derivatives, see, e.g., a) *Design of Prodrugs*, Bundgaard, A. Ed., Elseview, 1985 and *Method in Enzymology*, Widder, K. et al., Ed.; Academic, 1985, vol. 42, p. 309–396;

b) Bundgaard, H. "Design and Application of Prodrugs" in *A Textbook of Drug Design and Development*, Krosgaard-Larsen and H. Bundgaard, Ed., 1991, Chapter 5, p. 113–191; and c) Bundgaard, H., *Advanced Drug Delivery Review*, 1992, 8, 1–38. Each of which is incorporated herein by reference.

The term "prodrugs" as employed herein includes, but is not limited to, the following groups and combinations of these groups:

Amine Prodrugs:

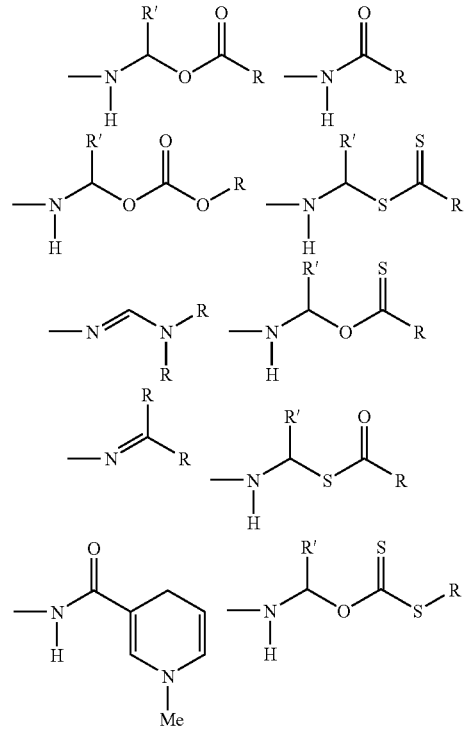

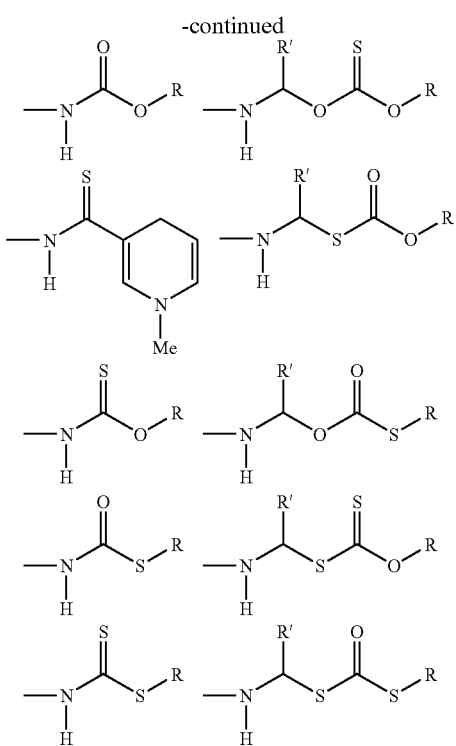

Hydroxy Prodrugs:
Acyloxyalkyl esters;
Alcoxycarbonyloxyalkyl esters;
Alkyl esters;
Aryl esters;
Disulfide containing esters.

The term "alkyl," alone or in combination, refers to an optionally substituted straight-chain, or optionally substituted branched-chain saturated hydrocarbon radical having from one to thirty carbons, more preferably one to twelve carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like. The term "cycloalkyl" embraces cyclic alkyl radicals which include monocyclic, bicyclic, tricyclic, and higher multicyclic alkyl radicals wherein each cyclic moiety has from three to eight carbon atoms. Examples of cycloalkyl radicals include cyclopropyl, cyclobutyl, cyclopentyl, cyclohexyl and the like. A "lower alkyl" is a shorter alkyl, e.g., one containing from one to six carbon atoms.

The term "alkenyl," alone or in combination, refers to an optionally substituted straight-chain, or optionally substituted branched-chain hydrocarbon radical having one or more carbon-carbon double-bonds and having from two to thirty carbon atoms, more preferably two to eighteen carbons. Examples of alkenyl radicals include ethenyl, propenyl, butenyl, 1,3-butadienyl and the like. The term "cycloalkenyl" refers to cyclic alkenyl radicals which include monocyclic, bicyclic, tricyclic, and higher multicyclic alkenyl radicals wherein each cyclic moiety has from three to eight carbon atoms. A "lower alkenyl" refers to an alkenyl having from two to six carbons.

The term "alkynyl," alone or in combination, refers to an optionally substituted straight-chain or optionally substituted branched-chain hydrocarbon radical having one or more carbon-carbon triple-bonds and having from two to thirty carbon atoms, more preferably from two to twelve carbon atoms, from two to six carbon atoms as well as those having from two to four carbon atoms. Examples of alkynyl radicals include ethynyl, 2-propynyl, 2-butynyl, 1,3-butadiynyl and the like. The term "cycloalkynyl" refers to cyclic alkynyl radicals which include monocyclic, bicyclic, tricyclic, and higher multicyclic alkynyl radicals wherein each cyclic moiety has from three to eight carbon atoms. A "lower alkynyl" refers to an alkynyl having from two to six carbons.

The terms "heteroalkyl, heteroalkenyl and heteroalkynyl" include optionally substituted alkyl, alkenyl and alkynyl structures, as described above, and which have one or more skeletal chain atoms selected from an atom other than carbon, e.g., oxygen, nitrogen, sulfur, phosphorous or combinations thereof.

The term "carbon chain" embraces any alkyl, alkenyl, alkynyl, or heteroalkyl, heteroalkenyl, or heteroalkynyl group, which are linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The term "membered ring" can embrace any cyclic structure, including aromatic, heteroaromatic, alicyclic, heterocyclic and polycyclic fused ring systems as described below. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

The term "aryl," alone or in combination, refers to an optionally substituted aromatic hydrocarbon radical of six to twenty ring atoms, and includes mono-aromatic rings and fused aromatic ring. A fused aromatic ring radical contains from two to four fused rings where the ring of attachment is an aromatic ring, and the other individual rings within the fused ring may be aromatic, heteroaromatic, alicyclic or heterocyclic. Further, the term aryl includes mono-aromatic ring and fused aromatic rings containing from six to twelve carbon atoms, as well as those containing from six to ten carbon atoms. Examples of aryl groups include, without limitation, phenyl, naphthyl, anthryl, chrysenyl, and benzopyrenyl ring systems. The term "lower aryl" refers to an aryl having six to ten skeletal ring carbons, e.g., phenyl and naphthyl ring systems.

The term "heteroaryl" refers to optionally substituted aromatic radicals containing from five to twenty skeletal ring atoms and where one or more of the ring atoms is a heteroatom such as, for example, oxygen, nitrogen, sulfur, selenium and phosphorus. The term heteroaryl includes optionally substituted mono-heteroaryl radicals and fused heteroaryl radicals having at least one heteroatom (e.g., quinoline, benzothiazole). A fused heteroaryl radical may contain from two to four fused rings and where the ring of attachment is a heteroaromatic ring, the other individual rings within the fused ring system may be aromatic, heteroaromatic, alicyclic or heterocyclic. The term heteroaryl also includes mono-heteroaryls or fused heteroaryls having from five to twelve skeletal ring atoms, as well as those having from five to ten skeletal ring atoms. Examples of heteroaryls include, without limitation, furanyl, benzofuranyl, chromenyl, pyridyl, pyrrolyl, indolyl, quinolinyl, pyridyl-N-oxide, pyrimidyl, pyrazinyl, imidazolyl, pyrazolyl, oxazolyl, isoxazolyl, benzothiozole, benzimidazole, benzoxazoles, benzothiadiazole, benzoxadiazole, benzotriazole, quinolines, isoquinolines, indolyl, purinyl, indolizinyl, thienyl and the like and their oxides. The term "lower heteroaryl" refers to a heteroaryl having five to ten skeletal ring atoms, e.g., pyridyl, thienyl, pyrimidyl, pyrazinyl, pyrrolyl, or furanyl.

The term "alicyclic" alone or in combination, refers to an optionally substituted saturated or unsaturated nonaromatic hydrocarbon ring system containing from three to twenty ring atoms. The term alicyclic includes mono-alicyclic and fused alicyclic radicals. A fused alicyclic may contain from two to four fused rings where the ring of attachment is an alicyclic ring, and the other individual rings within the fused-alicyclic radical may be aromatic, heteroaromatic, alicyclic and heterocyclic. The term alicyclic also includes mono-alicyclic and fused alicyclic radicals containing from three to twelve carbon atoms, as well as those containing from three to ten carbon atoms. Examples of alicyclics include, without limitation, cyclopropyl, cyclopropenyl, cyclobutyl, cyclopentyl, cyclodecyl, cyclododecyl, cyclopentadienyl, indanyl, and cyclooctatetraenyl ring systems. The term "lower alicyclic" refers to an alicyclic having three to ten skeletal ring carbons, e.g., cyclopropyl, cyclopropenyl, cyclobutyl, cyclopentyl, decalinyl, and cyclohexyl.

The term "heterocyclic" refers to optionally substituted saturated or unsaturated nonaromatic ring radicals containing from five to twenty ring atoms where one or more of the ring atoms are heteroatoms such as, for example, oxygen, nitrogen, sulfur, and phosphorus. The term alicyclic includes mono-heterocyclic and fused heterocyclic ring radicals. A fused heterocyclic radical may contain from two to four fused rings where the attaching ring is a heterocyclic, and the other individual rings within the fused heterocyclic radical may be aromatic, heteroaromatic, alicyclic or heterocyclic. The term heterocyclic also includes mono-heterocyclic and fused alicyclic radicals having from five to twelve skeletal ring atoms, as well as those having from five to ten skeletal ring atoms. Example of heterocyclics include without limitation, tetrahydrofuranyl, benzodiazepinyl, tetrahydroindazolyl, dihyroquinolinyl, and the like. The term "lower heterocyclic" refers to a heterocyclic ring system having five to ten skeletal ring atoms, e.g., dihydropyranyl, pyrrolidinyl, indolyl, piperidinyl, piperazinyl, and the like.

The term "alkylaryl," alone or in combination, refers to an aryl radical as defined above in which one H atom is replaced by an alkyl radical as defined above, such as, for example, tolyl, xylyl and the like.

The term "arylalkyl," or "araalkyl," alone or in combination, refers to an alkyl radical as defined above in which one H atom is replaced by an aryl radical as defined above, such as, for example, benzyl, 2-phenylethyl and the like.

The term "heteroarylalkyl" refers to an alkyl radical as defined above in which one H atom is replaced by a heteroaryl radical as defined above, each of which may be optionally substituted.

The term "alkoxy," alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy," alone or in combination, refers to an aryl ether radical wherein the term aryl is defined as above. Examples of aryloxy radicals include phenoxy, benzyloxy and the like.

The term "alkylthio," alone or in combination, refers to an alkyl thio radical, alkyl-S—, wherein the term alkyl is as defined above.

The term "arylthio," alone or in combination, refers to an aryl thio radical, aryl-S—, wherein the term aryl is as defined above.

The term "heteroarylthio" refers to the group heteroaryl-S—, wherein the term heteroaryl is as defined above.

The term "acyl" refers to a radical —C(O)R where R includes alkyl, alkenyl, alkynyl, aryl, heteroaryl, alicyclic, heterocyclic, arylalkyl or heteroarylalkyl wherein the alkyl, alkenyl, alkynyl, aryl, heteroaryl, alicyclic, heterocyclic, arylalkyl or heteroaryl alkyl groups may be optionally substituted.

The term "acyloxy" refers to the ester group —OC(O)R, where R is H, alkyl, alkenyl, alkynyl, aryl, heteroaryl, alicyclic, heterocyclic, arylalkyl, or heteroarylalkyl wherein the alkyl, alkenyl, alkynyl, aryl, heteroaryl, alicyclic, heterocyclic, arylalkyl or heteroarylalkyl may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

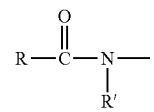

where each of R and R' are independently selected from the group consisting of H, alkyl, aryl, heteroaryl, alicyclic, heterocyclic, arylalkyl and heteroarylalkyl, wherein the alkyl, aryl, heteroaryl, alicyclic, heterocyclic, or arylalkyl groups may be optionally substituted.

The term "oxo" refers to =O.

The term "halogen" includes F, Cl, Br and I.

The terms "haloalkyl, haloalkenyl, haloalkynyl and haloalkoxy" include alkyl, alkenyl, alkynyl and alkoxy structures, as described above, that are substituted with one or more fluorines, chlorines, bromines or iodines, or with combinations thereof.

The terms "perhaloalkyl, perhaloalkyloxy and perhaloacyl" refer to alkyl, alkyloxy and acyl radicals as described above, that all the H atoms are substituted with fluorines, chlorines, bromines or iodines, or combinations thereof.

The terms "cycloalkyl, arylalkyl, aryl, heteroaryl, alicyclic, heterocyclic, alkyl, alkynyl, alkenyl, haloalkyl, and heteroalkyl" include optionally substituted cycloalkyl, arylalkyl, aryl, heteroaryl, alicyclic, heterocyclic, alkyl, alkynyl, alkenyl, haloalkyl and heteroalkyl groups.

The terms "alkylamino", refers to the group —NHR where R is independently selected from alkyl.

The terms "dialkylamino", refers to the group —NRR' where R and R' are alkyls.

The term "sulfide" refers to a sulfur atom covalently linked to two atoms; the formal oxidation state of said sulfur is (II). The term "thioether" may be used interchangeably with the term "sulfide."

The term "sulfoxide" refers to a sulfur atom covalently linked to three atoms, at least one of which is an oxygen atom; the formal oxidation state of said sulfur atom is (IV).

The term "sulfone" refers to a sulfur atom covalently linked to four atoms, at least two of which are oxygen atoms; the formal oxidation state of said sulfur atom is (VI).

The terms "optional" or "optionally" mean that the subsequently described event or circumstance may but need not occur, and that the description includes instances where the event or circumstance occurs and instances in which it does not. For example, "aryl optionally mono- or di-substituted with an alkyl" means that the alkyl may but need not be present, and either one alkyl or two may be present, and the description includes situations where the aryl is substituted with one or two alkyls and situations where the aryl is not substituted with an alkyl.

"Optionally substituted" groups may be substituted or unsubstituted. The substituents of an "optionally substituted" group may include, without limitation, one or more substituents independently selected from the following groups or designated subsets thereof: lower alkyl, lower alkenyl, lower alkynyl, lower aryl, heteroaryl, alicyclic, heterocyclic, arylalkyl, heteroarylalkyl, lower alkoxy, lower aryloxy, amino, alkylamino, dialkylamino, arylalkylamino, alkylthio, arylthio, heteroarylthio, oxo, carbonyl (—C(O)), carboxyesters (—C(O)OR), carboxamido (—C(O)NH$_2$), carboxy, acyloxy, —H, halo, —CN, —NO$_2$, —N$_3$, —SH, —H, —C(O)CH$_3$, perhaloalkyl, perhaloalkoxy, perhaloacyl, guanidinyl, pyridinyl, thiophenyl, furanyl, indolyl, indazolyl, esters, amides, phosphonyl, phosphonic acid, and thioalkyls. An optionally substituted group may be unsubstituted (e.g., ——CH$_2$CH$_3$), fully substituted (e.g., ——CF$_2$CF$_3$), monosubstituted (e.g., ——CH$_2$CH$_2$F) or substituted at a level anywhere in-between fully substituted and monosubstituted (e.g., ——CH$_2$CF$_3$).

The term "pyridine-1-oxy" also means "pyridine-N-oxy."

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well. Further, it is possible using well known techniques to separate the various forms, and some embodiments of the invention may feature purified or enriched species of a given enantiomer or diastereomer.

A "pharmacological composition" refers to a mixture of one or more of the compounds described herein, or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being, compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

A "pharmaceutically effective amount" means an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50–100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate, half-life and maximum tolerated dose (MTD) have yet to be determined but one of ordinary skill in the art can determine these using standard procedures.

In some method embodiments, the preferred therapeutic effect is the inhibition, to some extent, of the growth of cells characteristic of a proliferative disorder, e.g., breast cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

As used herein, the term IC$_{50}$ refers to an amount, concentration or dosage of a particular test compound that achieves a 50% inhibition of a maximal response in an assay that measures such response. In some method embodiments of the invention, the "IC$_{50}$" value of a compound of the invention can be greater for normal cells than for cells exhibiting a proliferative disorder, e.g., breast cancer cells. The value depends on the assay used.

By a "standard" is meant a positive or negative control. A negative control in the context of HER2 expression levels is, e.g., a sample possessing an amount of HER2 protein that correlates with a normal cell. A negative control may also include a sample that contains no HER2 protein. By contrast, a positive control does contain HER2 protein, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick."

By "selectively targeting" is meant affecting one type of cell to a greater extent than another, e.g., in the case of cells with high as opposed to relatively low or normal HER2 levels.

II. Compounds of the Invention

Compounds of the invention and their polymorphs, solvates, esters, tautomers, diastereomers, enantiomers, pharmaceutically acceptable salts or prodrugs show utility for inhibiting HSP90 and treating and preventing diseases that are HSP90-dependent.

One embodiment of the compounds of the invention is of Formula A:

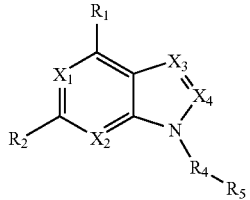

A or a polymorph, solvate, ester, tautomer, diastereomer, enantiomer, pharmaceutically acceptable salt or prodrug thereof, wherein:

$X^1$ and $X^2$ are the same or different and each is nitrogen or —$CR^6$;

$X^3$ is nitrogen or —$CR^3$ wherein $R^3$ is hydrogen, OH, a keto tautomer, —$OR^8$, —CN, halogen, lower alkyl, or —$C(O)R^9$;

$X^4$ is nitrogen or a group $CR^6$ when $X^3$ is nitrogen, and $X_4$ is —$CR^6R^7$ when $X_3$ is —$C^3$;

$R^1$ is halogen, —$OR^8$, —$SR^8$, or lower alkyl;

$R^2$ is —$NR^8R^{10}$;

$R^4$ is —$(CH_2)_n$— wherein n=0–3, —C(O), —C(S), —$SO_2$—, or —$SO_2N$—; and $R^5$ is alkyl, aryl, heteroaryl, alicyclic, or heterocyclic, each of which is optionally bi- or tricyclic, and optionally substituted with H, halogen, lower alkyl, lower alkenyl, lower alkynyl, lower aryl, lower alicyclic, araalkyl, aryloxyalkyl, alkoxyalkyl, perhaloalkyl, perhaloalkyloxy, perhaloacyl, —$N_3$, —$SR^8$, —$OR^8$, —CN, —$CO_2R^9$, —$NO_2$, or —$NR^8R^{10}$;

with the provisos that:

the one not found or described in one or more of JP 10025294; U.S. Pat. No. 4,748,177; U.S. Pat. No. 4,748,177; U.S. Pat. No. 6,369,092; WO 00/06573; WO 02/055521; WO 02/055082; WO 02/055083; *Eur. J. Med. Chem.*, 1994, 29(1), 3–9; and *J. Het. Chem.* 1990, 27(5), 1409;

—$R^4R^5$ is not a ribose or derivative thereof, or a sugar or derivative thereof;

—$R^4R^5$ is not a phosphonate or phosphonic acid, or substituted with phosphonate or phosphonic acid; and when $R^4$ is $(CH_2)_n$ where n=0 or 1, then $R^4$ and $R^5$ are not connected with 'O', e.g., —$CH_2$—O—$CH_2$— or —$CH_2$—$CH_2$—O—$CH_2$—.

In one embodiment, the compound, tautomer, pharmaceutically acceptable salt, or prodrug thereof of Formula A, $X_1$ and $X_2$ are the same or different and each is nitrogen or —$CR^6$; $R^1$ is halogen, —$OR^8$, —$SR^8$, or lower alkyl; $R^2$ is —$NR^8R^{10}$; $R^3$ is hydrogen, —OH or keto tautomer, —$OR^8$, halogen, —CN, lower alkyl, or —$C(O)R^9$; $R^4$ is —$(CH_2)_n$— wherein n=0–3, —C(O), —C(S), —$SO_2$—, or —$SO_2N$—;

and $R^5$ is alkyl, aromatic, heteroaromatic, alicyclic, heterocyclic, each of which is optionally bi- or tricyclic, and optionally substituted with H, halogen, lower alkyl, —$SR^8$, —$OR^8$, —CN, —$CO_2R^9$, —$NO_2$ or —$NR^8R^{10}$; $R^8$ is hydrogen, lower alkyl, lower aryl or —$(CO)R^9$; $R^9$ is lower alkyl, lower aryl, lower heteroaryl, —$NR^8R^{10}$ or $OR^{11}$; $R^{11}$ is lower alkyl or lower aryl; and $R^{10}$ is hydrogen or lower alkyl.

In one embodiment, the compound, tautomer, pharmaceutically acceptable salt thereof, or prodrug thereof of Formula A, $R^1$ is selected from halogen, hydroxyl, lower alkoxy, lower thioalkyl and $C_{1-4}$ alkyl; and $R^2$ is —$NH_2$.

In another embodiment, $R^4$ is —$(CH_2)_n$—, wherein n=0–3.

In another embodiment, $R^1$ is selected from halogen, hydroxyl, lower alkoxy, lower thioalkyl or $C_{1-4}$ alkyl; optionally wherein $R^2$ is $NH_2$.

In another embodiment, $R^4$ is —$(CH_2)_n$—, wherein n=0–3.

In another embodiment, $R^4$ is —$(CH_2)_n$—, wherein n=0–3, $R^1$ is selected from halogen, hydroxyl, lower alkoxy, lower thioalkyl, and $C_{1-4}$ alkyl, and $R^2$ is optionally $NH_2$.

In another embodiment, $R^1$ is halogen, hydroxyl, lower alkoxy, lower thioalkyl, or $C_{1-4}$ alkyl; and $R^2$ is optionally $NH_2$, $R^4$ is —$(CH_2)$—, and $R^5$ is phenyl, benzyl, or pyridyl, all optionally substituted with H, halogen, lower alkyl, —$SR^8$, —$OR^8$ (or cyclic ethers such as methylenedioxy), —CN, —$CO_2R^9$, —$NO_2$, or —$NR^8R^{10}$; $R^8$ is hydrogen, lower alkyl, lower aryl or —$(CO)R^9$; $R^9$ is lower alkyl, lower aryl, lower heteroaryl, —$NR^8R^{10}$ or —$OR^{11}$; $R^{11}$ is lower alkyl or lower aryl; and $R^{10}$ is hydrogen or lower alkyl.

In another embodiment $R^1$ is halogen, $R^2$ is —$NH_2$, $R^4$ is —$CH_2$—, $R^6$ is H or halogen, and $R^5$ is phenyl optionally substituted with H, halogen, $C_{1-4}$ alkyl, $C_{1-4}$ alkoxy, $C_{1-4}$ alkylthio, perhaloalkyl, perhaloalkyloxy, —CN, —$NO_2$, —$NH_2$ or —$CO_2R^{11}$.

In another embodiment, $R^1$ is halogen, $R^2$ is —$NH_2$, $R^4$ is —$CH_2$—, $R^6$ is H, and $R^5$ is 2-halo-3,5-dimethoxyphenyl optionally substituted with H, halogen, $C_{1-4}$ alkyl, $C_{1-4}$ alkoxy, $C_{1-4}$ alkylthio, perhaloalkyl, perhaloalkyloxy, —CN, —$NO_2$, —$NH_2$, or —$CO_2R^{11}$ at the para (4-) position.

In another embodiment, $R^1$ is chloro, $R^2$ is —$NH_2$, $R^4$ is —$CH_2$—, $R^6$ is H and $R^5$ is 2-chloro-3,4,5-trimethoxyphenyl.

In another embodiment, $R^1$ is chloro, $R^2$ is —$NH_2$, $R^4$ is —$CH_2$—, $R^6$ is H and $R^5$ is 2-bromo-3,4,5-trimethoxyphenyl. In other embodiments, $R^5$ is selected from 2-iodo-3,4,5-trimethoxyphenyl, 2-fluoro-3,4,5-trimethoxyphenyl, and 2-bromo-3,4,5-trimethoxyphenyl.

Any of the forgoing embodiments can be combined where feasible and appropriate.

In another aspect, the invention provides compounds of Formula IV:

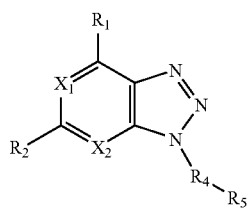

IV or a polymorph, solvate, ester, tautomer, diastereomer, enantiomer, pharmaceutically acceptable salt or prodrug thereof, wherein:

$X_1$ and $X_2$ are the same or different and each is nitrogen or $CR_6$;

$R_1$ is halogen, $-OR_8$, $-SR^8$, or lower alkyl;

$R_2$ is $-NR^8R_{10}$;

$R^4$ is $-CH_{2n}-$ where n=0–3, $-C(O)$, $-C(S)$, $-SO_2-$, or $-SO_2N-$;

$R_5$ is alkyl, aryl, heteroaryl, alicyclic, or heterocyclic, all optionally bi- or tricyclic, and all optionally substituted with H, halogen, lower alkyl, $-SR_8$, $-OR_8$, $-CN$, $-CO_2R_9$, $-NO_2$, or $-NR_8R_{10}$;

$R_8$ is hydrogen, lower alkyl, lower aryl or $-(CO)R_9$;

$R_9$ is lower alkyl, lower aryl, lower heteroaryl, $-NR_8R_{10}$ or $-OR_{11}$; $R_{11}$ is lower alkyl or lower aryl; and $R_{10}$ is hydrogen or lower alkyl.

In one embodiment of the compounds of Formula IV, a tautomer, pharmaceutically acceptable salt thereof, or prodrug thereof, $R^1$ is halogen, hydroxyl, lower alkoxy, lower thioalkyl, or $C_{1-4}$ alkyl; and $R^2$ is $-NH_2$.

In one embodiment of the compounds of Formula IV, a tautomer, pharmaceutically acceptable salt thereof, or prodrug thereof, $R^1$ is halogen, hydroxyl, lower alkoxy, lower thioalkyl, or $C_{1-4}$ alkyl; and $R^2$ is $-NH_2$; $R^4$ is $-CH_2-$, $-C(O)$, $-C(S)$, $-SO_2-$.

In one embodiment of the compounds of Formula IV, a tautomer, pharmaceutically acceptable salt thereof, or prodrug thereof, $R^1$ is halogen or $C_{1-4}$ alkyl; and $R^2$ is $NH_2$, $R^4$ is $-CH_2-$.

In one embodiment of the compounds of Formula IV, a tautomer, pharmaceutically acceptable salt thereof, or prodrug thereof, $R^1$ is halogen, hydroxyl, lower alkoxy, lower thioalkyl, or $C_{1-4}$ alkyl; and $R^2$ is $NH_2$, $R^4$ is $-(CH_2)_n-$, where n=0–3.

In one embodiment of the compounds of Formula IV, a tautomer, pharmaceutically acceptable salt, or prodrug thereof, $R^4$ is $-C(O)$ or $-CH_2-$; $R^1$ is halogen, lower alkoxy or $C_{1-4}$ alkyl; and $R^2$ is $NH_2$.

In another embodiment, the invention provides compounds of Formula I:

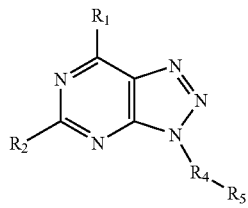

Formula I or a polymorph, solvate, ester, tautomer, enantiomer, diastereomer, pharmaceutically acceptable salt or prodrug thereof, wherein:

$R^1$ is halogen, $-OR^{11}$, $-SR^{11}$ or lower alkyl;

$R^2$ is $-NHR^8$;

$R^4$ is $-CHR^{12}-$, $-C(O)-$, $-C(S)-$, $-S(O)-$ or $-SO_2-$;

$R^5$ is aryl, heteroaryl, alicyclic, or heterocyclic, wherein:
the aryl group is substituted with 3 to 5 substituents,
the heteroaryl group is substituted with 2 to 5 substituents,
the alicyclic group is substituted with 3 to 5 substituents,
the heterocyclic group is substituted with 3 to 5 substituents, and
the substituents are selected from the group consisting of halogen, lower alkyl, lower alkenyl, lower alkynyl, $-SR^8$, $-OR^8$, $-CN$, $-C(O)OH$, $-C(O)R^9$, $-NO_2$, $-NR^8R^{10}$, lower aryl, heteroaryl, alicyclic, lower heterocyclic, arylalkyl, heteroarylalkyl, amino, alkylamino, dialkylamino, oxo, perhaloalkyl, perhaloalkoxy, perhaloacyl, guanidinyl, pyridinyl, thiophenyl, furanyl, indolyl, and indazolyl, wherein $R^8$ and $R^{10}$ taken together with the N to which they are attached optionally form a ring of 3–7 ring atoms and 1–3 of the ring atoms are heteroatoms selected from the group of O, S and N;

$R^8$ is hydrogen, lower alkyl, lower alkenyl, lower alkynyl, lower aryl, lower heteroaryl, or $-C(O)R^9$;

$R^9$ is H, lower alkyl, lower alkenyl, lower alkynyl, lower aryl, lower heteroaryl, $-NR^{10}R^{10}$ or $-OR^{11}$, wherein $R^{10}$ and $R^{10}$ taken together optionally form a ring of 3–7 ring atoms and optionally 1–3 of the ring atoms are heteroatoms selected from the group of O, S and N;

$R^{10}$ is hydrogen, lower alkyl, lower heteroaryl, lower aryl, lower alkenyl, or lower alkynyl, $R^{11}$ is lower alkyl, lower alkenyl, lower alkynyl, lower heteroaryl or lower aryl; and $R^{12}$ is hydrogen or lower alkyl;

provided that when $R^5$ is alicyclic, the ring system does not contain any tetra-substituted $sp^3$ ring carbons.

In one embodiment of the compounds of Formula I, or a polymorph, solvate, ester, tautomer, enantiomer, diastereomer, pharmaceutically acceptable salt or prodrug thereof, each of the aryl, heteroaryl, alicyclic or heterocyclic group is monocyclic or bicyclic.

In another embodiment of the compounds of Formula I, or a polymorph, solvate, ester, tautomer, enantiomer, diastereomer, pharmaceutically acceptable salt or prodrug thereof, $R^1$ is halogen; and $R^2$ is $-NHR^8$, where $R^8$ is hydrogen or $-C(O)R^9$.

In another embodiment of the compounds of Formula I, or a polymorph, solvate, ester, tautomer, enantiomer, pharmaceutically acceptable salt or prodrug thereof, $R^1$ is chloro or bromo, $R^2$ is $-NHR^8$, where $R^8$ is hydrogen or $-C(O)R^9$; and $R^4$ is lower alkyl.

In another embodiment of the compounds of Formula I, or a polymorph, solvate, ester, tautomer, enantiomer, pharmaceutically acceptable salt or prodrug thereof, $R^1$ is chloro or bromo, $R^2$ is $-NHR^8$, where $R^8$ is hydrogen or $-C(O)R^9$; and $R^4$ is $-CHR^{12}-$.

In another embodiment of the compounds of Formula I, or a polymorph, solvate, ester, tautomer, enantiomer, pharmaceutically acceptable salt or prodrug thereof, $R^1$ is chloro or bromo, $R^2$ is $-NHR^8$, where $R^8$ is hydrogen or $-C(O)R^9$; and $R^4$ is $-CH_2-$.

In another embodiment of the compounds of Formula I, or a polymorph, solvate, ester, tautomer, enantiomer, pharmaceutically acceptable salt or prodrug thereof, $R^2$ is $-NHR^8$, where $R^8$ is hydrogen or $-C(O)R^9$; and $R^4$ is $-CH_2-$.

In another embodiment of the compounds of Formula I, or a polymorph, solvate, ester, tautomer, enantiomer, pharmaceutically acceptable salt or prodrug thereof, $R^1$ is halogen; $R^2$ is $-NH_2$, $R^4$ is $-CH_2-$; and $R^5$ is aryl or heteroaryl, wherein each of the aryl and heteroaryl is monocyclic or bicyclic and is substituted with 3 to 5 substituents.

In another embodiment of the compounds of Formula I, or a polymorph, solvate, ester, tautomer, enantiomer, pharmaceutically acceptable salt or prodrug thereof, $R^1$ is chloro or bromo; $R^2$ is —$NH_2$, $R^4$ is —$CH_2$—; and $R^5$ is aryl or heteroaryl, wherein each of the aryl and heteroaryl is monocyclic or bicyclic and is substituted with 3 to 5 substituents.

In another embodiment of the compounds of Formula I, or a polymorph, solvate, ester, tautomer, enantiomer, pharmaceutically acceptable salt or prodrug thereof, $R^1$ is chloro or bromo, $R^2$ is —$NH_2$, and $R^5$ is a phenyl having at least three substituents.

In another embodiment of the compounds of Formula I, or a polymorph, solvate, ester, tautomer, enantiomer, pharmaceutically acceptable salt or prodrug thereof, $R^1$ is chloro or bromo, $R^2$ is —$NH_2$ and $R^5$ is a pyridyl having at least two substituents.

In another embodiment of the compounds of Formula I, or a polymorph, solvate, ester, tautomer, enantiomer, pharmaceutically acceptable salt or prodrug thereof, $R^1$ is chloro or bromo, $R^2$ is —$NH_2$, and $R^5$ is 1-oxy-pyridyl (N-oxy-pyridyl) having at least two substituents.

It should be understood that any of the foregoing embodiments can be combined where feasible and appropriate.

In another embodiment, the invention provides compounds, or polymorphs, solvates, esters, tautomers, pharmaceutically acceptable salts or prodrugs thereof, prepared by the process comprising:

reacting a compound of formula Y and a compound of formula Z, wherein:

Y is a represented by any one of the following formulae:

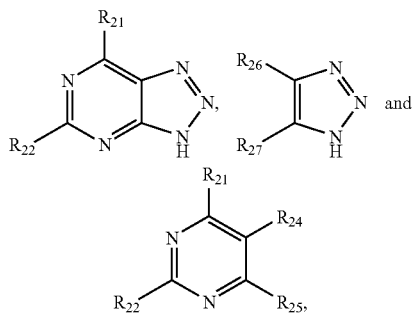

Z is $L^1$—$R^4$—$R^5$; wherein:

$L^1$ is halogen, $NR^8R^{10}$, triflate, tosylate, or mesylate;

$R^4$ is —$CHR^{12}$—, —C(O)—, —C(S)—, —S(O)— or —$SO_2$—;

$R^5$ is aryl, heteroaryl, alicyclic, or heterocyclic, wherein:

the aryl group is substituted with 3 to 5 substituents, the heteroaryl group is substituted with 2 to 5 substituents, the alicyclic group is substituted with 3 to 5 substituents, the heterocyclic group is substituted with 3 to 5 substituents, and the substituents are selected from the group consisting of halogen, lower alkyl, lower alkenyl, lower alkynyl, —$SR^8$, —$OR^8$, —CN, —C(O)OH, —C(O)$R^9$, —$NO_2$, —$NR^8R^{10}$, lower aryl, heteroaryl, alicyclic, lower heterocyclic, arylalkyl, heteroarylalkyl, amino, alkylamino, dialkylamino, oxo, perhaloalkyl, perhaloalkoxy, perhaloacyl, guanidinyl, pyridinyl, thiophenyl, furanyl, indolyl, and indazolyl, wherein $R^8$ and $R^{10}$ taken together with the N to which they are attached optionally form a ring of 3–7 ring atoms and 1–3 of the ring atoms are heteroatoms selected from the group of O, S and N.

$R^8$ is hydrogen, lower alkyl, lower alkenyl, lower alkynyl, lower aryl, lower heteroaryl, or —C(O)$R^9$;

$R^9$ is H, lower alkyl, lower alkenyl, lower alkynyl, lower aryl, lower heteroaryl, —$NR^{10}R^{10}$ or —$OR^{11}$, wherein $R^{10}$ and $R^{10}$ taken together optionally form a ring of 3–7 ring atoms and optionally 1–3 of the ring atoms are heteroatoms selected from the group of O, S and N;

$R^{10}$ is hydrogen, lower alkyl, lower heteroaryl, lower aryl, lower alkenyl, or lower alkynyl, $R^{11}$ is lower alkyl, lower alkenyl, lower alkynyl, lower heteroaryl or lower aryl;

$R^{12}$ is hydrogen or lower alkyl;

$R^{21}$ is halogen, —$OR^8$, —$SR^8$ or lower alkyl;

$R^{22}$ is —$NR^8R^{10}$;

$R^{24}$ is —$NH_2$, —$NO_2$ or —NO;

$R^{25}$ is halogen or —OH;

$R^{26}$ is —C(O)$NH_2$ or C(O)OEt; and $R^{27}$ is —$NH_2$, —OH or halogen;

provided that when $R^5$ is alicyclic, the ring system does not contain any tetra-substituted $sp^3$ ring carbons.

In one embodiment of the compounds prepared by the process of the invention, or a polymorph, solvate, ester, tautomer, pharmaceutically acceptable salt or prodrug thereof, $L^1$ is —Cl, —Br or —$NH_2$; $R^5$ is aryl or heteroaryl.

In another embodiment of the compounds prepared by the process of the invention, or a polymorph, solvate, ester, tautomer, pharmaceutically acceptable salt or prodrug thereof, $R^4$ is —$CH_2$—.

In another embodiment of the compounds prepared by the process of the invention, or a polymorph, solvate, ester, tautomer, pharmaceutically acceptable salt or prodrug thereof, $R^5$ is aryl, heteroaryl, alicyclic, or heterocyclic, optionally mono- or bicyclic.

In another embodiment of the compounds prepared by the process of the invention, or a polymorph, solvate, ester, tautomer, pharmaceutically acceptable salt or prodrug thereof, $L^1$ is —Cl, —Br or —$NH_2$; $R^4$ is —$CH_2$—; and $R^5$ is aryl or heteroaryl.

In another embodiment of the compounds prepared by the process of the invention, or a polymorph, solvate, ester, tautomer, pharmaceutically acceptable salt or prodrug thereof, Y is a triazolopyrimidine.

In another embodiment of the compounds prepared by the process of the invention, or a polymorph, solvate, ester, tautomer, pharmaceutically acceptable salt or prodrug thereof, Y is a triazole.

In another embodiment of the compounds prepared by the process of the invention, or a polymorph, solvate, ester, tautomer, pharmaceutically acceptable salt or prodrug thereof, Y is a pyrimidine.

In another embodiment of the compounds prepared by the process of the invention, or a polymorph, solvate, ester, tautomer, pharmaceutically acceptable salt or prodrug thereof, the reaction is performed in a solvent comprising a member selected from the group of DMF, THF and DMSO.

In another embodiment of the compounds prepared by the process of the invention, or a polymorph, solvate, ester, tautomer, pharmaceutically acceptable salt or prodrug thereof, the reaction is performed in a solvent that comprises DMF.

It should be understood that any of the foregoing embodiments can be combined where feasible and appropriate.

Illustrative species of the compounds of the invention that are based on Formula I are described in TABLE 1. Prodrugs which can be employed by these compounds include, but are not limited to, those listed in the Definition section.

TABLE 1

Exemplary Compounds of Formula I

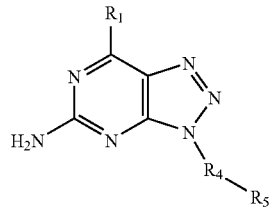

| No. | Ex. | $R^1$ | $R^4$ | $R^5$ |
|---|---|---|---|---|
| 1 | 5 | Cl | $CH_2$ | 3,4,5-Trimethoxyphenyl |
| 2 | 6 | Cl | $CH_2$ | 2-Chloro-3,4,5-trimethoxyphenyl |
| 3 | 8 | Cl | $CH_2$ | 2-Bromo-3,4,5-trimethoxyphenyl |
| 4 | 10 | Cl | $CH_2$ | 2-Iodo-3,4,5-trimethoxyphenyl |
| 5 | | Cl | $CH_2$ | 2-Fluoro-3,4,5-trimethoxyphenyl |
| 6 | | Cl | $CH_2$ | 3,4,5-Trimethylphenyl |
| 7 | | Cl | $CH_2$ | 2-Chloro-3,4,5-trimethylphenyl |
| 8 | | Cl | $CH_2$ | 2-Bromo-3,4,5-trimethylphenyl |
| 9 | | Cl | $CH_2$ | 2-Iodo-3,4,5-trimethylphenyl |
| 10 | | Cl | $CH_2$ | 2-Fluoro-3,4,5-trimethylphenyl |
| 11 | | Cl | $CH_2$ | 3,5-Dimethoxy-4-methylphenyl |
| 12 | | Cl | $CH_2$ | 2-Chloro-3,5-dimethoxy-4-methylphenyl |
| 13 | | Cl | $CH_2$ | 2-Bromo-3,5-dimethoxy-4-methylphenyl |
| 14 | | Cl | $CH_2$ | 2-Iodo-3,5-dimethoxy-4-methylphenyl |
| 15 | | Cl | $CH_2$ | 2-Fluoro-3,5-dimethoxy-4-methylphenyl |
| 16 | | Cl | $CH_2$ | 3,5-Dichloro-4-methylphenyl |
| 17 | | Cl | $CH_2$ | 2,3,5-Trichloro-4-methylphenyl |
| 18 | | Cl | $CH_2$ | 2-Bromo-3,5-dichloro-4-methylphenyl |
| 19 | | Cl | $CH_2$ | 2-Iodo-3,5-dichloro-4-methylphenyl |
| 20 | | Cl | $CH_2$ | 2-Fluoro-3,5-dichloro-4-methylphenyl |
| 21 | | Cl | $CH_2$ | 3,5-Dibromo-4-methylphenyl |
| 22 | | Cl | $CH_2$ | 2-Chloro-3,5-dibromo-4-methylphenyl |
| 23 | | Cl | $CH_2$ | 2,3,5-Tribromo-4-methylphenylphenyl |
| 24 | | Cl | $CH_2$ | 2-Iodo-3,5-dibromo-4-methylphenyl |
| 25 | | Cl | $CH_2$ | 2-Fluoro-3,5-dibromo-4-methylphenyl |
| 26 | | Cl | $CH_2$ | 3,5-Dichloro-4-methoxyphenyl |
| 27 | | Cl | $CH_2$ | 2,3,5-Trichloro-4-methoxyphenyl |
| 28 | | Cl | $CH_2$ | 2-Bromo-3,5-dichloro-4-methoxyphenyl |
| 29 | | Cl | $CH_2$ | 2-Iodo-3,5-dichloro-4-methoxyphenyl |
| 30 | | Cl | $CH_2$ | 2-Fluoro-3,5-dichloro-4-methoxyphenyl |
| 31 | | Cl | $CH_2$ | 3,5-Dibromo-4-methoxyphenyl |
| 32 | | Cl | $CH_2$ | 2-Chloro-3,5-dibromo-4-methoxyphenyl |
| 33 | | Cl | $CH_2$ | 2,3,5-Tribromo-4-methoxyphenyl |
| 34 | | Cl | $CH_2$ | 2-Iodo-3,5-dibromo-4-methoxyphenyl |
| 35 | | Cl | $CH_2$ | 2-Fluoro-3,5-dibromo-4-methoxyphenyl |
| 36 | | Cl | $CH_2$ | 3-Chloro-5-bromo-4-methylphenyl |
| 37 | | Cl | $CH_2$ | 2,3-Dichloro-5-bromo-4-methylphenyl |
| 38 | | Cl | $CH_2$ | 2,5-Dibromo-3-chloro-4-methylphenyl |
| 39 | | Cl | $CH_2$ | 2-Iodo-3-chloro-5-bromo-4-methylphenyl |
| 40 | | Cl | $CH_2$ | 2-Fluoro-3-chloro-5-bromo-4-methylphenyl |
| 41 | | Cl | $CH_2$ | 3-Chloro-5-bromo-4-methoxyphenylphenyl |
| 42 | | Cl | $CH_2$ | 2,3-Dichloro-5-bromo-4-methoxyphenyl |
| 43 | | Cl | $CH_2$ | 2,5-Dibromo-3-chloro-4-methoxyphenyl |
| 44 | | Cl | $CH_2$ | 2-Iodo-3-chloro-5-bromo-4-methoxyphenyl |
| 45 | | Cl | $CH_2$ | 2-Fluoro-3-chloro-5-bromo-4-methoxyphenyl |
| 46 | | Cl | $CH_2$ | 3-Bromo-5-chloro-4-methylphenyl |
| 47 | | Cl | $CH_2$ | 2,5-Dichloro-3-bromo-4-methylphenyl |
| 48 | | Cl | $CH_2$ | 2,3-Dibromo-5-chloro-4-methylphenyl |
| 49 | | Cl | $CH_2$ | 2-Iodo-3-bromo-5-chloro-4-methylphenyl |
| 50 | | Cl | $CH_2$ | 2-Fluoro-3-bromo-5-chloro-4-methylphenyl |
| 51 | | Cl | $CH_2$ | 3-Bromo-5-chloro-4-methoxyphenyl |
| 52 | | Cl | $CH_2$ | 2,5-Dichloro-3-bromo-4-methoxyphenyl |
| 53 | | Cl | $CH_2$ | 2,3-Dibromo-5-chloro-4-methoxyphenyl |
| 54 | | Cl | $CH_2$ | 2-Iodo-3-bromo-5-chloro-4-methoxyphenyl |
| 55 | | Cl | $CH_2$ | 2-Fluoro-3-bromo-5-chloro-4-methoxyphenyl |
| 56 | | Cl | $CH_2$ | 3,5-Dimethoxy-4-trifluoromethylphenyl |
| 57 | | Cl | $CH_2$ | 2-Chloro-3,5-dimethoxy-4-trifluoromethylphenyl |
| 58 | | Cl | $CH_2$ | 2-Bromo-3,5-dimethoxy-4-trifluoromethylphenyl |
| 59 | | Cl | $CH_2$ | 2-Iodo-3,5-dimethoxy-4-trifluoromethylphenyl |
| 60 | | Cl | $CH_2$ | 2-Fluoro-3,5-dimethoxy-4-trifluoromethylphenyl |
| 61 | | Cl | $CH_2$ | 3,5-dibromo-4-trifluoromethoxyphenyl |
| 62 | | Cl | $CH_2$ | 2-Chloro-3,5-dibromo-4-trifluoromethoxyphenyl |
| 63 | | Cl | $CH_2$ | 2,3,5-Tribromo-4-trifluoromethoxyphenyl |

TABLE 1-continued

Exemplary Compounds of Formula I

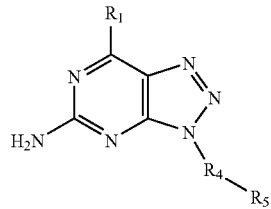

I

| No. | Ex. | R¹ | R⁴ | R⁵ |
|---|---|---|---|---|
| 64 | | Cl | CH₂ | 2-Iodo-3,5-dibromo-4-trifluoromethoxyphenyl |
| 65 | | Cl | CH₂ | 2-Fluoro-3,5-dibromo-4-trifluoromethoxyphenyl |
| 66 | | Cl | CH₂ | 3,5-Dimethyl-4-methoxyphenyl |
| 67 | | Cl | CH₂ | 2-Chloro-3,5-dimethyl-4-methoxyphenyl |
| 68 | | Cl | CH₂ | 2-Bromo-3,5-dimethyl-4-methoxyphenyl |
| 69 | | Cl | CH₂ | 2-Iodo-3,5-dimethyl-4-methoxyphenyl |
| 70 | | Cl | CH₂ | 2-Fluoro-3,5-dimethyl-4-methoxyphenyl |
| 71 | | Cl | CH₂ | 3,5-Dimethyl-4-bromophenyl |
| 72 | | Cl | CH₂ | 2-Chloro-3,5-dimethyl-4-bromophenyl |
| 73 | | Cl | CH₂ | 2,4-Dibromo-3,5-dimethylphenyl |
| 74 | | Cl | CH₂ | 2-Iodo-3,5-dimethyl-4-bromophenyl |
| 75 | | Cl | CH₂ | 2-Fluoro-3,5-dimethyl-4-bromophenyl |
| 76 | | Cl | CH₂ | 3,5-Dimethyl-4-chlorophenyl |
| 77 | | Cl | CH₂ | 2,4-Dichloro-3,5-dimethylphenyl |
| 78 | | Cl | CH₂ | 2-Bromo-3,5-dimethyl-4-chlorophenyl |
| 79 | | Cl | CH₂ | 2-Iodo-3,5-dimethyl-4-chlorophenyl |
| 80 | | Cl | CH₂ | 2-Fluoro-3,5-dimethyl-4-chlorophenyl |
| 81 | | Br | CH₂ | 3,4,5-Trimethoxyphenyl |
| 82 | | Br | CH₂ | 2-Chloro-3,4,5-trimethoxyphenyl |
| 83 | | Br | CH₂ | 2-Bromo-3,4,5-trimethoxyphenyl |
| 84 | | Br | CH₂ | 2-Iodo-3,4,5-trimethoxyphenyl |
| 85 | | Br | CH₂ | 2-Fluoro-3,4,5-trimethoxyphenyl |
| 86 | | Br | CH₂ | 3,4,5-Trimethylphenyl |
| 87 | | Br | CH₂ | 2-Chloro-3,4,5-trimethylphenyl |
| 88 | | Br | CH₂ | 2-Bromo-3,4,5-trimethylphenyl |
| 89 | | Br | CH₂ | 2-Iodo-3,4,5-trimethylphenyl |
| 90 | | Br | CH₂ | 2-Fluoro-3,4,5-trimethylphenyl |
| 91 | | Br | CH₂ | 3,5-Dimethoxy-4-methylphenyl |
| 92 | | Br | CH₂ | 2-Chloro-3,5-dimethoxy-4-methylphenyl |
| 93 | | Br | CH₂ | 2-Bromo-3,5-dimethoxy-4-methylphenyl |
| 94 | | Br | CH₂ | 2-Iodo-3,5-dimethoxy-4-methylphenyl |
| 95 | | Br | CH₂ | 2-Fluoro-3,5-dimethoxy-4-methylphenyl |
| 96 | | Br | CH₂ | 3,5-Dichloro-4-methylphenyl |
| 97 | | Br | CH₂ | 2,3,5-Trichloro-4-methylphenyl |
| 98 | | Br | CH₂ | 2-Bromo-3,5-dichloro-4-methylphenyl |
| 99 | | Br | CH₂ | 2-Iodo-3,5-dichloro-4-methylphenyl |
| 100 | | Br | CH₂ | 2-Fluoro-3,5-dichloro-4-methylphenyl |
| 101 | | Br | CH₂ | 3,5-Dibromo-4-methylphenyl |
| 102 | | Br | CH₂ | 2-Chloro-3,5-dibromo-4-methylphenyl |
| 103 | | Br | CH₂ | 2,3,5-Tribromo-4-methylphenylphenyl |
| 104 | | Br | CH₂ | 2-Iodo-3,5-dibromo-4-methylphenyl |
| 105 | | Br | CH₂ | 2-Fluoro-3,5-dibromo-4-methylphenyl |
| 106 | | Br | CH₂ | 3,5-Dichloro-4-methoxyphenyl |
| 107 | | Br | CH₂ | 2,3,5-Trichloro-4-methoxyphenyl |
| 108 | | Br | CH₂ | 2-Bromo-3,5-dichloro-4-methoxyphenyl |
| 109 | | Br | CH₂ | 2-Iodo-3,5-dichloro-4-methoxyphenyl |
| 110 | | Br | CH₂ | 2-Fluoro-3,5-dichloro-4-methoxyphenyl |
| 111 | | Br | CH₂ | 3,5-Dibromo-4-methoxyphenyl |
| 112 | | Br | CH₂ | 2-Chloro-3,5-dibromo-4-methoxyphenyl |
| 113 | | Br | CH₂ | 2,3,5-Tribromo-4-methoxyphenyl |
| 114 | | Br | CH₂ | 2-Iodo-3,5-dibromo-4-methoxyphenyl |
| 115 | | Br | CH₂ | 2-Fluoro-3,5-dibromo-4-methoxyphenyl |
| 116 | | Br | CH₂ | 3-Chloro-5-bromo-4-methylphenyl |
| 117 | | Br | CH₂ | 2,3-Dichloro-5-bromo-4-methylphenyl |
| 118 | | Br | CH₂ | 2,5-Dibromo-3-chloro-4-methylphenyl |
| 119 | | Br | CH₂ | 2-Iodo-3-chloro-5-bromo-4-methylphenyl |
| 120 | | Br | CH₂ | 2-Fluoro-3-chloro-5-bromo-4-methylphenyl |
| 121 | | Br | CH₂ | 3-Chloro-5-bromo-4-methoxyphenylphenyl |
| 122 | | Br | CH₂ | 2,3-Dichloro-5-bromo-4-methoxyphenyl |
| 123 | | Br | CH₂ | 2,5-Dibromo-3-chloro-4-methoxyphenyl |
| 124 | | Br | CH₂ | 2-Iodo-3-chloro-5-bromo-4-methoxyphenyl |
| 125 | | Br | CH₂ | 2-Fluoro-3-chloro-5-bromo-4-methoxyphenyl |
| 126 | | Br | CH₂ | 3-Bromo-5-chloro-4-methylphenyl |

TABLE 1-continued

Exemplary Compounds of Formula I

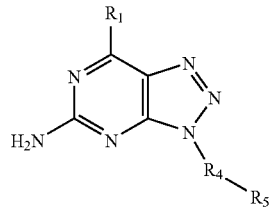

I

| No. | Ex. | R¹ | R⁴ | R⁵ |
|---|---|---|---|---|
| 127 | | Br | CH₂ | 2,5-Dichloro-3-bromo-4-methylphenyl |
| 128 | | Br | CH₂ | 2,3-Dibromo-5-chloro-4-methylphenyl |
| 129 | | Br | CH₂ | 2-Iodo-3-bromo-5-chloro-4-methylphenyl |
| 130 | | Br | CH₂ | 2-Fluoro-3-bromo-5-chloro-4-methylphenyl |
| 131 | | Br | CH₂ | 3-Bromo-5-chloro-4-methoxyphenyl |
| 132 | | Br | CH₂ | 2,5-Dichloro-3-bromo-4-methoxyphenyl |
| 133 | | Br | CH₂ | 2,3-Dibromo-5-chloro-4-methoxyphenyl |
| 134 | | Br | CH₂ | 2-Iodo-3-bromo-5-chloro-4-methoxyphenyl |
| 135 | | Br | CH₂ | 2-Fluoro-3-bromo-5-chloro-4-methoxyphenyl |
| 136 | | Br | CH₂ | 3,5-Dimethoxy-4-trifluoromethylphenyl |
| 137 | | Br | CH₂ | 2-Chloro-3,5-dimethoxy-4-trifluoromethylphenyl |
| 138 | | Br | CH₂ | 2-Bromo-3,5-dimethoxy-4-trifluoromethylphenyl |
| 139 | | Br | CH₂ | 2-Iodo-3,5-dimethoxy-4-trifluoromethylphenyl |
| 140 | | Br | CH₂ | 2-Fluoro-3,5-dimethoxy-4-trifluoromethylphenyl |
| 141 | | Br | CH₂ | 3,5-Dibromo-4-trifluoromethoxyphenyl |
| 142 | | Br | CH₂ | 2-Chloro-3,5-dibromo-4-trifluoromethoxyphenyl |
| 143 | | Br | CH₂ | 2,3,5-Tribromo-4-trifluoromethoxyphenyl |
| 144 | | Br | CH₂ | 2-Iodo-3,5-dibromo-4-trifluoromethoxyphenyl |
| 145 | | Br | CH₂ | 2-Fluoro-3,5-dibromo-4-trifluoromethoxyphenyl |
| 146 | | Br | CH₂ | 3,5-Dimethyl-4-methoxyphenyl |
| 147 | | Br | CH₂ | 2-Chloro-3,5-dimethyl-4-methoxyphenyl |
| 148 | | Br | CH₂ | 2-Bromo-3,5-dimethyl-4-methoxyphenyl |
| 149 | | Br | CH₂ | 2-Iodo-3,5-dimethyl-4-methoxyphenyl |
| 150 | | Br | CH₂ | 2-Fluoro-3,5-dimethyl-4-methoxyphenyl |
| 151 | | Br | CH₂ | 3,5-Dimethyl-4-bromophenyl |
| 152 | | Br | CH₂ | 2-Chloro-3,5-dimethyl-4-bromophenyl |
| 153 | | Br | CH₂ | 2,4-Dibromo-3,5-dimethylphenyl |
| 154 | | Br | CH₂ | 2-Iodo-3,5-dimethyl-4-bromophenyl |
| 155 | | Br | CH₂ | 2-Fluoro-3,5-dimethyl-4-bromophenyl |
| 156 | | Br | CH₂ | 3,5-Dimethyl-4-chlorophenyl |
| 157 | | Br | CH₂ | 2,4-Dichloro-3,5-dimethylphenyl |
| 158 | | Br | CH₂ | 2-Bromo-3,5-dimethyl-4-chlorophenyl |
| 159 | | Br | CH₂ | 2-Iodo-3,5-dimethyl-4-chlorophenyl |
| 160 | 1 | Cl | CH₂ | 3,5-Dimethyl-4-methoxypyridin-2-yl |
| 161 | 2 | Cl | CH₂ | 3,5-Dimethyl-4-methoxy-1-oxypyridin-2-yl |
| 162 | | Cl | CH₂ | 6-Bromo-3,5-dimethyl-4-methoxypyridin-2-yl |
| 163 | | Cl | CH₂ | 6-Chloro-3,5-dimethyl-4-methoxypyridin-2-yl |
| 164 | | Cl | CH₂ | 6-Chloro-3,5-dimethyl-4-methoxy-1-oxypyridin-2-yl |
| 165 | | Cl | CH₂ | 6-Bromo-3,5-dimethyl-4-methoxy-1-oxypyridin-2-yl |
| 166 | | Cl | CH₂ | 3,5-Dimethyl-4-bromopyridin-2-yl |
| 167 | | Cl | CH₂ | 3,5-Dimethyl-4-bromo-1-oxypyridin-2-yl |
| 168 | | Cl | CH₂ | 6-Bromo-3,5-dimethyl-4-bromopyridin-2-yl |
| 169 | | Cl | CH₂ | 6-Chloro-3,5-dimethyl-4-bromopyridin-2-yl |
| 170 | | Cl | CH₂ | 6-Chloro-3,5-dimethyl-4-bromo-1-oxypyridin-2-yl |
| 171 | | Cl | CH₂ | 4,6-Dibromo-3,5-dimethyl-1-oxypyridin-2-yl |
| 172 | | Cl | CH₂ | 3,5-Dimethyl-4-chloropyridin-2-yl |
| 173 | | Cl | CH₂ | 3,5-Dimethyl-4-chloro-1-oxypyridin-2-yl |
| 174 | | Cl | CH₂ | 6-Bromo-3,5-dimethyl-4-chloropyridin-2-yl |
| 175 | | Cl | CH₂ | 6-Chloro-3,5-dimethyl-4-chloropyridin-2-yl |
| 176 | | Cl | CH₂ | 4,6-Dichloro-3,5-dimethyl-1-oxypyridin-2-yl |
| 177 | | Cl | CH₂ | 6-Bromo-3,5-dimethyl-4-chloro-1-oxypyridin-2-yl |
| 178 | | Cl | CH₂ | 3,5-Dimethyl-4-iodopyridin-2-yl |
| 179 | | Cl | CH₂ | 3,5-Dimethyl-4-iodo-1-oxypyridin-2-yl |
| 180 | | Cl | CH₂ | 6-Bromo-3,5-dimethyl-4-iodopyridin-2-yl |
| 181 | | Cl | CH₂ | 6-Chloro-3,5-dimethyl-4-iodopyridin-2-yl |
| 182 | | Cl | CH₂ | 6-Chloro-3,5-dimethyl-4-iodo-1-oxypyridin-2-yl |
| 183 | | Cl | CH₂ | 6-Bromo-3,5-dimethyl-4-iodo-1-oxypyridin-2-yl |
| 184 | | Cl | CH₂ | 3,5-Dimethyl-4-thiomethyl-pyridin-2-yl |
| 185 | | Cl | CH₂ | 3,5-Dimethyl-4-thiomethyl-1-oxypyridin-2-yl |
| 186 | | Cl | CH₂ | 6-Bromo-3,5-dimethyl-4-thiomethyl-pyridin-2-yl |
| 187 | | Cl | CH₂ | 6-Chloro-3,5-dimethyl-4-thiomethyl-pyridin-2-yl |
| 188 | | Cl | CH₂ | 6-Chloro-3,5-dimethyl-4-thiomethyl-1-oxypyridin-2-yl |
| 189 | | Cl | CH₂ | 6-Bromo-3,5-dimethyl-4-thiomethyl-1-oxypyridin-2-yl |

TABLE 1-continued

Exemplary Compounds of Formula I

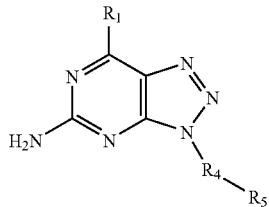

| No. | Ex. | R¹ | R⁴ | R⁵ |
|---|---|---|---|---|
| 190 | | Cl | CH₂ | 3,4,5-Trimethyl-pyridin-2-yl |
| 191 | | Cl | CH₂ | 3,4,5-Trimethyl-1-oxypyridin-2-yl |
| 192 | | Cl | CH₂ | 6-Bromo-3,4,5-trimethyl-pyridin-2-yl |
| 193 | | Cl | CH₂ | 6-Chloro-3,4,5-trimethyl-pyridin-2-yl |
| 194 | | Cl | CH₂ | 6-Chloro-3,4,5-trimethyl-1-oxypyridin-2-yl |
| 195 | | Cl | CH₂ | 6-Bromo-3,4,5-trimethyl-1-oxypyridin-2-yl |
| 196 | | Cl | CH₂ | 4,5,6-Trimethoxypyridin-2-yl |
| 197 | | Cl | CH₂ | 4,5,6-Trimethoxy-1-oxypyridin-2-yl |
| 198 | | Cl | CH₂ | 3-Bromo-4,5,6-trimethoxypyridin-2-yl |
| 199 | | Cl | CH₂ | 3-Chloro-4,5,6-trimethoxypyridin-2-yl |
| 200 | | Cl | CH₂ | 3-Chloro-4,5,6-trimethoxy-1-oxypyridin-2-yl |
| 201 | | Cl | CH₂ | 3-Bromo-4,5,6-trimethoxy-1-oxypyridin-2-yl |
| 202 | | Cl | CH₂ | 3,4,5-Trimethoxy-pyridin-2-yl |
| 203 | | Cl | CH₂ | 3,4,5-Trimethoxy-1-oxypyridin-2-yl |
| 204 | | Cl | CH₂ | 3-Bromo-3,4,5-trimethoxy-pyridin-2-yl |
| 205 | | Cl | CH₂ | 3-Chloro-3,4,5-trimethoxy-pyridin-2-yl |
| 206 | | Cl | CH₂ | 3-Chloro-3,4,5-trimethoxy-1-oxypyridin-2-yl |
| 207 | | Cl | CH₂ | 3-Bromo-3,4,5-trimethoxy-1-oxypyridin-2-yl |
| 208 | | Cl | CH₂ | 4,5,6-Trimethyl-pyridin-2-yl |
| 209 | | Cl | CH₂ | 4,5,6-Trimethyl-1-oxypyridin-2-yl |
| 210 | | Cl | CH₂ | 3-Bromo-4,5,6-trimethyl-pyridin-2-yl |
| 211 | | Cl | CH₂ | 3-Chloro-4,5,6-trimethyl-pyridin-2-yl |
| 212 | | Cl | CH₂ | 3-Chloro-4,5,6-trimethyl-1-oxypyridin-2-yl |
| 213 | | Cl | CH₂ | 3-Bromo-4,5,6-trimethyl-1-oxypyridin-2-yl |
| 214 | | Cl | CH₂ | 4,6-Dimethyl-5-methoxy-pyridin-2-yl |
| 215 | | Cl | CH₂ | 4,6-Dimethyl-5-methoxy-1-oxypyridin-2-yl |
| 216 | | Cl | CH₂ | 3-Bromo-4,6-dimethyl-5-methoxy-pyridin-2-yl |
| 217 | | Cl | CH₂ | 3-Chloro-4,6-dimethyl-5-methoxy-pyridin-2-yl |
| 218 | | Cl | CH₂ | 3-Chloro-4,6-dimethyl-5-methoxy-1-oxypyridin-2-yl |
| 219 | | Cl | CH₂ | 3-Bromo-4,6-dimethyl-5-methoxy-1-oxypyridin-2-yl |
| 220 | | Cl | CH₂ | 4-Bromo-5,6-dimethoxy-pyridin-2-yl |
| 221 | | Cl | CH₂ | 4-Bromo-5,6-dimethoxy-1-oxypyridin-2-yl |
| 222 | | Cl | CH₂ | 3,4-Dibromo-5,6-dimethoxy-pyridin-2-yl |
| 223 | | Cl | CH₂ | 3-Chloro-4-bromo-5,6-dimethoxy-pyridin-2-yl |
| 224 | | Cl | CH₂ | 3-Chloro-4-bromo-5,6-dimethoxy-1-oxypyridin-2-yl |
| 225 | | Cl | CH₂ | 3,4-Dibromo-5,6-dimethoxy-1-oxypyridin-2-yl |
| 226 | | Cl | CH₂ | 4,6-Dimethyl-5-methoxypyridin-3-yl |
| 227 | | Cl | CH₂ | 4,6-Dimethyl-5-methoxy-1-oxypyridin-3-yl |
| 228 | | Cl | CH₂ | 4,6-Dimethyl-5-bromopyridin-3-yl |
| 229 | | Cl | CH₂ | 4,6-Dimethyl-5-chloropyridin-3-yl |
| 230 | | Cl | CH₂ | 5,6-Dimethyl-4-bromopyridin-3-yl |
| 231 | | Cl | CH₂ | 5,6-Dimethyl-4-chloropyridin-3-yl |
| 232 | | Cl | CH₂ | 4,6-Dimethyl-5-bromo-1-oxypyridin-pyridin-3-yl |
| 233 | | Cl | CH₂ | 4,6-Dimethyl-5-chloro-1-oxypyridin-pyridin-3-yl |
| 234 | | Cl | CH₂ | 5,6-Dimethyl-4-bromo-1-oxypyridin-pyridin-3-yl |
| 235 | | Cl | CH₂ | 5,6-Dimethyl-4-chloro-1-oxypyridin-pyridin-3-yl |
| 236 | | Cl | CH₂ | 2,6-Dimethyl-3-methoxypyridin-4-yl |
| 237 | | Cl | CH₂ | 2,6-Dimethyl-pyridin-4-yl |
| 238 | | Cl | CH₂ | 2,3,6-Trimethyl-pyridin-4-yl |
| 239 | | Cl | CH₂ | 2,3,6-Trimethoxy-pyridin-4-yl |
| 240 | | Cl | CH₂ | 2,6-Dimethyl-3-bromopyridin-4-yl |
| 241 | | Cl | CH₂ | 2,6-Dimethyl-3-chloropyridin-4-yl |
| 242 | | Cl | CH₂ | 2,6-Dichloro-3-bromopyridin-4-yl |
| 243 | | Cl | CH₂ | 2,6-Dibromo-3-chloropyridin-4-yl |
| 244 | | Cl | CH₂ | 2,3,6-Trichloro-pyridin-4-yl |
| 245 | | Cl | CH₂ | 2,3,6-Tribromo-pyridin-4-yl |
| 246 | | Cl | CH₂ | 2,6-Dimethyl-3-methoxy-1-oxy-pyridin-4-yl |
| 247 | | Cl | CH₂ | 2,6-Dimethyl-1-oxy-pyridin-4-yl |
| 248 | | Cl | CH₂ | 2,3,6-Trimethyl-1-oxy-pyridin-4-yl |
| 249 | | Cl | CH₂ | 2,3,6-Trimethoxy-1-oxy-pyridin-4-yl |
| 250 | | Cl | CH₂ | 2,6-Dimethyl-3-bromo-1-oxy-pyridin-4-yl |
| 251 | | Cl | CH₂ | 2,6-Dimethyl-3-chloro-1-oxy-pyridin-4-yl |
| 252 | | Cl | CH₂ | 2,6-Dichloro-3-bromo-1-oxy-pyridin-4-yl |

TABLE 1-continued

Exemplary Compounds of Formula I

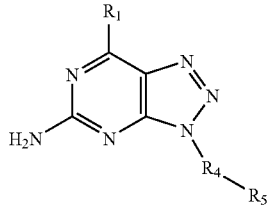

I

| No. | Ex. | R¹ | R⁴ | R⁵ |
|---|---|---|---|---|
| 253 | | Cl | CH₂ | 2,6-Dibromo-3-chloro-1-oxy-pyridin-4-yl |
| 254 | | Cl | CH₂ | 2,3,6-Trichioro-1-oxy-pyridin-4-yl |
| 255 | | Cl | CH₂ | 2,3,6-Tribromo-1-oxy-pyridin-4-yl |
| 256 | | Cl | CH₂ | 4,6-Dimethyl-5-iodopyridin-3-yl |
| 257 | | Cl | CH₂ | 5,6-Dimethyl-4-iodopyridin-3-yl |
| 258 | | Cl | CH₂ | 4,5,6-Trichloropyridin-3-yl |
| 259 | | Cl | CH₂ | 4,5,6-Tribromopyridin-3-yl |
| 260 | | Br | CH₂ | 3,5-Dimethyl-4-methoxypyridin-2-yl |
| 261 | | Br | CH₂ | 3,5-Dimethyl-4-methoxy-1-oxypyridin-2-yl |
| 262 | | Br | CH₂ | 6-Bromo-3,5-dimethyl-4-methoxypyridin-2-yl |
| 263 | | Br | CH₂ | 6-Chloro-3,5-dimethyl-4-methoxypyridin-2-yl |
| 264 | | Br | CH₂ | 6-Chloro-3,5-dimethyl-4-methoxy-1-oxypyridin-2-yl |
| 265 | | Br | CH₂ | 6-Bromo-3,5-dimethyl-4-methoxy-1-oxypyridin-2-yl |
| 266 | | Br | CH₂ | 3,5-Dimethyl-4-bromopyridin-2-yl |
| 267 | | Br | CH₂ | 3,5-Dimethyl-4-bromo-1-oxypyridin-2-yl |
| 268 | | Br | CH₂ | 6-Bromo-3,5-dimethyl-4-bromopyridin-2-yl |
| 269 | | Br | CH₂ | 6-Chloro-3,5-dimethyl-4-bromopyridin-2-yl |
| 270 | | Br | CH₂ | 6-Chloro-3,5-dimethyl-4-bromo-1-oxypyridin-2-yl |
| 271 | | Br | CH₂ | 4,6-Dibromo-3,5-dimethyl-1-oxypyridin-2-yl |
| 272 | | Br | CH₂ | 3,5-Dimethyl-4-chloropyridin-2-yl |
| 273 | | Br | CH₂ | 3,5-Dimethyl-4-chloro-1-oxypyridin-2-yl |
| 274 | | Br | CH₂ | 6-Bromo-3,5-dimethyl-4-chloropyridin-2-yl |
| 275 | | Br | CH₂ | 6-Chloro-3,5-dimethyl-4-chloropyridin-2-yl |
| 276 | | Br | CH₂ | 4,6-Dichloro-3,5-dimethyl-1-oxypyridin-2-yl |
| 277 | | Br | CH₂ | 6-Bromo-3,5-dimethyl-4-chloro-1-oxypyridin-2-yl |
| 278 | | Br | CH₂ | 3,5-Dimethyl-4-iodopyridin-2-yl |
| 279 | | Br | CH₂ | 3,5-Dimethyl-4-iodo-1-oxypyridin-2-yl |
| 280 | | Br | CH₂ | 6-Bromo-3,5-dimethyl-4-iodopyridin-2-yl |
| 281 | | Br | CH₂ | 6-Chloro-3,5-dimethyl-4-iodopyridin-2-yl |
| 282 | | Br | CH₂ | 6-Chloro-3,5-dimethyl-4-iodo-1-oxypyridin-2-yl |
| 283 | | Br | CH₂ | 6-Bromo-3,5-dimethyl-4-iodo-1-oxypyridin-2-yl |
| 284 | | Br | CH₂ | 3,5-Dimethyl-4-thiomethyl-pyridin-2-yl |
| 285 | | Br | CH₂ | 3,5-Dimethyl-4-thiomethyl-1-oxypyridin-2-yl |
| 286 | | Br | CH₂ | 6-Bromo-3,5-dimethyl-4-thiomethyl-pyridin-2-yl |
| 287 | | Br | CH₂ | 6-Chloro-3,5-dimethyl-4-thiomethyl-pyridin-2-yl |
| 288 | | Br | CH₂ | 6-Chloro-3,5-dimethyl-4-thiomethyl-1-oxypyridin-2-yl |
| 289 | | Br | CH₂ | 6-Bromo-3,5-dimethyl-4-thiomethyl-1-oxypyridin-2-yl |
| 290 | | Br | CH₂ | 3,4,5-Trimethyl-pyridin-2-yl |
| 291 | | Br | CH₂ | 3,4,5-Trimethyl-1-oxypyridin-2-yl |
| 292 | | Br | CH₂ | 6-Bromo-3,4,5-trimethyl-pyridin-2-yl |
| 293 | | Br | CH₂ | 6-Chloro-3,4,5-trimethyl-pyridin-2-yl |
| 294 | | Br | CH₂ | 6-Chloro-3,4,5-trimethyl-1-oxypyridin-2-yl |
| 295 | | Br | CH₂ | 6-Bromo-3,4,5-trimethyl-1-oxypyridin-2-yl |
| 296 | | Br | CH₂ | 3,4,5-Trimethoxy-pyridin-2-yl |
| 297 | | Br | CH₂ | 3,4,5-Trimethoxy-1-oxypyridin-2-yl |
| 298 | | Br | CH₂ | 6-Bromo-3,4,5-trimethoxy-pyridin-2-yl |
| 299 | | Br | CH₂ | 6-Chloro-3,4,5-trimethoxy-pyridin-2-yl |
| 300 | | Br | CH₂ | 6-Chloro-3,4,5-trimethoxy-1-oxypyridin-2-yl |
| 301 | | Br | CH₂ | 6-Bromo-3,4,5-trimethoxy-1-oxypyridin-2-yl |
| 302 | | Br | CH₂ | 4,5,6-Trimethoxypyridin-2-yl |
| 303 | | Br | CH₂ | 4,5,6-Trimethoxy-1-oxypyridin-2-yl |
| 304 | | Br | CH₂ | 3-Bromo-4,5,6-trimethoxypyridin-2-yl |
| 305 | | Br | CH₂ | 3-Chloro-4,5,6-trimethoxypyridin-2-yl |
| 306 | | Br | CH₂ | 3-Chloro-4,5,6-trimethoxy-1-oxypyridin-2-yl |
| 307 | | Br | CH₂ | 3-Bromo-4,5,6-trimethoxy-1-oxypyridin-2-yl |
| 308 | | Br | CH₂ | 4,5,6-Trimethoxypyridin-2-yl |
| 309 | | Br | CH₂ | 4,5,6-Trimethoxy-1-oxypyridin-2-yl |
| 310 | | Br | CH₂ | 3-Bromo-4,5,6-trimethyl-pyridin-2-yl |
| 311 | | Br | CH₂ | 3-Chloro-4,5,6-trimethyl-pyridin-2-yl |
| 312 | | Br | CH₂ | 3-Chloro-4,5,6-trimethyl-1-oxypyridin-2-yl |
| 313 | | Br | CH₂ | 3-Bromo-4,5,6-trimethyl-1-oxypyridin-2-yl |
| 314 | | Br | CH₂ | 4,6-Dimethyl-5-methoxy-pyridin-2-yl |
| 315 | | Br | CH₂ | 4,6-Dimethyl-5-methoxy-1-oxypyridin-2-yl |

TABLE 1-continued

Exemplary Compounds of Formula I

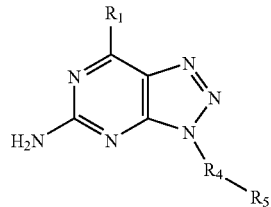

I

| No. | Ex. | R¹ | R⁴ | R⁵ |
|---|---|---|---|---|
| 316 | | Br | CH₂ | 3-Bromo-4,6-dimethyl-5-methoxy-pyridin-2-yl |
| 317 | | Br | CH₂ | 3-Chloro-4,6-dimethyl-5-methoxy-pyridin-2-yl |
| 318 | | Br | CH₂ | 3-Chloro-4,6-dimethyl-5-methoxy-1-oxypyridin-2-yl |
| 319 | | Br | CH₂ | 3-Bromo-4,6-dimethyl-5-methoxy-1-oxypyridin-2-yl |
| 320 | | Br | CH₂ | 4-Bromo-5,6-dimethoxy-pyridin-2-yl |
| 321 | | Br | CH₂ | 4-Bromo-5,6-dimethoxy-1-oxypyridin-2-yl |
| 322 | | Br | CH₂ | 3,4-Dibromo-5,6-dimethoxy-pyridin-2-yl |
| 323 | | Br | CH₂ | 3-Chloro-4-bromo-5,6-dimethoxy-pyridin-2-yl |
| 324 | | Br | CH₂ | 3-Chloro-4-bromo-5,6-dimethoxy-I-oxypyridin-2-yl |
| 325 | | Br | CH₂ | 3,4-Dibromo-5,6-dimethoxy-1-oxypyridin-2-yl |
| 326 | | Br | CH₂ | 4,6-Dimethyl-5-methoxypyridin-3-yl |
| 327 | | Br | CH₂ | 4,6-Dimethyl-5-methoxy-1-oxypyridin-3-yl |
| 328 | | Br | CH₂ | 4,6-Dimethyl-5-bromopyridin-3-yl |
| 329 | | Br | CH₂ | 4,6-Dimethyl-5-chloropyridin-3-yl |
| 330 | | Br | CH₂ | 5,6-Dimethyl-4-bromopyridin-3-yl |
| 331 | | Br | CH₂ | 5,6-Dimethyl-4-chloropyridin-3-yl |
| 332 | | Br | CH₂ | 4,6-Dimethyl-5-bromo-1-oxypyridin-pyridin-3-yl |
| 333 | | Br | CH₂ | 4,6-Dimethyl-5-chloro-1-oxypyridin-pyridin-3-yl |
| 334 | | Br | CH₂ | 5,6-Dimethyl-4-bromo-1-oxypyridin-pyridin-3-yl |
| 335 | | Br | CH₂ | 5,6-Dimethyl-4-chloro-1-oxypyridin-pyridin-3-yl |
| 336 | | Br | CH₂ | 2,6-Dimethyl-3-methoxypyridin-4-yl |
| 337 | | Br | CH₂ | 2,6-Dimethyl-pyridin-4-yl |
| 338 | | Br | CH₂ | 2,3,6-Trimethyl-pyridin-4-yl |
| 339 | | Br | CH₂ | 2,3,6-Trimethoxy-pyridin-4-yl |
| 340 | | Br | CH₂ | 2,6-Dimethyl-3-bromopyridin-4-yl |
| 341 | | Br | CH₂ | 2,6-Dimethyl-3-chloropyridin-4-yl |
| 342 | | Br | CH₂ | 2,6-Dichloro-3-bromopyridin-4-yl |
| 343 | | Br | CH₂ | 2,6-Dibromo-3-chloropyridin-4-yl |
| 344 | | Br | CH₂ | 2,3,6-Trichloro-pyridin-4-yl |
| 345 | | Br | CH₂ | 2,3,6-Tribromo-pyridin-4-yl |
| 346 | | Br | CH₂ | 2,6-Dimethyl-3-methoxy-1-oxy-pyridin-4-yl |
| 347 | | Br | CH₂ | 2,6-Dimethyl-1-oxy-pyridin-4-yl |
| 348 | | Br | CH₂ | 2,3,6-Trimethyl-1-oxy-pyridin-4-yl |
| 349 | | Br | CH₂ | 2,3,6-Trimethoxy-1-oxy-pyridin-4-yl |
| 350 | | Br | CH₂ | 2,6-Dimethyl-3-bromo-1-oxy-pyridin-4-yl |
| 351 | | Br | CH₂ | 2,6-Dimethyl-3-chloro-1-oxy-pyridin-4-yl |
| 352 | | Br | CH₂ | 2,6-Dichloro-3-bromo-1-oxy-pyridin-4-yl |
| 353 | | Br | CH₂ | 2,6-Dibromo-3-chloro-1-oxy-pyridin-4-yl |
| 354 | | Br | CH₂ | 2,3,6-Trichloro-1-oxy-pyridin-4-yl |
| 355 | | Br | CH₂ | 2,3,6-Tribromo-1-oxy-pyridin-4-yl |
| 356 | | Br | CH₂ | 4,6-Dimethyl-5-iodopyridin-3-yl |
| 357 | | Br | CH₂ | 5,6-Dimethyl-4-iodopyridin-3-yl |
| 358 | | Br | CH₂ | 4,5,6-Trichloropyridin-3-yl |
| 359 | | Br | CH₂ | 4,5,6-Tribromopyridin-3-yl |
| 360 | | Cl | CH₂ | 4,5,6-Trimethoxy-3-chloropyridin-2-yl |
| 361 | | Br | CH₂ | 4,5,6-Trimethoxy-3-chloropyridin-2-yl |
| 362 | | Cl | CH₂ | 4,5,6-Trimethoxy-3-bromopyridin-2-yl |
| 363 | | Br | CH₂ | 4,5,6-Trimethoxy-3-bromopyridin-2-yl |
| 364 | | Cl | CH₂ | 4,5,6-Trimethoxy-pyridin-3-yl |
| 365 | | Cl | CH₂ | 4,5,6-Trimethoxy-1-oxy-pyridin-3-yl |
| 366 | | Cl | CH₂ | 2-Bromo-4,5,6-trimethoxy-pyridin-3-yl |
| 367 | | Cl | CH₂ | 2-Chloro-4,5,6-trimethoxy-pyridin-3-yl |
| 368 | | Cl | CH₂ | 2-Chloro-4,5,6-trimethoxy-1-oxy-pyridin-3-yl |
| 369 | | Cl | CH₂ | 2-Bromo-4,5,6-trimethoxy-1-oxy-pyridin-3-yl |
| 370 | | Cl | CH₂ | 4,5,6-Trimethyl-pyridin-3-yl |
| 371 | | Cl | CH₂ | 4,5,6-Trimethyl-1-oxy-pyridin-3-yl |
| 372 | | Cl | CH₂ | 2-Bromo-4,5,6-trimethyl-pyridin-3-yl |
| 373 | | Cl | CH₂ | 2-Chloro-4,5,6-trimethyl-pyridin-3-yl |
| 374 | | Cl | CH₂ | 2-Chloro-4,5,6-trimethyl-1-oxy-pyridin-3-yl |
| 375 | | Cl | CH₂ | 2-Bromo-4,5,6-trimethyl-1-oxy-pyridin-3-yl |
| 376 | | Cl | CH₂ | 2-Iodo-4,5,6-trimethyl-pyridin-3-yl |
| 377 | | Cl | CH₂ | 2-Iodo-4,5,6-trimethyl-pyridin-3-yl |
| 378 | | Br | CH₂ | 4,5,6-Trimethoxy-pyridin-3-yl |

TABLE 1-continued

Exemplary Compounds of Formula I

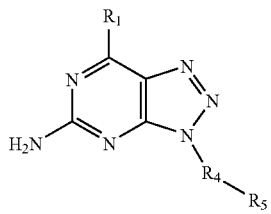

I

| No. | Ex. | R¹ | R⁴ | R⁵ |
|-----|-----|-----|-----|-----|
| 379 | | Br | CH₂ | 4,5,6-Trimethoxy-1-oxy-pyridin-3-yl |
| 380 | | Br | CH₂ | 2-Bromo-4,5,6-trimethoxy-pyridin-3-yl |
| 381 | | Br | CH₂ | 2-Chloro-4,5,6-trimethoxy-pyridin-3-yl |
| 382 | | Br | CH₂ | 2-Chloro-4,5,6-trimethoxy-1-oxy-pyridin-3-yl |
| 383 | | Br | CH₂ | 2-Bromo-4,5,6-trimethoxy-1-oxy-pyridin-3-yl |
| 384 | | Br | CH₂ | 4,5,6-Trimethyl-pyridin-3-yl |
| 385 | | Br | CH₂ | 4,5,6-Trimethyl-1-oxy-pyridin-3-yl |
| 386 | | Br | CH₂ | 2-Bromo-4,5,6-trimethyl-pyridin-3-yl |
| 387 | | Br | CH₂ | 2-Chloro-4,5,6-trimethyl-pyridin-3-yl |
| 388 | | Br | CH₂ | 2-Chloro-4,5,6-trimethyl-1-oxy-pyridin-3-yl |
| 389 | | Br | CH₂ | 2-Bromo-4,5,6-trimethyl-1-oxy-pyridin-3-yl |

Compounds of interest in Table 1 are compounds 2, 3, 13, 82, 83, 162, 163, 168, 169, 174, 175, 180, 181, 186, 187, 192, 193, 198, 199, 204, 205, 210, 211, 228, 229, 230, 231, 232, 233, 234, 235, 236, 237, 250, 251, 262, 263, 268, 269, 274, 275, 280, 281, 286, 287, 292, 293, 298, 299, 304, 305, 310, 311, 316, 317, 328, 329, 338, 372, 373, 380 and 381 with selected compounds being 162, 163, 168, 169, 174, 175, 180, 181, 186, 187, 192, 193, 198, 199, 204, 205, 228, 229, 262, 263, 268, 269, 274, 275, 280, 281, 286, 287, 292, 293, 316, 317, 328, and 329.

III. Synthesis of the Compounds of the Invention

The compounds of Formula I (see Scheme 1) of the present invention may be synthesized by various methods known in the art, including those described in, for example, Parkanyi, *J. Heterocyl. Chem.*, 1990, 27(5), 1409–13; Beauchamp, U.S. Pat. No. 4,714,701, 1987; Meier, U.S. Pat. No. 5,204,353, 1993. Gillespie, WO 02/055083; Peterson, *J. Med. Chem.*, 1990, 33(4), 1214–19. The general synthetic strategy is outlined in Scheme 1 and consists of three parts: (1) constructing the bicyclic system, starting from either a pyrimidine or a 1,2,3-triazole, (2) appending the R⁵—R⁴— group, and (3) further elaborating the ring systems.

Importantly, one skilled in the art will recognize that the sequence of events is not necessarily (1)-(2)-(3), and that these events may be interchanged, provided there be no incompatibility between the reagents and the functional groups specific to the point in case.

Scheme 1

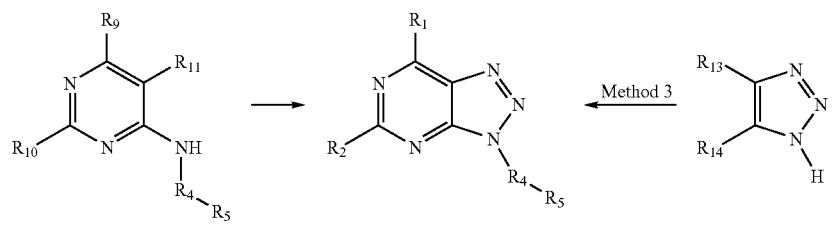

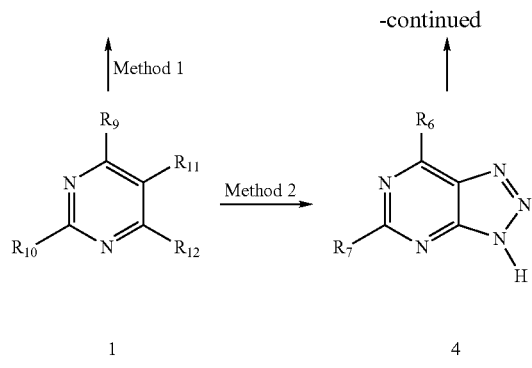

The starting material and/or the intermediates of, e.g., Formulae 1, 2 or/and 4 can exist in tautomeric forms, and both forms are indiscriminately described in the specification.

From Pyrimidines:

Method 1

Compounds of Formula I can be prepared from the commercially available substituted pyrimidines compounds of Formula 1 where $R^9$ is OH or halogen, $R^{10}$ is amino or protected amino or any group that can be converted to amino, such as SMe, $R^{11}$ is H or $NO_2$, $R^{12}$ is Cl, (see Scheme 1 and Scheme 2) by treating with an excess halogenating agent such as $POCl_3$, oxalyl chloride, or $PCl_5$, and a formulating agent such as DMF to give compounds of Formula 1 where $R^9$ is halogen, and $R^{12}$ is halogen, followed by halogen displacement with an nucleophile, such as $NH_2$—$R^4$—$R^5$, in solvents such as EtOH, tBuOH etc. in presence of organic bases such as $Et_3N$, $(i-Pr)_2NEt$ etc. to yield a compound of Formula 2. Formula 2, where $R^{11}$ is $NO_2$, may then be reduced with zinc and formic acid or sodium dithionite to give compounds of Formula 2, where $R^{11}$ is $NH_2$, see Dempcy, U.S. Publication No. 2003/0078413 A1. Compounds of Formula I can then be prepared by diazotization with an alkali metal nitrite such as $NaNO_2$ in inorganic acids such as HCl, followed by in situ cyclization. (See Beauchamp, U.S. Pat. No. 4,714,701; Meier, U.S. Pat. No. 5,204,353) These compounds of Formula I can be further modified as necessary.

Scheme 2

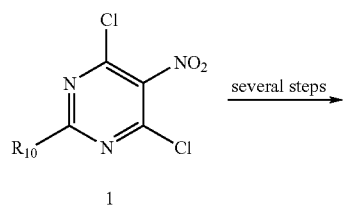

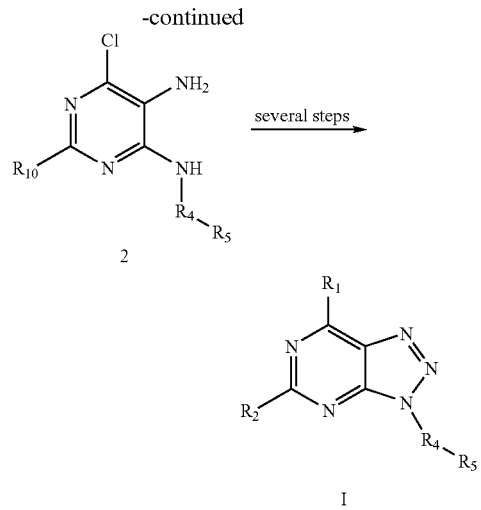

Formula 2, where $R^{11}$ is H, can be treated with diazonium salts such as 4-chloroaniline diazonium salt prepared from 4-chloroaniline and $NaNO_2$ inorganic acids such as HCl to give pyrimidine 5-azo-analog, that can be reduced with zinc dust in EtOH/AcOH (1:1) solution to give compounds of Formula 2, where $R^{11}$ is $NH_2$ (see Meier, U.S. Pat. No. 5,204,353).

Method 2

Scheme 3

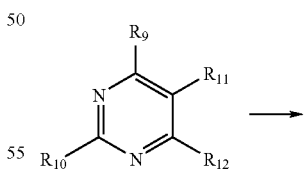

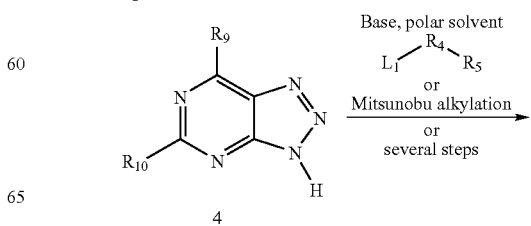

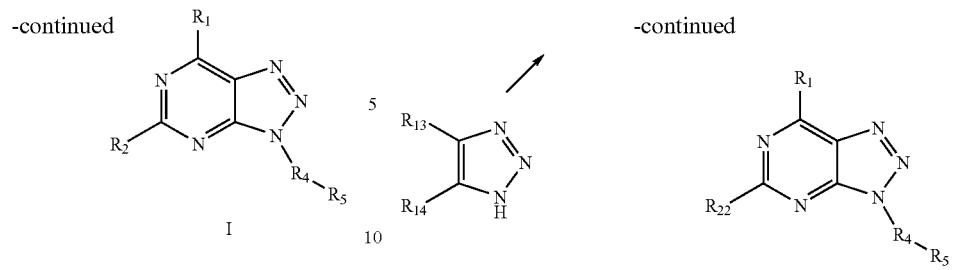

Compounds of Formula I also can be prepared from the commercially available substituted diamino pyrimidines compounds of Formula 1 where $R^9$ is OH or halogen, $R^{10}$ is amino or protected amino or any group that can be converted to amino, such as SMe, $R^{11}$ & $R^{12}$ are $NH_2$, (see Scheme 3) following the diazotization method described earlier in Method 1 to give compounds of Formula 4. Formula 4 can be alkylated in the presence of a base such as $K_2CO_3$, NaH, $Cs_2CO_3$, DBU etc. with/without the presence of halide such as NaI, KI, $(Bu)_3NI$ etc., and in a polar solvent such as DMF, THF, DMSO etc. using electrophiles such as $L^1$—$R^4$—$R^5$ where $L^1$ is a leaving group. Leaving groups include but are not limited to, e.g., halogen, triflate, tosylate, mesylate etc. (See Kasibhatla, WO 03/037860) Compounds of Formula I can also be prepared from compounds of Formula 4 using Mitsunobu alkylation conditions using $L^1$—$R^4$—$R^5$ where $L^1$ is hydroxyl. (See Kozai, *Chem. Pharm. Bull.*, 1999, 47(4), 574–575).

Method 3

From Triazole:

Compounds of Formula I can also be prepared from a substituted triazole as shown in Scheme 4. Accordingly, compounds of Formula 3, wherein $R^{14}$ is $NH_2$, $R^{13}$ is $C(O)NH_2$ and $R^{15}$ is H (commercially available), can be alkylated in the presence of a base such as KOH, NaOH, $K_2CO_3$, NaH, $Cs_2CO_3$, DBU etc. with/without the presence of halide such as NaI, KI, $(Bu)_3NI$ etc., and in a polar solvent such as DMF, THF, DMSO etc. using electrophiles such as $L^1$—$R^4$—$R^5$ where $L^1$ is a leaving group. Leaving groups include but are not limited to, e.g., halogen, triflate, tosylate, mesylate etc. to give compounds of Formula 6. The ring closure can be achieved using many methods reported in the literature (Alhede, *J. Org. Chem.*, 1991, 2139 and references cited therein) to give compounds of Formula I, wherein $R^1$ is OH. These compounds can be converted to the compounds of Formula I, wherein $R^1$ is Cl, using $POCl_3$ as described earlier. Alternately, we can also construct from Formula 3, wherein $R^{14}$ is —OH or halide, $R^{13}$ is —C(O)OEt by reacting with guanidine hydrochloride as described in Chowdhury, *J. Med. Chem.* 1999, 42, 4300.

Scheme 4

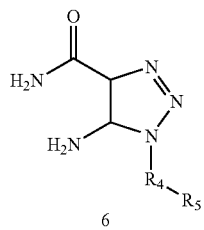

Preparation of electrophiles $L^1$—$R^4$—$R^5$ wherein $L_1$ is a leaving group and of nucleophiles $NH_2$—$R^4$—$R^5$.

Synthesis of benzyl type electrophile:

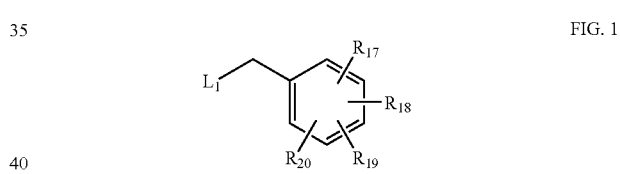

FIG. 1

The electrophiles can be prepared from the substituted benzene derivatives using various methods reported in the literature, see Jerry March, *Advanced Organic Chemistry*, 4th edition; Larock, *Comprehensive Organic Transformations*, 1989, VCH, New York. For example, compounds where $L^1$ is —Br can be prepared by reduction followed by halogenation of the benzoic acid or aldehyde derivatives. These benzyl derivatives can also be prepared by benzylic oxidation or benzylic halogenation. Further modification of the benzyl ring can be done before or after the triazolopurine alkylation step; for example halogenation was done both ways.

Synthesis of pyridyl methyl type electrophile:

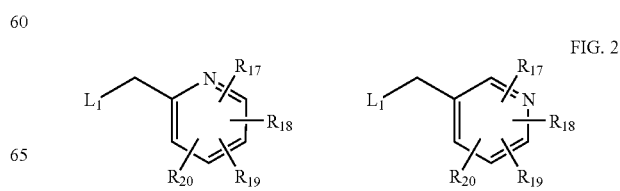

FIG. 2

-continued

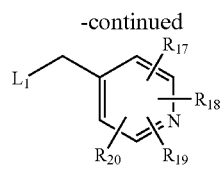

These compounds can be prepared from many methods reported in the literature. Morisawa et al. *J. Med. Chem.* 1974, 17, 1083; Klaus, W. et al. *J. Med. Chem.* 1992, 35, 438; Abramovitch, R. A.; Smith, E. M. "Pyridine-1-oxide in Pyridine and its Derivatives" in *The Chemistry of Heterocyclic Compounds*; Weissberger, A., Taylor, E. C., Eds.; John Wieley, New York, 1974, Pt. 2, pp 1–261; Jeromin, G. E. et al. *Chem. Ber.* 1987, 120, 649. Blanz, E. J., et al. *J. Med. Chem.* 1970, 13, 1124; Smith, Kline and French, EP 0184322, 1986; Abblard, J. et al. *Bull. Soc. Chim. Fr.* 1972, 2466; Fisher, B. E. et al. "The Structure of Isomaltol." *J Org Chem.* 1964, 29, 776. De Cat, A. et al. *Bull. Soc. Chim. Belg.* 1965, 74, 270; Looker, J. H. et al. *J. Org. Chem.* 1979, 44, 3407. Ackerman, J. F. Ph.D. Dissertation, University of Notre Dame, June, 1949. These methods can be applied to the synthesis of quinoline, and isoquinolines type compounds.

The compound $R^4$—$R^5$—$NH_2$ is obtained by treating. $R^4$—$R^5$-$L^1$ with ammonia at temperatures of 20–160° C. in a pressure vessel, wherein $L^1$ is leaving group such as chloride, bromide, tosylate, mesylate etc. using ammonia, or with sodium azide followed by hydrogenation.

Further Elaboration of the Ring Systems.

These modifications can be done at any stage depending upon the incompatibility of the functional groups present.

Functional Group Interconversions of $R^1$:

Compounds of Formula I, wherein $R^1$ is OH, can be converted to halides using standard conditions $POCl_3$, $POBr_3$ etc. with/without a base such as $Et_3N,N,N$-dimethylaniline, (i-$Pr$)$_2$NEt etc. and with/without a catalyst such as $BnEt_3N^+Cl^-$, in polar solvents such as $CH_3CN$, $CH_2Cl_2$ etc. Related methods include, but are not limited to, $SOCl_2$/DMF (M. J. Robins, *Can. J. Chem.* 1973, 12, 3161), $PPh_3/CCl_4$ (L. De Napoli, *J. Chem. Soc. Perkin Trans* 1, 1994, 923), HMPT/$CCl_4$ or HMPT/NBS (E. A. Veliz, *Tetrahedron Lett*, 2000, 41, 1695) or $PPh_3/I_2$ (X. Lin, *Org. Letters*, 2000, 2, 3497).

Compounds of Formula I, wherein $R^1$ is $NH_2$, can be converted to halides by a Balz-Schiemann (F) or Sandmeyer reaction (Cl, Br, I) by means of a nitrosylating agent ($NaNO_2/H^+$, $NOBF_4$, RONO) and a halogen donor ($BF_4^-$, $CuX_2$, $SbX_3$, where X is halogen).

Compounds of Formula I, wherein $R^1$ is alkyl can be prepared from compounds of Formula 4 where $R^1$ is halogen and trialkyl aluminum or dialkyl zinc (A. Holy, *J. Med. Chem.* 1999, 42, 2064).

Compounds of Formula I, wherein $R^1$ is a halide can be converted to compounds wherein $R^1$ is $NH_2$, OH, SH, $OR^8$, $SR^8$ with standard reagents, e.g. $NH_3$, NaOH, thiourea, $R^8O^-$, $R^8S^-$, with or without a catalyst (e.g. Pd, Ni, Cu, Lewis acid, $H^+$) (e.g. B. G. Ugarkar, *J. Med. Chem.* 2000, 43, 2883–2893 and 2894–2905).

Compounds of Formula I, wherein $R^1$ is halogen or another leaving group can be treated with ammonia to provide compounds of Formula I wherein $R^1$ is $NH_2$ (F. Seela, *Liebigs. Ann. Chem.* 1985, 315).

Functional Group Interconversions of $R^2$:

Compounds of Formula I, wherein $R^2$ is $NH_2$ can be temporarily protected, e.g. as an amide ($Ac_2O$, PivCl), a carbamate ($tBoc)_2O$) or amidine (DMF-DMA).

Compounds of Formula I, wherein $R^2$ is $NH_2$ can be converted to halides by a Balz-Schiemann (F) or Sandmeyer reaction (Cl, Br, I) by means of a nitrosylating agent ($NaNO_2/H^+$, $NOBF_4$, RONO) and a halogen donor ($BF_4^-$, $CuX_2$, $SbX_3$).

Compounds of Formula I, wherein $R^2$ is a halide can be converted to compounds wherein $R^2$ is $NH_2$, OH, SH, $OR^8$, $SR^8$ with standard reagents, e.g. $NH_3$, NaOH, thiourea, $R^8O^-$, $R^8S^-$, with or without a catalyst (e.g. Pd, Ni, Cu, Lewis acid, $H^+$).

Compounds of Formula I, wherein $R^2$ is SH can be converted to halides ($Br_2$). They can also be oxidized (e.g. $H_2O_2$) and treated with ammonia to give a $NH_2$ group (S. M. Bennett, *J. Med Chem.* 1990, 33, 2162).

Compounds of Formula I, wherein $R^2$ is a sulfide, e.g. MeS—, can be converted to a sulfone, e.g., $MeSO_2^-$, and displaced with a nucleophile, e.g. $NH_3$ or $NH_2$—$NH_2$, $N_3^-$, $CN^-$.

Compounds of Formula I, wherein $R^2$ is a sulfide, e.g. MeS—, can be converted to a sulfone, e.g., $MeSO_2^-$, and displaced with a nucleophile, e.g., $NH_3$ or $NH_2$-$NH_2$, $N_3^-$, $CN^-$.

Further Elaboration of $R^5$:

$R^5$, especially when it is aryl or heteroaryl, can be further modified as needed, for example by halogenation, nitration, palladium coupling of halogen, Friedel-Crafts alkylation/acylation, etc. or these modifications can also be done before alkylation, see Jerry March, *Advanced Organic Chemistry*. The heteroaromatic rings can also be oxidized to their corresponding N-oxides using various oxidizing agents such as $H_2O_2$, $O_3$, MCPBA etc. in polar solvents such as $CH_2Cl_2$, $CHCl_3$, $CF_3COOH$ etc. See Jerry March, *Advanced Organic Chemistry*, 4th edition, Chapter 19. Examples of modifications are suggested in Scheme 5.

Also, if $R^5$ is for instance a pyridine, it can be converted to a N-oxide either before or after alkylation.

Scheme 5

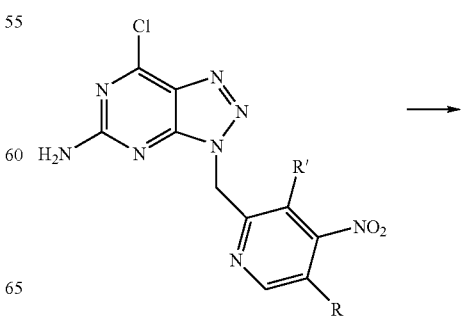

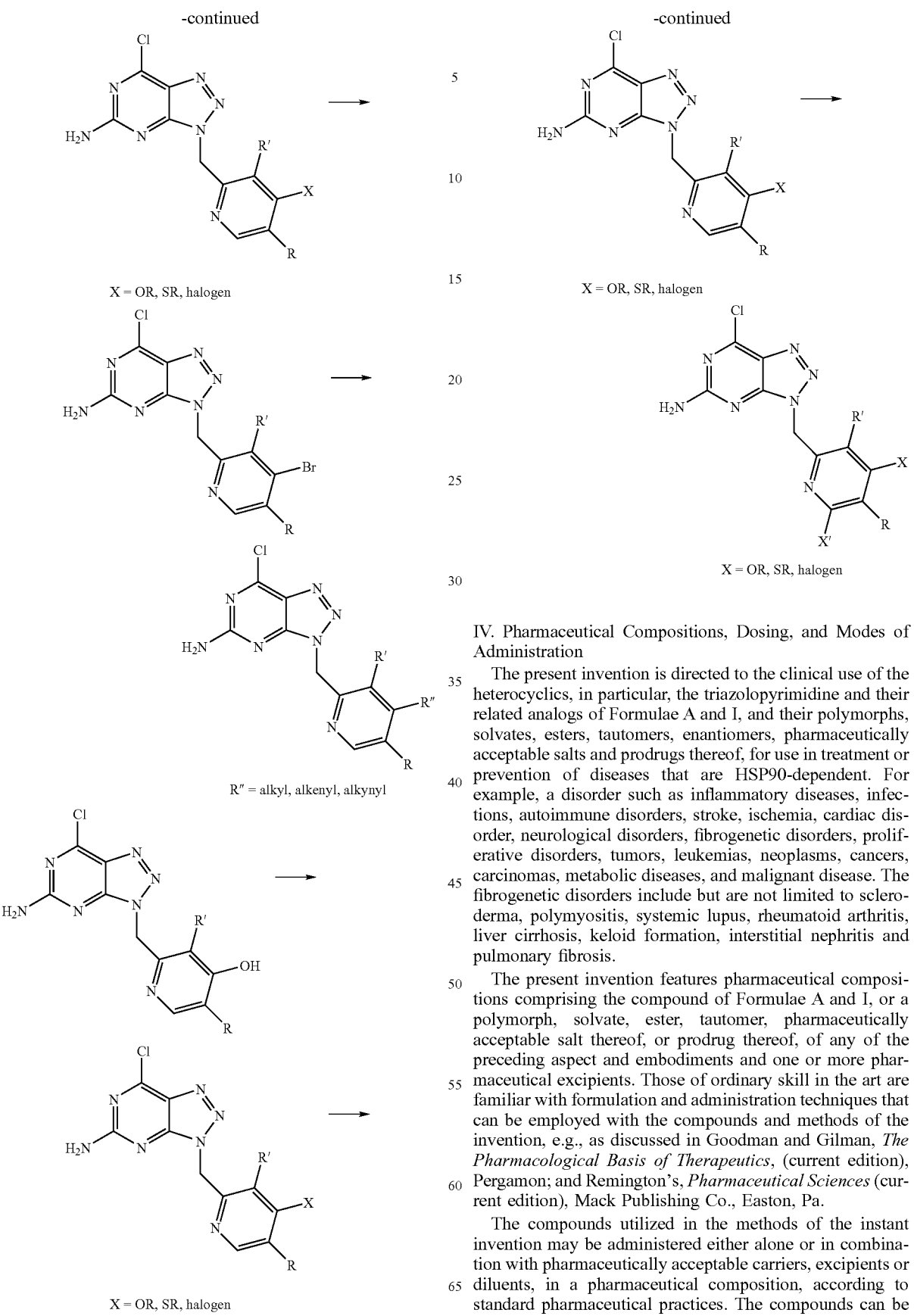

IV. Pharmaceutical Compositions, Dosing, and Modes of Administration

The present invention is directed to the clinical use of the heterocyclics, in particular, the triazolopyrimidine and their related analogs of Formulae A and I, and their polymorphs, solvates, esters, tautomers, enantiomers, pharmaceutically acceptable salts and prodrugs thereof, for use in treatment or prevention of diseases that are HSP90-dependent. For example, a disorder such as inflammatory diseases, infections, autoimmune disorders, stroke, ischemia, cardiac disorder, neurological disorders, fibrogenetic disorders, proliferative disorders, tumors, leukemias, neoplasms, cancers, carcinomas, metabolic diseases, and malignant disease. The fibrogenetic disorders include but are not limited to scleroderma, polymyositis, systemic lupus, rheumatoid arthritis, liver cirrhosis, keloid formation, interstitial nephritis and pulmonary fibrosis.

The present invention features pharmaceutical compositions comprising the compound of Formulae A and I, or a polymorph, solvate, ester, tautomer, pharmaceutically acceptable salt thereof, or prodrug thereof, of any of the preceding aspect and embodiments and one or more pharmaceutical excipients. Those of ordinary skill in the art are familiar with formulation and administration techniques that can be employed with the compounds and methods of the invention, e.g., as discussed in Goodman and Gilman, *The Pharmacological Basis of Therapeutics*, (current edition), Pergamon; and Remington's, *Pharmaceutical Sciences* (current edition), Mack Publishing Co., Easton, Pa.

The compounds utilized in the methods of the instant invention may be administered either alone or in combination with pharmaceutically acceptable carriers, excipients or diluents, in a pharmaceutical composition, according to standard pharmaceutical practices. The compounds can be administered orally or parenterally, including the intravenous, intramuscular, intraperitoneal, subcutaneous, rectal and topical routes of administration.

For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue.

Still further, the compounds or compositions of the invention can be delivered in a vesicle, e.g., a liposome (see, for example, Langer, Science 1990, 249, 1527–1533; Treat et al., *Liposomes in the Therapy of Infectious Disease and Cancer*, Lopez-Bernstein and Fidler, Ed., Liss, N.Y., pp. 353–365, 1989).

The compounds and pharmaceutical compositions used in the methods of the present invention can also be delivered in a controlled release system. In one embodiment, a pump may be used (see, Sefton, 1987, CRC Crit. Ref. Biomed. Eng. 14:201; Buchwald et al. *Surgery,* 1980, 88, 507; Saudek et al. *N. Engl. J. Med.* 1989, 321, (574). Additionally, a controlled release system can be placed in proximity of the therapeutic target. (See, Goodson, *Medical Applications of Controlled Release,* 1984, 2, 115–138).

The pharmaceutical compositions used in the methods of the instant invention can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachisd oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The compounds and pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods, compounds and compositions of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When a compound or composition of the invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer, for example, breast cancer. Administration typically occurs in an amount of between about 0.01 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 1000 mg of compound, and preferably includes, e.g., from about 1 mg to about 1000 mg. The quantity of active compound in a unit dose of preparation may be varied or adjusted from about 0.1 mg to 1000 mg, preferably from about 1 mg to 300 mg, more preferably 10 mg to 200 mg, according to the particular application. The amount administered will vary depending on the particular $IC_{50}$ value of the compound used and the judgment of the attending clinician taking into consideration factors such as health, weight, and age. In combinational applications in which the compound is not the sole active ingredient, it may be possible to administer lesser amounts of compound and still have therapeutic or prophylactic effect.

Preferably, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds and compositions of the present invention used in the methods of the present invention, and if applicable other chemotherapeutic agents and/or radiation therapy, will be regulated according to the judgment of the attending clinician (physician) considering such factors as age, condition and size of the patient as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the compounds of the invention need not be administered in the same pharmaceutical composition as a chemotherapeutic agent, and may, because of different physical and chemical characteristics, be administered by a different route. For example, the compounds/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound (and where appropriate, chemotherapeutic agent and/or radiation) will depend upon the diagnosis of the attending physicians and their judgment of the condition of the patient and the appropriate treatment protocol.

The compounds/compositions of the invention (and where appropriate chemotherapeutic agent and/or radiation) may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete.

Thus, in accordance with experience and knowledge, the practicing physician can modify each protocol for the administration of a compound/composition for treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

V. Assays for Determining HSP90 Binding and Downstream Effect

A variety of in vitro and in vivo assays are available to test the effect of the compounds of the invention on HSP90. HSP90 competitive binding assays and functional assays can be performed as known in the art substituting in the compounds of the invention. Chiosis et al. *Chemistry & Biology* 2001, 8, 289–299, describe some of the known ways in which this can be done. For example, competition binding assays using, e.g., geldanamycin or 17-AAG as a competitive binding inhibitor of HSP90 can be used to determine relative HSP90 affinity of the compounds of the invention by immobilizing the compound of interest or other competitive inhibitor on a gel or solid matrix, preincubating HSP90 with the other inhibitor, passing the preincubated mix over the gel or matrix, and then measuring the amount of HSP90 that retains or does not retain on the gel or matrix.

Downstream effects can also be evaluated based on the known effect of HSP90 inhibition on function and stability of various steroid receptors and signaling proteins including, e.g., Raf1 and HER2. Compounds of the present invention induce dose-dependent degradation of these molecules, which can be measured using standard techniques. Inhibition of HSP90 also results in up-regulation of HSP90 and related chaperone proteins that can similarly be measured. Antiproliferative activity on various cancer cell lines can also be measured, as can morphological and functional differentiation related to HSP90 inhibition.

Many different types of methods are known in the art for determining protein concentrations and measuring or predicting the level of proteins within cells and in fluid samples. Indirect techniques include nucleic acid hybridization and amplification using, e.g., polymerase chain reaction (PCR). These techniques are known to the person of skill and are discussed, e.g., in Sambrook, Fritsch & Maniatis *Molecular Cloning: A Laboratory Manual,* 2nd ed., Cold Spring Harbor Laboratory, Cold Spring Harbor, N.Y., 1989; Ausubel, et al. *Current Protocols in Molecular Biology*, John Wiley & Sons, NY, 1994, and, as specifically applied to the quantification, detection, and relative activity of HER2/Neu in patient samples, e.g., in U.S. Pat. Nos. 4,699,877, 4,918,162, 4,968,603, and 5,846,749. A brief discussion of two generic techniques that can be used follows.

The determination of whether cells overexpress or contain elevated levels of HER2 can be determined using well known antibody techniques such as immunoblotting, radio-immunoassays, western blotting, immunoprecipitation, enzyme-linked immunosorbant assays (ELISA), and derivative techniques that make use of antibodies directed against HER2. As an example, HER2 expression in breast cancer cells can be determined with the use of an immunohistochemical assay, such as the Dako Hercep™ test (Dako Corp., Carpinteria, Calif.). The Hercep™ test is an antibody staining assay designed to detect HER2 overexpression in tumor tissue specimens. This particular assay grades HER2 expression into four levels: 0, 1, 2, and 3, with level 3 representing the highest level of HER2 expression. Accurate quantitation can be enhanced by employing an Automated Cellular Imaging System (ACIS) as described, e.g., by Press, M. et al. *Modern Pathology* 2000, 13, 225A.

Antibodies, polyclonal or monoclonal, can be purchased from a variety of commercial suppliers, or may be manufactured using well-known methods, e.g., as described in Harlow et al. *Antibodies: A Laboratory Manual*, 2nd ed; Cold Spring Harbor Laboratory, Cold Spring Harbor, N.Y., 1988.

HER2 overexpression can also be determined at the nucleic acid level since there is a reported high correlation between overexpression of the HER2 protein and amplification of the gene that codes for it. One way to test this is by using RT-PCR. The genomic and cDNA sequences for HER2 are known. Specific DNA primers can be generated using standard, well-known techniques, and can then be used to amplify template already present in the cell. An example of this is described in Kurokawa, H. et al. *Cancer Res.* 2000, 60, 5887–5894. PCR can be standardized such that quantitative differences are observed as between normal and abnormal cells, e.g., cancerous and noncancerous cells. Well known methods employing, e.g., densitometry, can be used to quantitate and/or compare nucleic acid levels amplified using PCR.

Similarly, fluorescent in situ hybridization (FISH) assays and other assays can be used, e.g., Northern and/or Southern blotting. These rely on nucleic acid hybridization between the HER2 gene or mRNA and a corresponding nucleic acid probe that can be designed in the same or a similar way as for PCR primers, above. See, e.g., Mitchell M S, and Press M. F. *Oncol., Suppl.* 1999, 12, 108–116. For FISH, this nucleic acid probe can be conjugated to a fluorescent molecule, e.g., fluorescein and/or rhodamine, that preferably does not interfere with hybridization, and which fluorescence can later be measured following hybridization. See, e.g., Kurokawa, H et al, *Cancer Res.* 2000, 60, 5887–5894 (describing a specific nucleic acid probe having sequence 5'-FAM-NucleicAcid-TAMRA-p-3' sequence). ACIS-based approaches as described above can be employed to make the assay more quantitative (de la Torre-Bueno, J., et al. *Modern Pathology* 2000, 13, 221A).

Immuno and nucleic acid detection can also be directed against proteins other than HSP90 and HER2, which proteins are nevertheless affected in response to HSP90 inhibition.

The following examples are offered by way of illustration only and are not intended to be limiting of the full scope and spirit of the invention.

EXAMPLES

I. Materials and Methods

The chemical reagents used to create the novel products of the invention below are all available commercially, e.g., from Aldrich Chemical Co., Milwaukee, Wis., USA. Otherwise their preparation is facile and known to one of ordinary skill in the art, or it is referenced or described herein.

The final compounds were usually purified by preparative TLC (silica gel 60 Å, Whatman Partisil PK6F) or flash chromatography (silica gel 60 Å, EMD Chemicals) using EtOAc/hexane or MeOH/CH$_2$Cl$_2$ as eluents. Rf's were measured using silica gel TLC plates (silica gel 60 Å, EMD Chemicals). Analytical HPLC chromatograms were obtained using a C18 column (Agilent Zorbax 300SB-C18; 5 microns; 4.6 mm×150 mm). A gradient was applied between solvent A (0.1% TFA in H$_2$O) and solvent B (0.5% TFA in CH$_3$CN) increasing the proportion of A linearly from 5% (t=0) to 100% (t=7.00 min), with a constant flow rate of 1 mL/min. The samples were diluted to typically 0.1–1 mg/mL in MeOH or CH$_3$CN and the injection volumes were typically 10 μL. The column was not heated, and UV detection was effected at 254 nm. $^1$H-NMR spectra were recorded on a Bruker Avance 400 MHz spectrometer.

The chemical names were generated using the Beilstein Autonom 2.1 software.

II. General Procedures

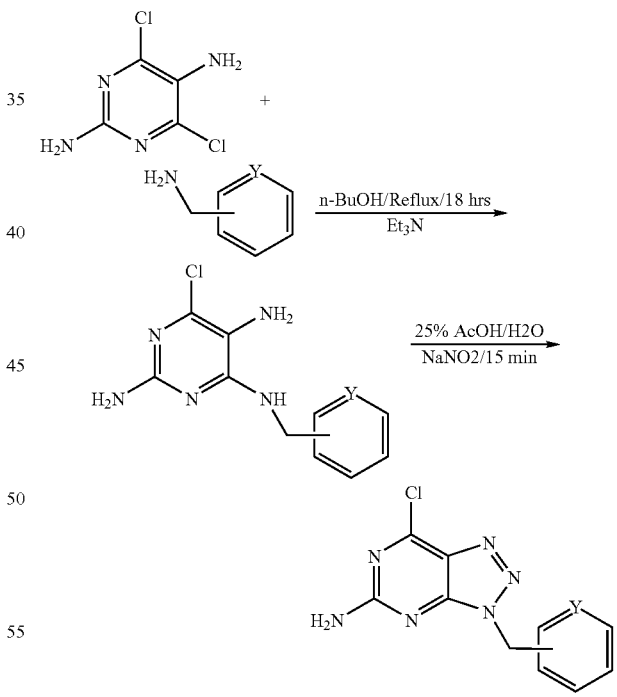

General Procedure 1: Displacement of Chlorine with Amines

*Ref:* *Helv. Chim Acta.* 1986, 69, 1602–1613; U.S. Pat. No. 5,917,042

A mixture of benzylamine derivative or aminomethylpyridine derivative (5.88 mmole, 2.1 equivalents), triethylamine (1 ml, 7.2 mmole) and 4,6-dichloro-pyrimidine-2,5-diamine (0.5 g, 2.8 mmole), was refluxed in n-BuOH or ethanol (10 mLs) for 3 to 18 hours. The mixture was cooled to room temperature and was extracted with $CH_2Cl_2$. The organic layer was washed with water and dried with $MgSO_4$ to afford the crude product. The pyridinyl derivatives were purified by chromatography (100% EtOAc-10% MeOH/EtOAc), whereas the benzyl derivatives were used without further purification.

General Procedure 2: Cyclization to Form Triazolopyrimidine Ring System

To a solution of 6-chloro-$N^4$-benzyl-pyrimidine-2,4,5-triamine derivatives or 6-chloro-$N^4$-pyridin-2-ylmethyl-pyrimidine-2,4,5-triamine derivatives (0.57 mmole) in 25% $HOAc/H_2O$, an aqueous solution of $NaNO_2$ (1.2 equivalents, 1 mL) was added dropwise at 0° C. The reaction mixture was stirred for 15 minutes at room temperature and filtered the crude product and purified by column chromatography using 75% EtOAc/Hexanes-100% EtOAc.

General Procedure 3: Aromatic Ring Halogenation

A mixture of 7-chloro-3-benzyl-3H-[1,2,3]triazolo[4,5-d]pyrimidin-5-ylamine derivatives (0.57 mmole) and NCS(N-chlorosuccinimide) or NBS (N-bromosuccinimide) or NIS (N-iodosuccinimide) (1.5 equivalents) in 10 mLs HOAc was stirred at 50° C. for 1 to 15 hours to afford the crude corresponding halogenated product which was purified by chromatography (50–75% EtOAc/Hexanes).

General Procedure 4: N-oxide Formation

A solution of the pyridine derivative (1 mmol) in dichloromethane or chloroform (5 mL) was cooled by means of an ice-bath, treated with m-CPBA (1.1 to 3 mmol) in three portions, and allowed to warm to r.t. The mixture was extracted with dichloromethane and washed with aqueous NaOH, followed by water. Drying ($Na_2SO_4$) and concentration afforded the pyridine N-oxide.

Example 1

7-Chloro-3-(4-methoxy-3,5-dimethylpyridin-2-yl)-3H-[1,2,3]triazolo[4,5-d]pyrimidin-5-ylamine Step 1: Synthesis of 2-aminomethyl-4-methoxy-3,5-dimethylpyridine A solution of 2-chloromethyl-4-methoxy-3,5-dimethylpyridine HCl (Aldrich 3.7 g, 16.6 mmole) in 7N $NH_3$/MeOH (Aldrich, 200 mLs) was refluxed in a steel bomb for 15 hours. Removed the solvent under reduced pressure, the residue was taken into 5% MeOH/$CH_2Cl_2$ and filtering it through a thin layer of silica gel afforded the product at 76% yield. HPLC RT was 2.850 min. $^1$HNMR ($CDCl_3$) δ 8.18 (s, 1H), 4.32 (s, 2H), 3.76 (s, 3H), 2.23 (s, 3H), 2.18 (s, 3H).

Step 2: Synthesis of 6-chloro-$N^4$-(4-methoxy-3,5-dimethyl-pyridin-2-ylmethyl)-pyrimidine-2,4,5-triamine A mixture of 4,6-dichloro-pyrimidine-2,5-diamine and 2-aminomethyl-4-methoxy-3,5-dimethyl-pyridine was heated to reflux in n-BuOH for 3 h, following the general procedure 1. HPLC RT was 3.597 min. $^1$HNMR ($CDCl_3$) δ 8.22 (s, 1H), 7.12 (br. t, 1H), 4.61 (s, 2H), 4.56–4.55 (d, 2H), 3.80 (s, 3H), 3.00 (s, 2H), 2.29 (s, 3H), 2.27 (s, 3H).

Step 3: Synthesis of 7-chloro-3-(4-methoxy-3,5-dimethyl-pyridin-2-ylmethyl)-3H-[1,2,3]triazolo[4,5-d]pyrimidin-5-ylamine A solution of 6-chloro-$N^4$-(4-methoxy-3,5-dimethyl-pyridin-2-ylmethyl)-pyrimidine-2,4,5-triamine was treated with a cold aqueous solution of $NaNO_2$, following the general procedure 2. HPLC RT was 3.597 min. $^1$HNMR ($CDCl_3$): δ 8.22 (s, 1H), 7.12 (broad t, 1H), 4.61 (s, 2H), 4.56–4.55 (d, 2H), 3.80 (s, 3H), 3.00 (s, 2H), 2.29 (s, 3H), 2.27 (s, 3H).

Example 2

7-Chloro-3-(4-methoxy-3,5-dimethyl-1-oxy-pyridin-2-yl)-3H-[1,2,3]triazolo[4,5-d]pyrimidin-5-ylamine The title compound was obtained by oxidation of 7-Chloro-3-(4-methoxy-3,5-dimethyl-pyridin-2-ylmethyl)-3H-[1,2,3]triazolo[4,5-d]pyrimidin-5-ylamine (see Example 1) with m-CPBA (m-chloroperoxybenzoic acid) in methylene chloride, following the general procedure 4. HPLC RT was 4.780 min. $^1$HNMR ($CDCl_3$) δ 8.02 (s, 1H), 5.90 (s, 2H), 5.61 (s, 2H), 3.81 (s, 3H), 2.54 (s, 3H), 2.25(s, 3H).

Example 3

7-Chloro-3-(4-methoxy-benzyl)-3H-[1,2,3]triazolo[4,5-d]pyrimidin-5-ylamine

Step 1: Synthesis of 6-chloro-$N^4$-(4-methoxy-benzyl)-pyrimidine-2,4,5-triamine:

A mixture of 4,6-dichloro-pyrimidine-2,5-diamine and 1-aminomethyl-4-methoxybenzene was refluxed in n-BuOH for 15 h, following the general procedure 1. HPLC RT was 4.675 min. $^1$HNMR ($CDCl_3$) δ 7.29–7.27 (d, 2H), 6.91–6.89 (d, 2H), 5.62 (br. t, 1H) 4.67 (s, 2H), 4.56–4.54 (d, 2H), 3.84 (s, 3H), 2.74 (s, 2H).

Step 2: Synthesis of 7-chloro-3-(4-methoxy-benzyl)-3H-[1,2,3]triazolo[4,5-d]pyrimidin-5-ylamine A solution of 6-chloro-$N^4$-(4-methoxy-phenyl)-pyrimidine-2,4,5-triamine was treated with a cold aqueous solution of $NaNO_2$, following the general procedure 2. HPLC RT was 5.784 min. $^1$HNMR ($CDCl_3$): δ 7.37–7.35 (d, 2H), 6.86–6.84 (d, 2H), 5.57 (s, 2H), 5.39 (s, 2H), 3.78 (s, 3H).

Example 4

Synthesis of 7-chloro-3-pyridin-2-ylmethyl-3H-[1,2,3]triazolo[4,5-d]pyrimidin-5-ylamine Step 1: 6-chloro-$N^4$-pyridin-2-ylmethyl-pyrimidine-2,4,5-triamine A mixture of 4,6-dichloro-pyrimidine-2,5-diamine and 2-aminomethyl-pyridine was refluxed in n-BuOH for 15 h, following the general procedure 1. HPLC RT was 2.573 min. $^1$HNMR ($CDCl_3$) δ 8.60–8.59 (m, 1H), 7.69–7.66 (m, 1H), 7.31–7.29 (m, 1H), 7.25–7.20 (m, 1H), 6.55 (br. t, 1H) 4.63 (s, 2H), 4.73–4.71 (d, 2H), 1.84 (s, 2H).

Step 2: Synthesis of 7-chloro-3-pyridin-2-ylmethyl-3H-[1,2,3]triazolo[4,5-d]pyrimidin-5-ylamine A solution of 6-chloro-N$^4$-pyridin-2-ylmethyl-pyrimidine-2,4,5-triamine was treated with a cold aqueous solution of NaNO$_2$, following the general procedure 2. $^1$HNMR (CDCl$_3$): δ 8.60–8.59 (m, 1H), 7.71–7.67(m, 1H), 7.29–7.25 (m, 1H), 7.22–7.20 (m, 1H), 5.81 (s, 2H), 5.48 (s, 2H).

Example 5

Synthesis of 7-chloro-3-(3,4,5-trimethoxy-benzyl)-3H-[1,2,3]triazolo[4,5-d]pyrimidin-5-ylamine

Step 1: 6-chloro-N-4-(3,4,5-trimethoxy-benzyl)-pyrimidine-2,4,5-triamine

A mixture of 4,6-dichloro-pyrimidine-2,5-diamine and 1-aminomethyl-3,4-5-trimethoxybenzene in n-BuOH for 15 h, following the general procedure 1. HPLC RT was 4.458 min. $^1$HNMR (CDCl$_3$) δ 6.58 (s, 2H), 5.62 (br. t, 1H) 4.72 (s, 2H), 4.56–4.54 (d, 2H), 3.88 (s, 6H), 3.86 (s, 3H), 2.77 (s, 2H).

Step 2: Synthesis of 7-chloro-3-(3,4,5-trimethoxy-benzyl)-3H-[1,2,3]triazolo[4,5-d]pyrimidin-5-ylamine)

A solution of 6-chloro-N$^4$-(3,4,5-trimethoxy-benzyl)-pyrimidine-2,4,5-triamine was treated with a cold aqueous solution of NaNO$_2$, following the general procedure 2. HPLC RT was 5.755 min. $^1$HNMR (CDCl$_3$): δ 6.66 (s, 2H), 5.55 (s, 2H), 5.42 (s, 2H), 3.83 (s, 3H), 3.80 (s, 6H).

Example 6

Synthesis of 7-chloro-3-(2-chloro-3,4,5-trimethoxy-benzyl)-3H-[1,2,3]triazolo[4,5-d]pyrimidin-5-ylamine Chlorination of 7-chloro-3-(3,4,5-trimethoxy-benzyl)-3H-[1,2,3]triazolo[4,5-d]pyrimidin-5-ylamine) (CF 2137) with NCS (1.5 equivalents) was done following the general procedure 3 to give the title compound: HPLC RT was 6.244 min. $^1$HNMR (CDCl$_3$): δ 6.53 (s, 1H), 5.70 (s, 2H), 5.48 (s, 2H), 3.89 (s, 3H), 3.87 (s, 3H), 3.75 (s, 3H).

Example 7

7-Chloro-3-(2,6-dichloro-3,4,5-trimethoxy-benzyl)-3H-[1,2,3]triazolo[4,5-d]pyrimidin-5-ylamine Chlorination of 7-chloro-3-(3,4,5-trimethoxy-benzyl)-3H-[1,2,3]triazolo[4,5-d]pyrimidin-5-ylamine) with NCS (1.5 equivalents) was done following the general procedure 3 to give the title compound: HPLC RT was 6.616 min. $^1$HNMR (CDCl$_3$): δ 5.81 (s, 2H), 5.47 (s, 2H), 3.97 (s, 3H), 3.90(s, 6H).

Example 8

Synthesis of 7-chloro-3-(2-bromo-3,4,5-trimethoxy-benzyl)-3H-[1,2,3]triazolo[4,5-d]pyrimidin-5-ylamine Bromination of 7-chloro-3-(3,4,5-trimethoxy-benzyl)-3H-[1,2,3]triazolo[4,5-d]pyrimidin-5-ylamine) with NBS (1.5 equivalents) was done following the general procedure 3 to give the title compound: HPLC RT was 6.541 min. $^1$HNMR (CDCl$_3$): δ 6.52 (s, 1H), 5.74(s, 2H), 5.46 (s, 2H), 3.93 (s, 3H), 3.89 (s, 3H), 3.76 (s, 3H).

Example 9

7-Chloro-3-(2,6-dibromo-3,4,5-trimethoxy-benzyl)-3H-[1,2,3]triazolo[4,5-d]pyrimidin-5-ylamine Bromination of 7-chloro-3-(3,4,5-trimethoxy-benzyl)-3H-[1,2,3]triazolo[4,5-d]pyrimidin-5-ylamine) with NBS (1.5 equivalents) was done following the general procedure 3 to give the title compound: HPLC RT was 6.923 min. $^1$HNMR (CDCl$_3$): δ 5.91 (s, 2H), 5.51 (s, 2H), 3.99 (s, 3H), 3.93(s, 6H).

Example 10

Synthesis of 7-chloro-3-(2-iodo-3,4,5-trimethoxy-benzyl)-3H-[1,2,3]triazolo [4,5-d]pyrimidin-5-ylamine The title compound was obtained from iodination of 7-chloro-3-(3,4,5-trimethoxy-benzyl)-3H-[1,2,3]triazolo[4,5-d]pyrimidin-5-ylamine) with NIS (1.5 equivalents) following the general procedure 3. HPLC RT was 6.497 min. $^1$HNMR (CDCl$_3$): δ 6.47 (s, 1H), 5.73(s, 2H), 5.44 (s, 2H), 3.92 (s, 3H), 3.88 (s, 3H), 3.73 (s, 3H).

Example 11

Synthesis of 7-chloro-3-(3,5-dimethoxy-benzyl)-3H-[1,2,3]triazolo[4,5-d]pyrimidin-5-ylamine

Step 1: 6-chloro-N$^4$-(3,5-dimethoxy-benzyl)-pyrimidine-2,4,5-triamine

The title compound was obtained from a mixture of 4,6-dichloro-pyrimidine-2,5-diamine and 1-aminomethyl-3,5-dimethoxybenzene in n-BuOH for 15 h, following the general procedure 1. HPLC RT was 4.835 min. $^1$HNMR (CDCl$_3$) δ 6.46–6.47 (d, 2H), 6.38–6.37(d, 1H), 5.67 (br. t, 1H) 4.63 (s, 2H), 4.53–4.52 (d, 2H), 3.81 (s, 6H), 2.72 (s, 2H).

Step 2: Synthesis of 7-chloro-3-(3,5-dimethoxy-benzyl)-3H-[1,2,3]triazolo[4,5-d]pyrimidin-5-ylamin A solution of 6-chloro-N$^4$-(3,5-dimethoxy-benzyl)-pyrimidine-2,4,5-triamine was treated with a cold aqueous solution of NaNO$_2$, following the general procedure 2. HPLC RT was 6.185 min. $^1$HNMR (CDCl$_3$): δ 6.54–6.53 (d, 2H), 6.41–6.40 (d, 1H), 5.58 (s, 2H), 5.54 (s, 2H), 3.78 (s, 6H).

Example 12

Synthesis of 7-chloro-3-(2-chloro-3,5-dimethoxy-benzyl)-3H-[1,2,3]triazolo[4,5-d]pyrimidin-5-ylamine The title compound was obtained by chlorination of 7-chloro-3-(3,5-dimethoxy-benzyl)-3H-[1,2,3]triazolo[4,5-d]pyrimidin-5-ylamine) with NCS (1.5 equivalents) in acetic acid at 50° C. for 1 h, following the general procedure 3. HPLC RT was 6.467 min. $^1$HNMR (CDCl$_3$): δ 6.50–6.49 (d, 1H), 6.18–6.17 (d, 1H), 5.77(s, 2H), 5.44 (s, 2H), 3.91 (s, 3H), 3.72 (s, 3H).

Example 13

Synthesis of 7-chloro-3-(2-bromo-3,5-dimethoxy-benzyl)-3H-[1,2,3]triazolo[4,5-d]pyrimidin-5-ylamine The title compound was obtained by bromination of 7-chloro-3-(3,5-dimethoxy-benzyl)-3H-[1,2,3]triazolo[4,5-d]pyrimidin-5-ylamine) with NBS (1.5 equivalents) in acetic acid at 50° C. during 1 h, following the general procedure 3. HPLC RT was 6.573 min. $^1$HNMR (d$_6$-DMSO): δ 7.74 (s, 2H), 6.70–6.69 (d, 1H), 6.23–6.22 (d, 1H), 5.63(s, 2H), 3.87 (s, 3H), 3.71 (s, 3H).

Example 14

Synthesis of 7-chloro-3-(2-iodo-3,5-dimethoxy-benzyl)-3H-[1,2,3]triazolo[4,5-d]pyrimidin-5-ylamine The title compound was obtained by iodination of 7-chloro-3-(3,5-dimethoxy-benzyl)-3H-[1,2,3]triazolo[4,5-d]pyrimidin-5-ylamine) with NIS (1.5 equivalents) in acetic acid at 50° C. during 1 h, following the general procedure 3. HPLC RT was 6.739 min. $^1$HNMR (d$_6$-DMSO): δ 7.75 (s, 2H), 6.61–6.60 (d, 1H), 6.15–6.14 (d, 1H), 5.58 (s, 2H), 3.86 (s, 3H), 3.70 (s, 3H).

Example 15

Synthesis of 7-Chloro-3-(2,5-dimethoxy-benzyl)-3H-[1,2,3]triazolo[4,5-d]pyrimidin-5-ylamine

Step 1: 6-chloro-N$^4$-(2,5-dimethoxy-benzyl)-pyrimidine-2,4,5-triamine

The title compound was obtained from a mixture of 4,6-dichloro-pyrimidine-2,5-diamine and 1-aminomethyl-2,5-dimethoxybenzene in n-BuOH for 15 h, following the general procedure 1. HPLC RT was 4.601 min. $^1$HNMR (CDCl$_3$) δ 6.91–6.90 (d, 1H), 6.82–6.80(m, 2H), 5.82 (br. t, 1H) 4.62 (s, 2H), 4.59–4.58 (d, 2H), 3.85 (s, 3H), 2.78 (s, 3H), 2.75 (s, 2H).

Step 2: Synthesis of 7-chloro-3-(2,5-dimethoxy-benzyl)-3H-[1,2,3]triazolo[4,5-d]pyrimidin-5-ylamine A solution of 6-chloro-N$^4$-(2,5-dimethoxy-benzyl)-pyrimidine-2,4,5-triamine was treated with a cold aqueous solution of NaNO$_2$, following the general procedure 2. HPLC RT was 6.130 min. $^1$HNMR (CDCl$_3$): δ 6.84–6.83 (m, 2H), 6.64–6.63 (d, 1H), 5.67 (s, 2H), 5.54 (s, 2H), 3.83 (s, 3H), 3.73 (s, 3H).

Example 16

Synthesis of 7-chloro-3-(4-bromo-2,5-dimethoxy-benzyl)-3H-[1,2,3]triazolo[4,5-d]pyrimidin-5-ylamine The title compound was obtained by bromination of 7-chloro-3-(2,5-dimethoxy-benzyl)-3H-[1,2,3]triazolo[4,5-d]pyrimidin-5-ylamine) with NBS (1.5 equivalents) in acetic acid at 50° C. during 1 h, following the general procedure 3. HPLC RT was 6.438 min. $^1$HNMR (CDCl$_3$): δ 7.11 (s, 1H), 6.80 (s, 1H), 5.63 (s, 2H), 5.57 (s, 2H), 3.82 (s, 3H), 3.79 (s, 3H).

Example 17

Synthesis of 7-chloro-3-(3-chloro-2,5-dimethoxy-benzyl)-3H-[1,2,3]triazolo[4,5-d]pyrimidin-5-ylamine The title compound was obtained by chlorination of 7-chloro-3-(2,5-dimethoxy-benzyl)-3H-[1,2,3]triazolo[4,5-d]pyrimidin-5-ylamine) with NCS (1.5 equivalents) in acetic acid at 50° C. during 1 h, following the general procedure 3. HPLC RT was 6.392 min. $^1$HNMR (CDCl$_3$): δ 6.91–6.90 (d, 1H), 6.67–6.66 (d, 1H), 5.70 (s, 2H), 5.43(s, 2H), 3.92 (s, 3H), 3.73 (s, 3H).

BIOLOGY EXAMPLES

Example A rHSP90 Competitive Binding Assay

Five microgram of purified rHSP90 protein (Stressgen, BC, Canada, #SPP-770) in phosphated buffered saline (PBS) was coated on 96 well plates by incubating overnight at 4° C. Unbound protein was removed and the coated wells were washed twice with 200 μL PBS. DMSO controls (considered as untreated samples) or test compounds were then added at 100–30–10–3–1–0.3 μM dilutions (in PBS), the plates mixed for 30 seconds on the plate shaker, and then incubated for 60 min. at 37° C. The wells were washed twice with 200 μL PBS, and 10 μM biotinylated-geldanamycin (biotin-GM) was added and incubated for 60 min. at 37° C. The wells were washed again twice with 200 μL PBS, before the addition of 201 g/mL streptavidin-phycoerythrin (streptavidin-PE) (Molecular Probes, Eugene, Oreg.) and incubation for 60 min. at 37° C. The wells were washed again twice with 200 μL PBS. Relative fluorescence units (RFU) was measured using a SpectraMax Gemini XS Spectrofluorometer (Molecular Devices, Sunnyvale, Calif.) with an excitation at 485 nm and emission at 580 nm; data was acquired using SOFTmax®PRO software (Molecular Devices Corporation, Sunnyvale, Calif.). The background was defined as the RFU generated from wells that were not coated with HSP90 but were treated with the biotin-GM and streptavidin-PE. The background measurements were substrated from each sample treated with biotin-GM and streptavidin-PE measurements before other computation. Percent inhibition of binding for each sample was calculated from the background subtracted values as follows:

% binding inhibition=[RFU untreated−RFU treated]/ RFU untreated]×100.

Example B

Cell Lysate Binding Assay

MCF7 breast carcinoma cell lysates were prepared by douncing in lysing buffer (20 mM HEPES, pH 7.3, 1 mM EDTA, 5 mM $MgCl_2$, 100 mM KCl), and then incubated with or without test compound for 30 mins at 4° C., followed by incubation with biotin-GM linked to BioMag™ streptavidin magnetic beads (Qiagen) for 1 hr at 4° C. The tubes were placed on a magnetic rack, and the unbound supernatant removed. The magnetic beads were washed three times in lysis buffer and boiled for 5 mins at 95° C. in SDS-PAGE sample buffer. Samples were analyzed on SDS protein gels, and Western blots done for rHSP90. Bands in the Western Blots were quantitated using the Bio-rad Fluor-S MultiImager, and the % inhibition of binding of rHSP90 to the biotin-GM was calculated.

The lysate binding ability of selected compounds of the invention based on the above assay is summarized in Table 2. The $IC_{50}$ reported is the concentration of test compound needed to achieve 50% inhibition of the biotin-GM binding to rHSP90 in the MCF7 cell lysates.

Example C

HER2 Degradation Assay

MCF7 breast carcinoma cells (ATCC) were grown in Dulbecco's modified Eagle's medium (DMEM) containing 10% fetal bovine serum (FBS) and 10 mM HEPES, and plated in 24 well plates (50% confluent). Twenty-four hrs later (cells are 65–70% confluent), test compounds were added and incubated overnight for 16 h. For the less potent compounds, the amounts added were 100 µM, 30 µM, 10 µM and 1 µM, and for more potent compounds, the amounts added were 1 µM, 0.3 µM, 0.1 µM, 0.03 µM, 0.01 µM and 0.003 µM. The wells were washed with 1 mL phosphate buffered saline (PBS), and 200 µL trypsin was added to each well. After trypsinization was complete, 50 µL of FBS was added to each well. Then 200 µL cells was transferred to 96 well plates. The cells were pipetted up and down to obtain a single cell suspension. The plates were centrifuged at 2,500 rpm for 1 min using a Sorvall Legend RT™ tabletop centrifuge (Kendro Laboratory Products, Asheville, N.C.). The cells were then washed once in PBS containing 0.2% BSA and 0.2% sodium azide (BA buffer). Phycoerythrin (PE) conjugated anti HER2/Neu antibody (Becton Dickinson, #340552), or PE conjugated anti-keyhole limpet hemacyanin [KLH] (Becton Dickinson, #340761) control antibody was added at a dilution of 1:20 and 1:40 respectively (final concentration was 1 µg/mL) and the cells were pipeted up and down to form a single cell suspension, and incubated for 15 mins. The cells were washed twice with 200 µL BA buffer, and resuspended in 200 µL BA buffer, and transferred to FACSCAN tubes with an additional 250 µL BA buffer. Samples were analyzed using a FACSCalibur™ flow cytometer (Becton Dickinson, San Jose, Calif.) equipped with Argon-ion laser that emits 15 mW of 488 nm light for excitation of the PE fluorochrome. 10,000 events were collected per sample. A fluorescence histogram was generated and the mean fluorescence intensity (MFI) of each sample was determined using Cellquest software. The background was defined as the MFI generated from cells incubated with control IgG-PE, and was subtracted from each sample stained with the HER2/Neu antibody. Cells incubated with DMSO was always done as untreated controls since the compounds were resuspended in DMSO. Percent degradation of HER2 was calculated as follows:

% HER2 degraded=[(MFI untreated cells−MFI treated cells)/MFI untreated cell]×100

The HER2 degradation ability of selected compounds of the invention based on this assay is summarized in Table 2. $IC_{50}$ is defined as the concentration at which there was 50% degradation of the HER2/Neu protein.

Example D

MTS Assay

MTS assays measures the cytotoxicity of geldanamycin derivatives. MTS (3-(4,5-dimethylthiazol-2-yl)-5-(3-carboxymethoxyphenyl)-2-(4-sulfophenyl)-2H-tetrazolium is a tetrazolium dye that is converted to a formazan product by dehydrogenase enzymes of metabolically active cells (Corey, A. et al. "Use of an aqueous soluble tetrazolium/ formazan assay for cell growth assays in culture," *Cancer Commun.* 1991, 3, 207–212). Cells were seeded in 96 well plates at 2000 cells/well and allowed to adhere overnight in Dulbecco's modified Eagle's medium supplemented with 10% fetal bovine serum. The final culture volume was 100 µl. Viable cell number was determined by using the Celltiter 96 $AQ_{ueous}$ Non-radioactive Cell Proliferation Assay (Promega, Madison Wis.). The MTS/PMS (phenazine methosulfate) solution was mixed at a ratio of 20:1, and 20 µL was added per well to 100 µl of culture medium. After 2–4 hours, the formation of the formazan product was measured at 490 nm absorbance using a multiwell plate spectrophotometer. Background was determined by measuring the Abs 490 nm of cell culture medium and MTS-PMS in the absence of cells and was subtracted from all values. Percent viable cells was calculated as follows:

% viable cells=(Abs at 490 nm treated cells/Abs at 490 nm untreated cells)×100

The effect of selected compounds of the invention on MCF7 breast carcinoma cells according to the MTS assay is summarized in Table 2. $IC_{50}$ was defined as the concentration of the compound which gave rise to 50% viable cell number.

TABLE 2

Biological Activities of Selected Compounds of Formula I

Formula 1

| S.No. | Ex.# | Structure | HER2 IC$_{50}$ (μM) | MTS IC$_{50}$ (μM) |
|---|---|---|---|---|
| 1 | 5 | (7-Cl, 5-NH$_2$ triazolopyrimidine with 3,4,5-trimethoxybenzylidene) | 15.0 | ND |
| 2 | 1 | (7-Cl, 5-NH$_2$ triazolopyrimidine with 4-methoxy-3,5-dimethylpyridin-2-ylmethyl) | 0.4 | 8.0 |
| 3 | 7 | (7-Cl, 5-NH$_2$ triazolopyrimidine with 2,6-dichloro-3,4,5-trimethoxybenzyl) | 4.0 | ND |
| 4 | 6 | (7-Cl, 5-NH$_2$ triazolopyrimidine with 3-chloro-4,5-dimethoxy... benzyl) | 12.0 | ND |

TABLE 2-continued
Biological Activities of Selected Compounds of Formula I
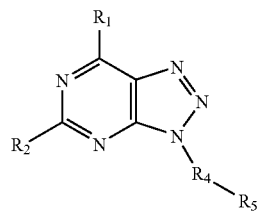
Formula 1
| S.No. | Ex.# | Structure | HER2 IC$_{50}$ (µM) | MTS IC$_{50}$ (µM) |
|---|---|---|---|---|
| 5 | 9 | 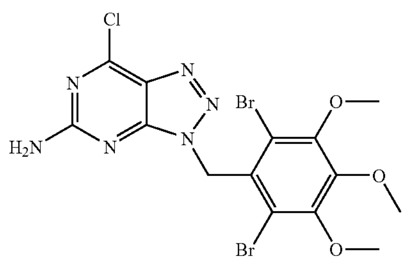 | 6.3 | ND |
| 6 | 8 | 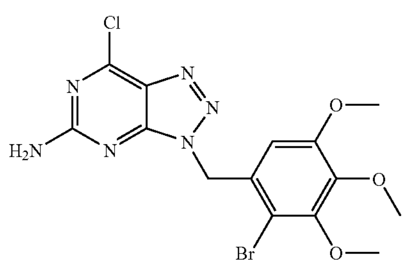 | 6.5 | ND |
| 7 | 10 | 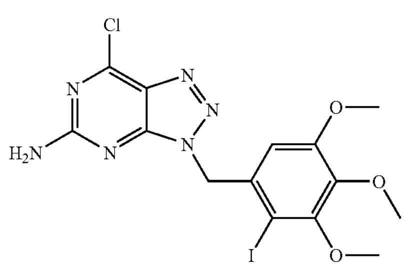 | 10.0 | ND |
| 8 | 12 | 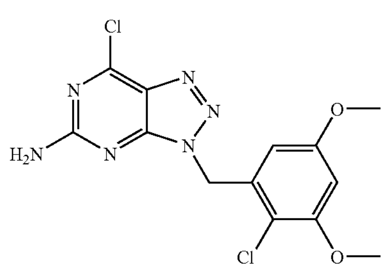 | 8.5 | ND |

TABLE 2-continued

Biological Activities of Selected Compounds of Formula I

Formula 1

| S.No. | Ex.# | Structure | HER2 IC$_{50}$ (μM) | MTS IC$_{50}$ (μM) |
|---|---|---|---|---|
| 9 | 13 | (Cl, H₂N-pyrimidotriazole, N-CH₂-benzyl with OMe, Br, OMe) | 16.0 | ND |
| 10 | 16 | (Cl, H₂N-pyrimidotriazole, N-CH₂-benzyl with OMe, Br, OMe) | 22.0 | ND |
| 11 | 17 | (Cl, H₂N-pyrimidotriazole, N-CH₂-benzyl with OMe, Cl, OMe) | 19.0 | ND |
| 12 | 2 | (Cl, H₂N-pyrimidotriazole, N-CH₂-pyridine N-oxide with Me, OMe, Me) | 0.5 | ND |

ND = not determined

The foregoing examples are not limiting and are merely illustrative of various aspects and embodiment of the present invention. All documents cited herein are indicative of the levels of skill in the art to which the invention pertains and are incorporated by reference herein in their entireties. None, however, is admitted to be prior art.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the sprint of the invention, as defined by the scope of the claims.

The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, e.g., genuses, those skilled in the art will recognize that the invention is also thereby described in terms of any individual member or subgroup of members of the Markush group or subgenus, and exclusions of individual members as appropriate, e.g., by proviso.

Other embodiments are within the following claims.

What is claimed is:

1. A compound represented by Formula I, or a polymorph, ester, tautomer, enantiomer, diastereomer, pharmaceutically acceptable salt or prodrug thereof,

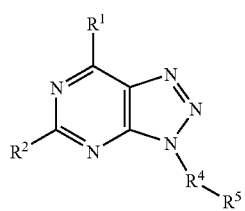

I wherein:
$R^1$ is halogen, $-OR^{11}$, $-SR^{11}$ or lower alkyl;
$R^2$ is $-NHR^8$;
$R^4$ is $-CHR^{12}-$, $-C(O)-$, $-C(S)-$, $-S(O)-$ or $-SO_2-$;
$R^5$ is aryl, heteroaryl, alicyclic, or heterocyclic, wherein:
the aryl group is substituted with 4 to 5 substituents,
the heteroaryl group is substituted with 3 to 5 substituents,
the alicyclic group is substituted with 3 to 5 substituents,
the heterocyclic group is substituted with 3 to 5 substituents, and
the substituents are selected from the group consisting of halogen, lower alkyl, lower alkenyl, lower alkynyl, $-SR^8$, $-OR^8$, $-CN$, $-C(O)OH$, $-C(O)R^9$, $-NO_2$, $-NR^8R^{10}$, lower aryl, heteroaryl, alicyclic, lower heterocyclic, arylalkyl, heteroarylalkyl, amino, alkylamino, dialkylamino, oxo, perhaloalkyl, perhaloalkoxy, perhaloacyl, guanidinyl, pyridinyl, thiophenyl, furanyl, indolyl, and indazolyl, wherein $R^8$ and $R^{10}$ taken together with the N to which they are attached optionally form a ring of 3–7 ring atoms and 1–3 of the ring atoms are heteroatoms selected from the group of O, S and N;
$R^8$ is hydrogen, lower alkyl, lower alkenyl, lower alkynyl, lower aryl, lower heteroaryl, or $-C(O)R^9$;
$R^9$ is H, lower alkyl, lower alkenyl, lower alkynyl, lower aryl, lower heteroaryl, $-NR^{10}R^{10}$, or $-OR^{11}$, wherein $R^{10}$ and $R^{10}$ taken together optionally form a ring of 3–7 ring atoms and optionally 1–3 of the ring atoms are heteroatoms selected from the group of O, S and N;
$R^{10}$ is hydrogen, lower alkyl, lower heteroaryl, lower aryl, lower alkenyl, or lower alkynyl,
$R^{11}$ is lower alkyl, lower alkenyl, lower alkynyl, lower heteroaryl or lower aryl; and
$R^{12}$ is hydrogen or lower alkyl;
provided that when $R^5$ is alicyclic, the ring system does not contain any tetra-substituted ring carbons.

2. The compound of claim 1, or a polymorph, ester, tautomer, enantiomer, diastereomer, pharmaceutically acceptable salt or prodrug thereof, wherein each of said aryl, heteroaryl, alicyclic or heterocyclic group is monocyclic or bicyclic.

3. The compound of claim 1, or a polymorph, ester, tautomer, enantiomer, diastereomer, pharmaceutically acceptable salt or prodrug thereof wherein:
$R^1$ is halogen; and
$R^2$ is $-NHR^8$, where $R^8$ is hydrogen or $-C(O)R$.

4. The compound of claim 1, or a polymorph, ester, tautomer, enantiomer, pharmaceutically acceptable salt or prodrug thereof, wherein:
$R^1$ is chioro or bromo,
$R^2$ is $-NHR^8$, where $R^8$ is hydrogen or $-C(O)R^9$; and
$R^4$ $-CHR^{12}-$.

5. The compound of claim 1, or a polymorph, ester, tautomer, enantiomer, pharmaceutically acceptable salt or prodrug thereof, wherein:
$R^2$ is $-NHR^8$, where $R^8$ is hydrogen or $-C(O)R^9$; and
$R^4$ is $-CH_2-$.

6. The compound of claim 1, or a polymorph, ester, tautomer, enantiomer, pharmaceutically acceptable salt or prodrug thereof, wherein:
$R^1$ is chloro or bromo;
$R^2$ is $-NH_2$,
$R^4$ is $-CH_2-$; and
$R^5$ is aryl or heteroaryl, wherein each of the aryl and heteroaryl is monocyclic or bicyclic and the aryl is substituted with 4 or 5 substituents and the heteroaryl is substituted with 3 to 5 substituents.

7. The compound of claim 6, or a polymorph, ester, tautomer, enantiomer, pharmaceutically acceptable salt or prodrug thereof, wherein $R^1$ is chloro or bromo, $R^2$ is $-NH_2$, and $R^5$ is a phenyl having at least four substituents.

8. The compound of claim 6, or a polymorph, ester, tautomer, enantiomer, pharmaceutically acceptable salt or prodrug thereof, wherein $R^1$ is chioro or bromo, $R^2$ is $-NH_2$ and $R^5$ is a pyridyl having at least three substituents.

9. The compound of claim 6, or a polymorph, tautomer, enantiomer, pharmaceutically acceptable salt or prodrug thereof, wherein $R^1$ is chloro or bromo, $R^2$ is —$NH_2$, and $R^5$ is 1-oxy-pyridyl (N-oxy-pyridyl) having at least three substituents.

10. The compound of claim 6, wherein the compound is a member selected from the group below, or a polymorph, tautomer, enantiomer, pharmaceutically acceptable salt or prodrug thereof:

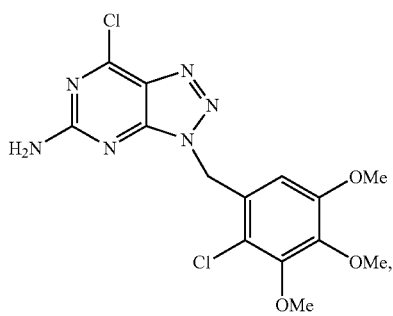

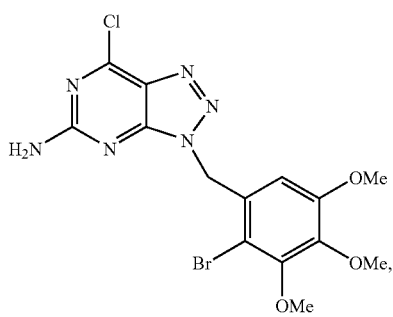

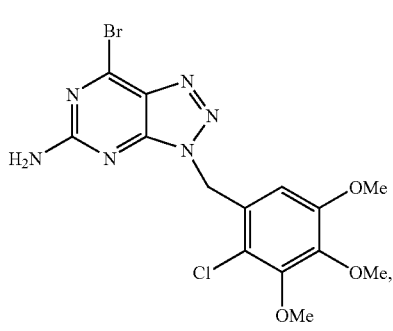

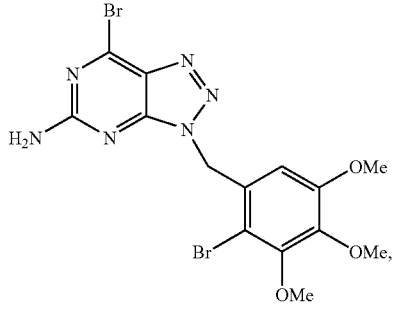

-continued

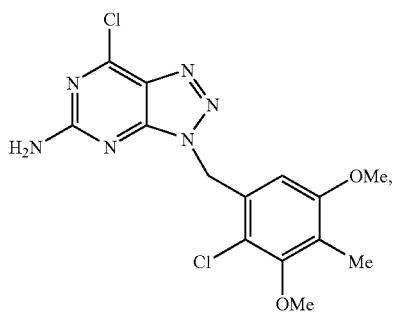

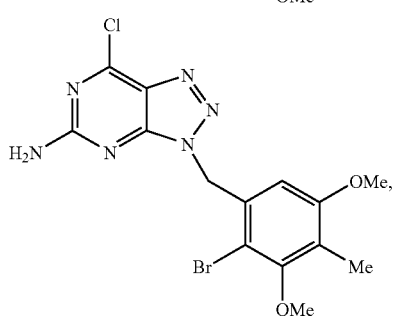

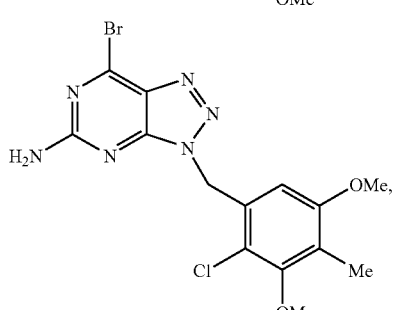

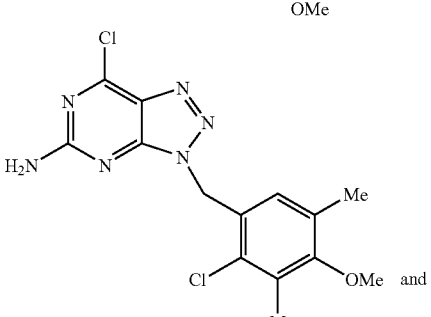

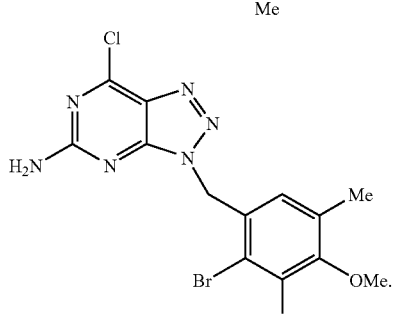

11. The compound of claim 6, wherein the compound is a member selected from the group below, or a polymorph, tautomer, enantiomer, pharmaceutically acceptable salt or prodrug thereof:

-continued
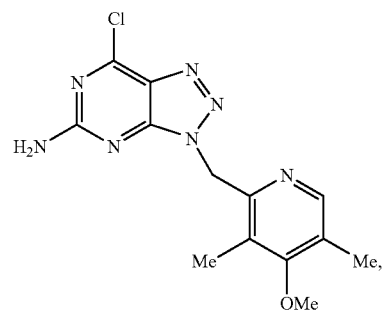
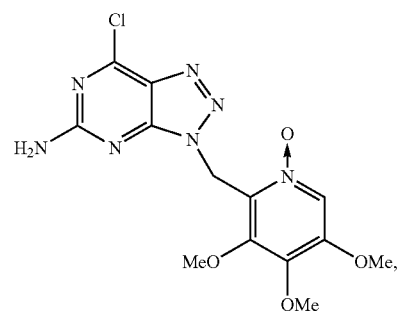
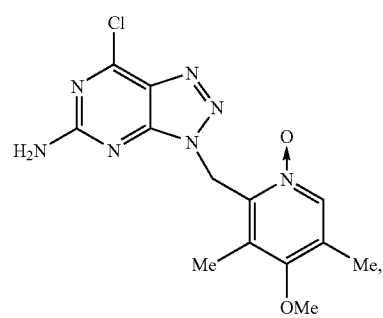
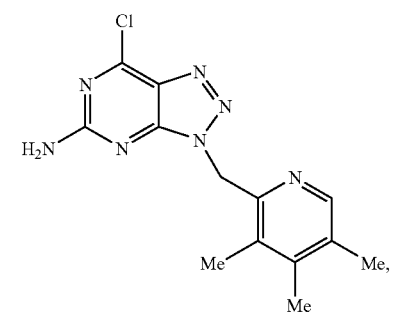
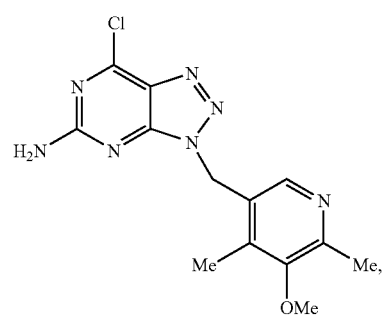
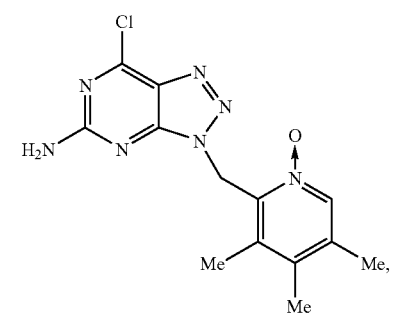
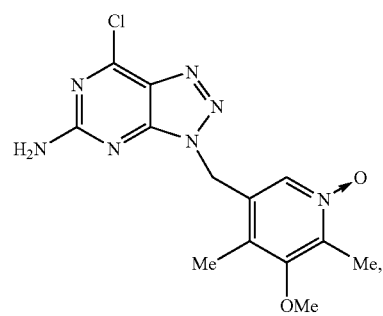
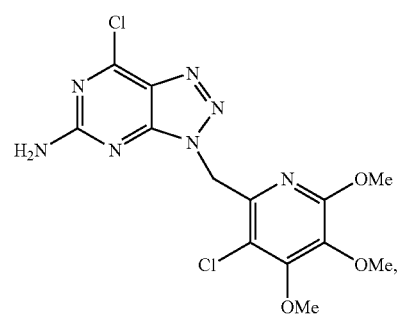
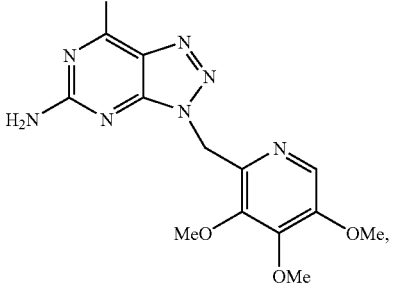
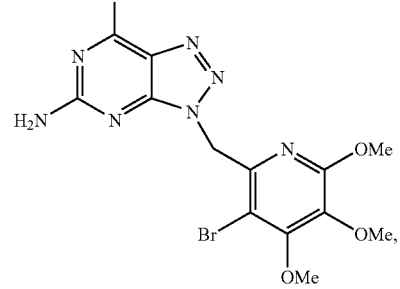

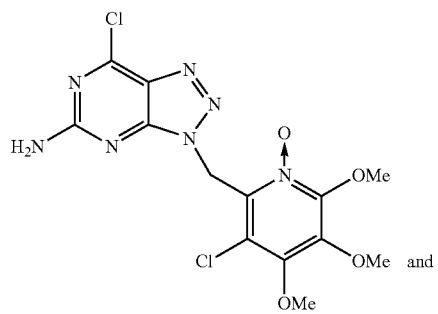
and
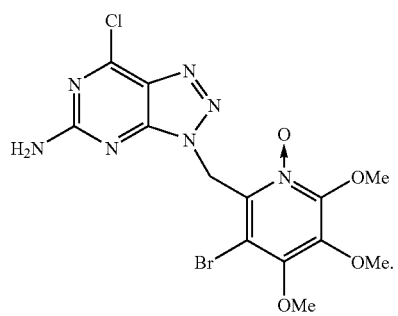
12. The compound of claim 6, wherein the compound is a member selected from the group below, or a polymorph, tautomer, enantiomer, pharmaceutically acceptable salt or prodrug thereof:
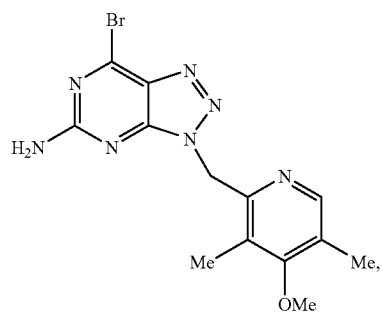
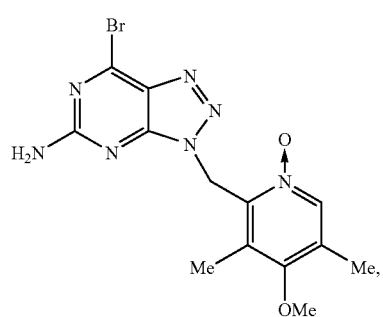
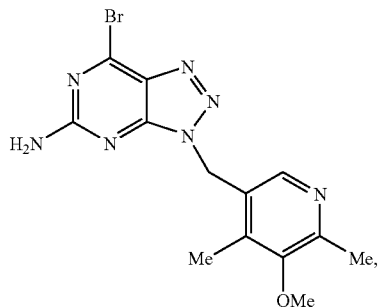
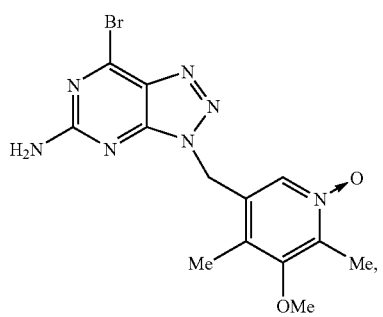
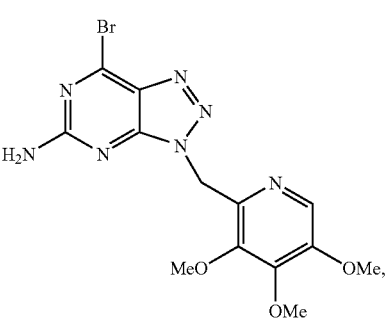
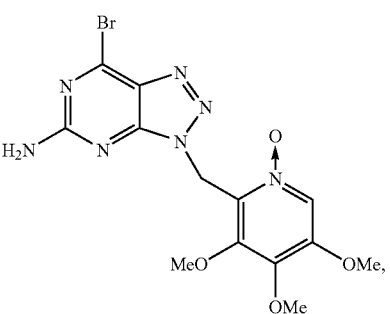
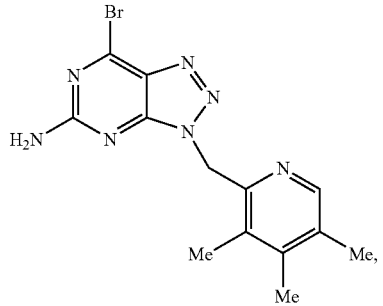

-continued
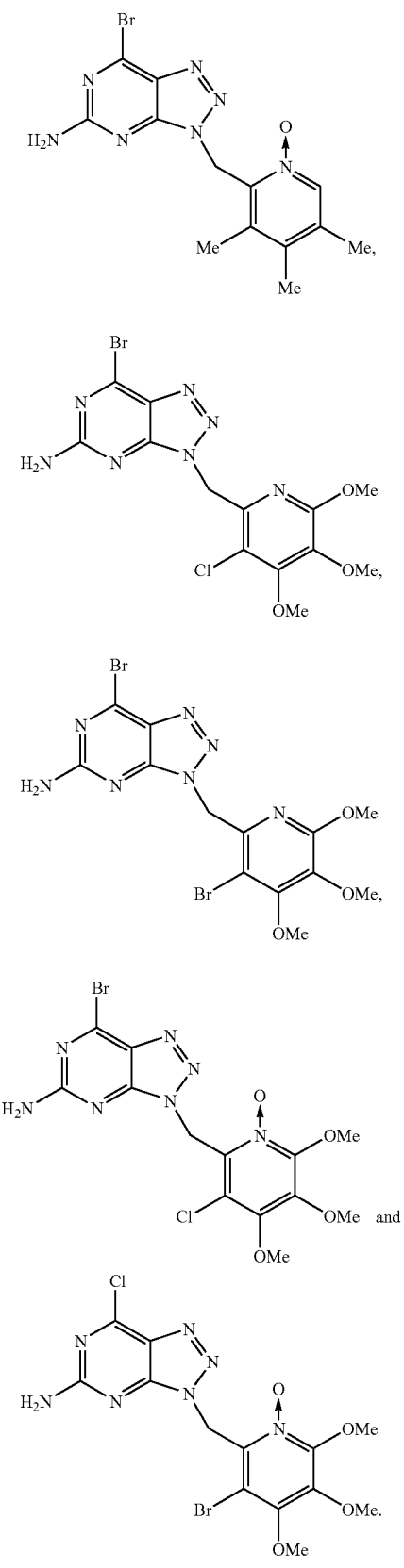
13. The compound of claim 6, wherein the compound is a member selected from the group below, or a polymorph, tautomer, enantiomers, pharmaceutically acceptable salt or prodrug thereof:
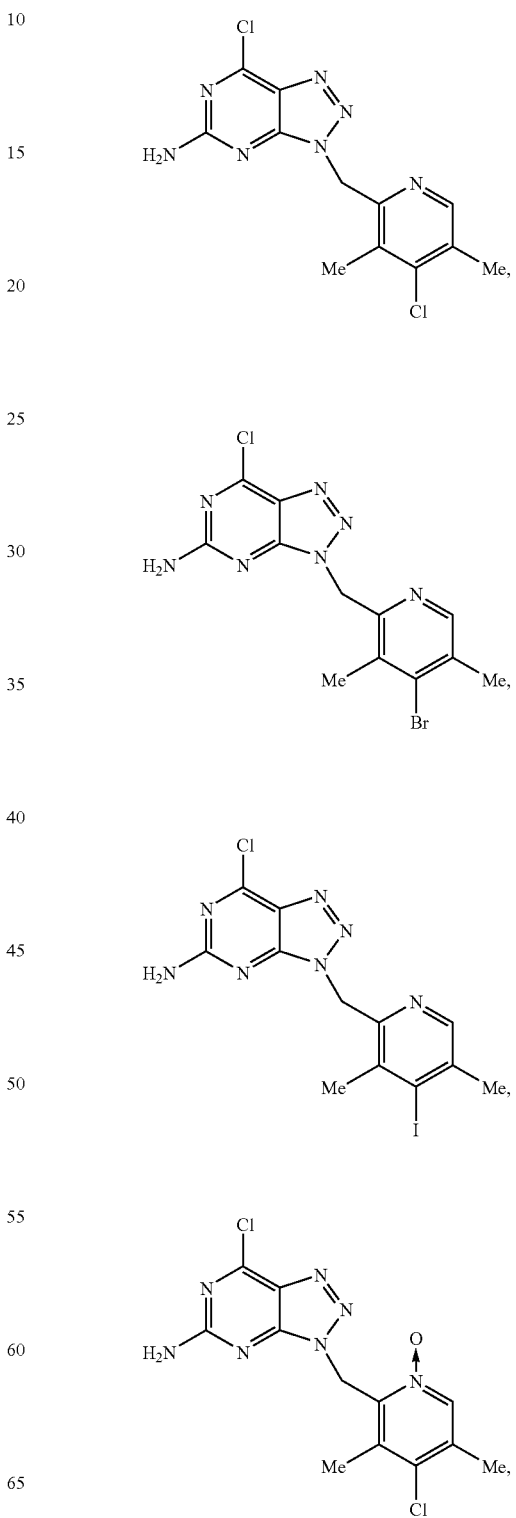

-continued

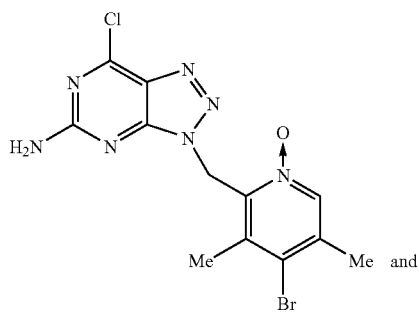

and

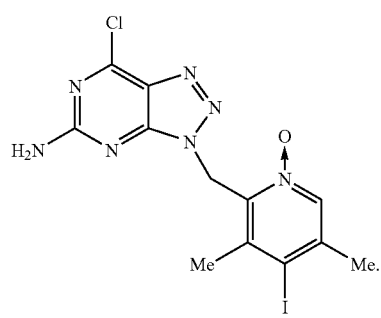

14. The compound of claim 6, wherein the compound is a member selected from the group below, or a polymorph, tautomer, enantiomers, pharmaceutically acceptable salt or prodrug thereof:

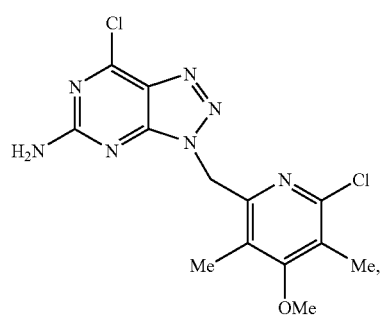

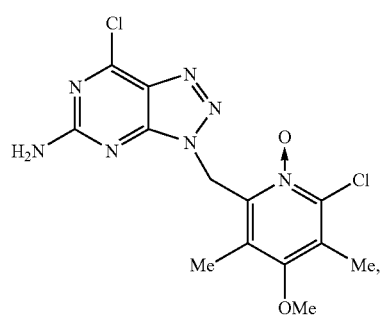

-continued

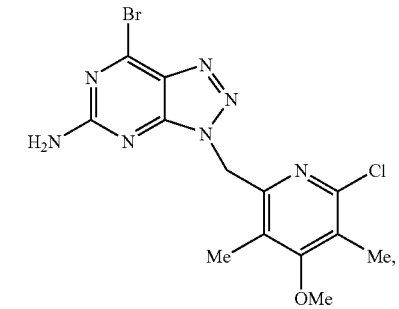

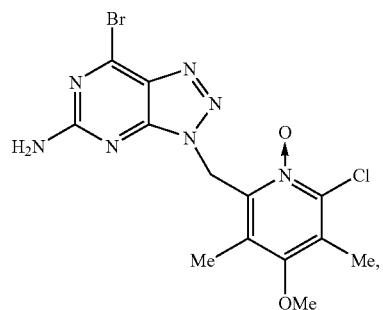

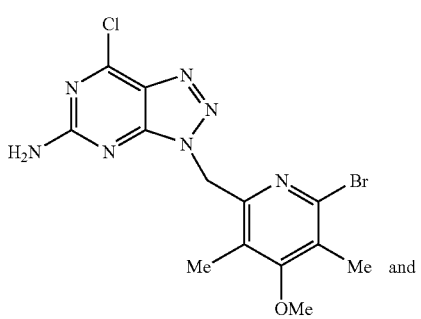

and

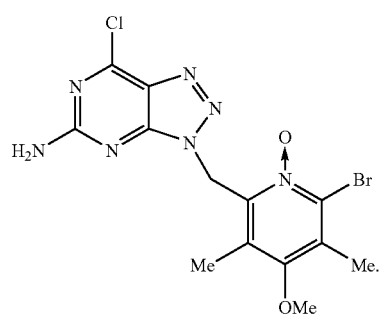

15. The compound of claim 6, wherein the compound is a member selected from the group below, or a polymorph, tautomer, enantiomers, pharmaceutically acceptable salt or prodrug thereof:

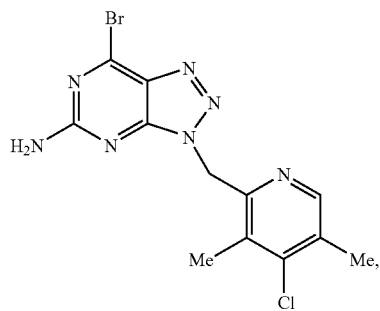

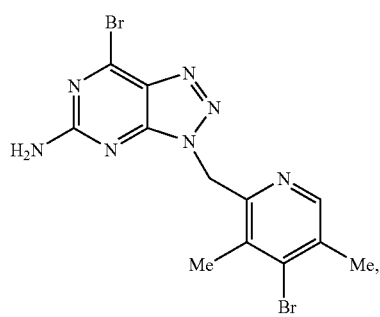

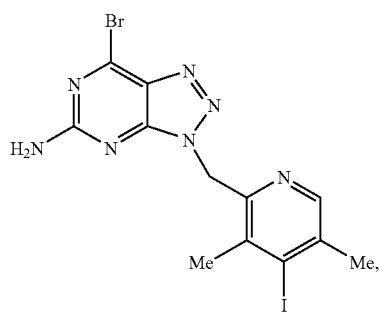

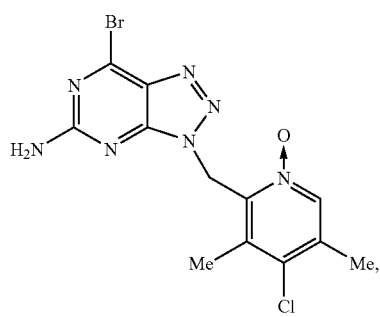

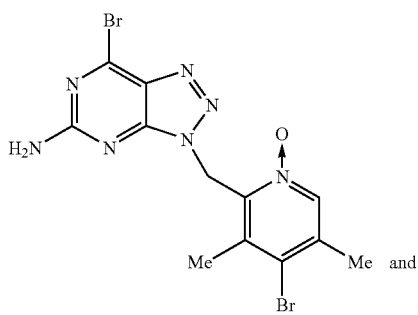

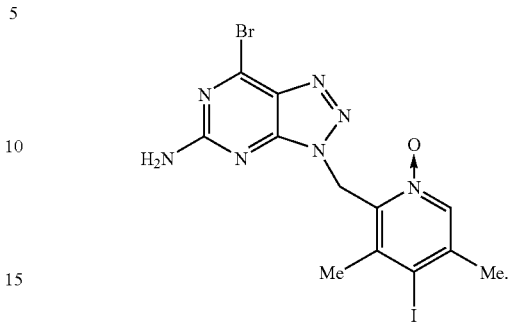

16. The compound of claim 6, wherein the compound is represented by the formula below, or a polymorph, tautomer, pharmaceutically acceptable salt or prodrug thereof:

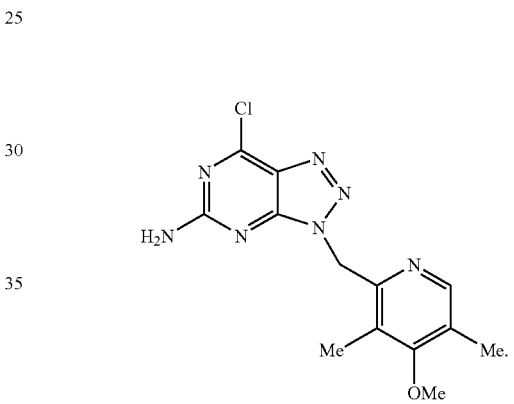

17. The compound of claim 6, wherein the compound is represented by the formula below, or a polymorph, tautomer, pharmaceutically acceptable salt or prodrug thereof:

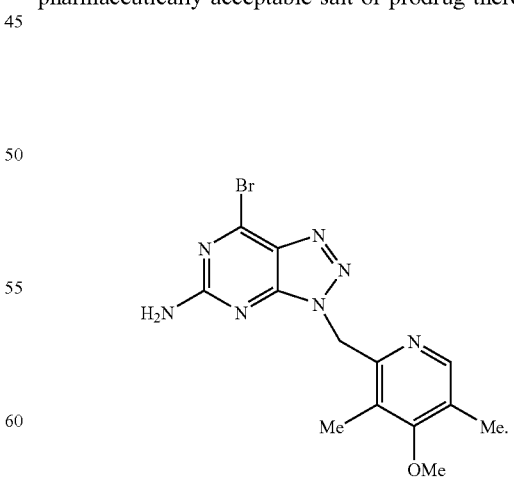

18. The compound of claim 6, wherein the compound is represented by the formula below, or a polymorph, tautomer, pharmaceutically acceptable salt or prodrug thereof:

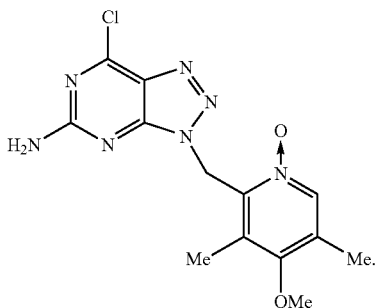

19. The compound of claim 6, wherein the compound is represented by the formula below, or a polymorph, ester, tautomer, pharmaceutically acceptable salt or prodrug thereof:

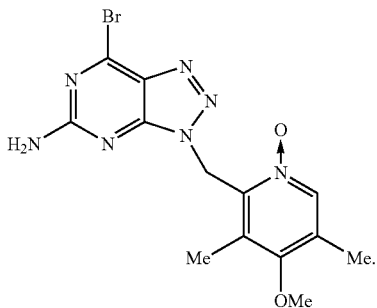

20. A pharmaceutical composition comprising one or more pharmaceutical acceptable excipient and at least one compound represented by Formula I below, or a polymorph, ester, tautomer, enantiomer, pharmaceutically acceptable salt or prodrug thereof,

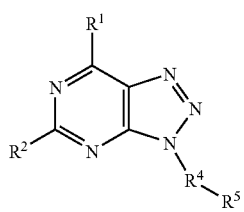

Formula I wherein:
$R^1$ is halogen, —$OR^{11}$, —$SR^{11}$ or lower alkyl;
R is —$NHR^8$;
$R^4$ is —$CHR^{12}$—, —C(O)—, —C(S)—, —S(O)— or —$SO_2$—;
$R^5$ is aryl, heteroaryl, alicyclic, or heterocyclic, wherein:
  the aryl group is substituted with 4 to 5 substituents,
  the heteroaryl group is substituted with 3 to 5 substituents,
  the alicyclic group is substituted with 3 to 5 substituents,
  the heterocyclic group is substituted with 3 to 5 substituents, and
  the substituents are selected from the group consisting of halogen, lower alkyl, lower alkenyl, lower alkynyl, —$SR^8$, —$OR^8$, —CN, —C(O)OH, —C(O)$R^9$, —$NO_2$, —$NR^8R^{10}$, lower aryl, heteroaryl, alicyclic, lower heterocyclic, arylalkyl, heteroarylalkyl, amino, alkylamino, dialkylamino, oxo, perhaloalkyl, perhaloalkoxy, perhaloacyl, guanidinyl, pyridinyl, thiophenyl, furanyl, indolyl, and indazolyl, wherein $R^8$ and $R^{10}$ taken together with the N to which they are attached optionally form a ring of 3–7 ring atoms and 1–3 of the ring atoms are heteroatoms selected from the group of O, S and N;
$R^8$ is hydrogen, lower alkyl, lower alkenyl, lower alkynyl, lower aryl, lower heteroaryl, or —C(O)$R^9$;
$R^9$ is H, lower alkyl, lower alkenyl, lower alkynyl, lower aryl, lower heteroaryl, —$NR^{10}R^{10}$, or —$OR^{11}$, wherein $R^{10}$ and $R^{10}$ taken together optionally form a ring of 3–7 ring atoms and optionally 1–3 of the ring atoms are heteroatoms selected from the group of O, S and N;
$R^{10}$ is hydrogen, lower alkyl, lower heteroaryl, lower aryl, lower alkenyl, or lower alkynyl,
$R^{11}$ is lower alkyl, lower alkenyl, lower alkynyl, lower heteroaryl or lower aryl; and
$R^{12}$ is hydrogen or lower alkyl;
provided that when $R^5$ is alicyclic, the ring system does not contain any tetra-substituted ring carbons.

21. The pharmaceutical composition of claim 20, wherein:
$R^1$ is halogen;
$R^2$ is —$NH_2$,
$R^4$ is —$CH_2$—; and
$R^5$ is aryl or heteroaryl, wherein each of the aryl and heteroaryl is monocyclic or bicyclic and the aryl is substituted with 4 or 5 substituents and the heteroaryl is substituted with 3 to 5 substituents.

* * * * *